(12) United States Patent
Varanasi et al.

(10) Patent No.: US 10,828,393 B2
(45) Date of Patent: Nov. 10, 2020

(54) SI—O—N—P RELATED FABRICATION METHODS, SURFACE TREATMENTS AND USES THEREOF

(71) Applicants: The Texas A&M University System, College Station, TX (US); BOARD OF REGENTS, THE UNIVERSITY OF TEXAS SYSTEM, Austin, TX (US)

(72) Inventors: Venu Varanasi, Lewisville, TX (US); Pranesh Aswath, Grapevine, TX (US); Philip Kramer, Dallas, TX (US); Megen Velten, Beeville, TX (US); Azhar Ilyas, Arlington, TX (US)

(73) Assignees: The Texas A&M University System, College Station, TX (US); Board of Regents, The University of Texas System, Austin, TX (US)

( * ) Notice: Subject to any disclaimer, the term of this patent is extended or adjusted under 35 U.S.C. 154(b) by 116 days.

(21) Appl. No.: 15/455,120

(22) Filed: Mar. 9, 2017

(65) Prior Publication Data
US 2017/0348459 A1 Dec. 7, 2017

Related U.S. Application Data

(60) Provisional application No. 62/305,956, filed on Mar. 9, 2016.

(51) Int. Cl.
| | | |
|---|---|---|
| *A61L 27/32* | (2006.01) |
| *A61L 27/54* | (2006.01) |
| *A61L 27/10* | (2006.01) |
| *A61L 27/38* | (2006.01) |
| *C09D 1/00* | (2006.01) |
| *C04B 35/597* | (2006.01) |
| *C23C 16/50* | (2006.01) |
| *C23C 16/22* | (2006.01) |
| *A61C 8/02* | (2006.01) |
| *A61C 8/00* | (2006.01) |
| *A61F 2/30* | (2006.01) |
| *C23C 16/30* | (2006.01) |
| *C04B 35/515* | (2006.01) |
| *C09D 7/60* | (2018.01) |

(52) U.S. Cl.
CPC ............ *A61L 27/32* (2013.01); *A61C 8/0006* (2013.01); *A61C 8/0015* (2013.01); *A61F 2/30771* (2013.01); *A61L 27/10* (2013.01); *A61L 27/38* (2013.01); *A61L 27/54* (2013.01); *C04B 35/5154* (2013.01); *C04B 35/597* (2013.01); *C09D 1/00* (2013.01); *C09D 7/60* (2018.01); *C23C 16/22* (2013.01); *C23C 16/30* (2013.01); *C23C 16/50* (2013.01); *A61F 2/3094* (2013.01); *A61F 2002/3084* (2013.01); *A61F 2002/3093* (2013.01); *A61F 2310/0061* (2013.01); *A61F 2310/00796* (2013.01); *A61F 2310/00874* (2013.01); *A61L 2300/112* (2013.01); *A61L 2300/412* (2013.01); *A61L 2300/606* (2013.01); *A61L 2400/12* (2013.01); *A61L 2400/18* (2013.01); *A61L 2420/02* (2013.01); *A61L 2420/06* (2013.01); *A61L 2430/02* (2013.01); *A61L 2430/12* (2013.01); *C04B 2235/42* (2013.01)

(58) Field of Classification Search
None
See application file for complete search history.

(56) References Cited

U.S. PATENT DOCUMENTS

| | | | |
|---|---|---|---|
| 6,136,654 | A | 10/2000 | Kraft et al. |
| 2009/0177282 | A1 | 7/2009 | Bureau et al. |
| 2010/0261034 | A1 | 10/2010 | Cardarelli et al. |

FOREIGN PATENT DOCUMENTS

| | | |
|---|---|---|
| CA | 2593781 A1 | 7/2006 |
| CA | 2660141 A1 | 2/2008 |

(Continued)

OTHER PUBLICATIONS

Hussein et al., "Fabrication and characterization of PECVD phosphorus-doped silicon oxynitride layers for integrated optics applications", Proceedings Symposium IEEE/LEOS Benelux Chapter, 2004, pp. 91-94.*

(Continued)

*Primary Examiner* — Robert A Wax
*Assistant Examiner* — Randeep Singh
(74) *Attorney, Agent, or Firm* — Meunier Carlin & Curfman LLC

(57) ABSTRACT

Disclosed are compositions, methods and processes for fabricating and using a device or other implement including a surface or surfaces having a nanoscale or microscale layer or coating of Si—O—N—P. These coatings and/or layers may be continuous, on the surface or discontinuous (e.g., patterned, grooved), and may be provided on silica surfaces, metal (e.g., titanium), ceramic, and combination/hybrid materials. Methods of producing an implantable device, such as a load-bearing or non-load-bearing device, such as a bone or other structural implant device (load-bearing), are also presented. Craniofacial, osteogenic and disordered bone regeneration (osteoporosis) uses and applications of devices that include at least one surface that is treated to include a nanoscale or microscale layer or coating of Si—O—N—P are also provided. Methods of using the treated and/or coated devices to enhance enhanced vascularization and healing at a treated surface of a device in vivo, is also presented.

11 Claims, 62 Drawing Sheets
Specification includes a Sequence Listing.

(56) References Cited

FOREIGN PATENT DOCUMENTS

TW       373289 B      11/1999
WO    2006074550 A1     7/2006

OTHER PUBLICATIONS

Gnaser et al., "Phosphorus doping of Si nanocrystals embedded in silicon oxynitride determined by atom probe tomography", Journal of Applied Physics, vol. 115, 2014, pp. 1-7.*
Wan et al., "Si—N—O Films Synthesized by Plasma Immersion Ion Implantation and Deposition (PIII&D) for Blood-Contacting Biomedical Applications", IEEE Transactions of Plasma Science, vol. 34, No. 4, Aug. 2006, pp. 1160-1165.*
Wang et al., "Silicon nitride coating on titanium to enable titanium-ceramic bonding", Journal of Biomedical Materials Research, vol. 46, Issue 2, Aug. 1999, pp. 262-270.*
Wopenka et al., "The Tendon-to-Bone Transition of the Rotator Cuff: A Preliminary Raman Spectroscopic Study Documenting the Gradual Mineralization Across the Insertion in Rat Tissue Samples", 2008, Applied Spectroscopy pp. 1285-1294, vol. 62, No. 12.
Stone et al., "BMD at Multiple Sites and Risk of Fracture of Multiple Types: Long-Term Results From the Study of Osteoporotic Fractures", 2003, Journal of Bone and Mineral Research, pp. 1947-1954, vol. 18, No. 11.
Kohn et al., "Exercise Alters Mineral and Matrix Composition in the Absence of Adding New Bone", 2009, Cells Tissues Organs, pp. 33-37, vol. 189.
Awonusi et al., "Carbonate Assignment and Calibration in the Raman Spectrum of Apatite", 2007, Calcif Tissue Int., pp. 46-52, vol. 81.
Akkus et al., "Age-related changes in physicochemical properties of mineral crystals are related to impaired mechanical function of cortical bone", 2004, Bone, pp. 443-453, vol. 34.
Roschger et al., "Validation of Quantitative Backscattered Electron Imaging for the Measurement of Mineral Density Distribution in Human Bone Biopsies", 1998, Bone, pp. 319-326, vol. 23, No. 4.
Fujita et al., "Time-lapse observation of cell alignment on nanogrooved patterns", 2009, J. R. Soc. Interface. pp. S269-S277, vol. 6.
Gomez-Vega et al., "Bioactive glass coatings with hydroxyapatite and Bioglass particles on Ti-based implants. 1. Processing", 2000, Biomaterials, pp. 105-111, vol. 21.
Bettinger et al., "Engineering Substrate Topography at the Micro- and Nanoscale to Control Cell Function", 2009, Angew. Chem. Int. Ed., pp. 5406-5415, vol. 48.
Clark et al., "Topographical control of cell behaviour: II. multiple grooved substrata", 1990, Development, pp. 635-644, vol. 108.
Gritsenko et al., "Short-range order in non-stoichiometric amorphous silicon oxynitride and silicon-rich nitride", 2002, Journal of Non-Crystalline Solids, pp. 96-101, vol. 297.
Campmany et al., "Optical, vibrational and compositional study of amorphous silicon oxynitride thin films grown by using N20 + SiH4 gas mixtures", Nov. 20, 1992, Applied Surface Science, pp. 695-700, vol. 70, Issue 71.
Poon et al., "Bonding structures of silicon oxynitride prepared by oxidation of Si-rich silicon nitride", Jun. 15, 2004, Thin Solid Films, pp. 42-45.
Chan et al., "Oxynitride gate dielectric prepared by thermal oxidation of low-pressure chemical vapor deposition silicon-rich silicon nitride", 2003, Microelectronics Reliability, pp. 611-616, vol. 43.
Behrens et al., "Geometric structure of thin SiOxNy films on Si(100)",1998, Surface Science, pp. 729-733, vol. 402-404.
Ay et al., "Comparative investigation of hydrogen bonding in silicon based PECVD grown dielectrics for optical waveguides", 2004, Optical Materials, pp. 33-46, vol. 26.
Philipp, H.R., Optical Properties of Non-Crystalline Si, SiO, SiOx and SiOz, 1971, J. Phys. Chem Solids, pp. 1935-1945, vol. 32.
Tarey et al., "Characterization of Thin Films by Glancing Incidence X-Ray Diffraction", 1987, The Rigaku Journal, pp. 11-15, vol. 4, No. 1/2.
Hussein et al., "Characterization of thermally treated PECVD SiON layers", Dec. 2001, Proceeding IEEE / LEOS, pp. 265-268.
Cao et al., "Bioactive Materials", 1996, Ceramics International, pp. 493-507, vol. 22.
Padilla et al., "Hydroxyapatite/SiO2—CaO—P2O5 glass materials: In vitro bioactivity and biocompatibility", 2006, Acta Biomaterialia, pp. 331-342, vol. 2.
Kim et al., "Process and kinetics of bonelike apatite formation on sintered hydroxyapatite in a simulated body fluid", 2005 Biomaterials, pp. 4366-4373, vol. 26.
Santos et al., "Chemical and topographical influence of hydroxyapatite and β-tricalcium phosphate surfaces on human osteoblastic cell behavior", 2008, J. Biomed Mater Res, pp. 510-520, vol. 89A.
Xynos et al., "Gene-expression profiling of human osteoblasts following treatment with the ionic products of Bioglass 45S5 dissolution", 2000, J. Biomed Mater Res, pp. 151-157, vol. 55.
Kumta et al., "Nanostructured calcium phosphates for biomedical applications: novel synthesis and characterization", 2005, Acta Biomaterialia, pp. 65-83, vol. 1.
Ning et al., "Effects of silica on the bioactivity of calcium phosphate composites in vitro", 2005, Journal of Materials Science: Materials in Medicine, pp. 355-360, vol. 16.
Lee et al., "Proliferation, differentiation, and calcification of preosteoblast-like MC3T3-E1 cells cultured onto noncrystalline calcium phosphate glass", 2003, J Biomed Mater Res, pp. 188-195, vol. 69A.
Kokubo et al., "How useful is SBF in predicting in vivo bone bioactivity", 2006, Biomaterials, pp. 2907-2915, vol. 27.
Kokubo et al., "Chemical reaction of bioactive glass and glass-ceramics with a simulated body fluid", 1992, Journal of Materials Science: Materials in Medicine, pp. 79-83, vol. 1992.
Redey et al., "Osteoclast adhesion and activity on synthetic hydroxyapatite, carbonated hydroxyapatite, and natural calcium carbonate: Relationship to surface energies", 1999, J Biomed Mater Res, pp. 140-147, vol. 45.
Murray et al., "The Influence of the Surface Energy and Roughness of Implants on Bone Resorption", 1989, The Journal of Bone and Joint Surgery, pp. 632-637, vol. 71B.
Webb et al., "Relative importance of surface wettability and charged functional groups on NIH 3T3 fibroblast attachment, spreading, and cytoskeletal organization", 1998, J Biomed Mater Res, pp. 422-430, vol. 42.
Feng et al., "Characterization of surface oxide films on titanium and bioactivity", 2002, Journal of Materials Science: Materials in Medicine, pp. 457-464, vol. 13.
Jaiswal et al., "Osteogenic Differentiation of Purified, Culture-Expanded Human Mesenchymal Stem Cells In Vitro", 1997, Journal of Cellular Biochemistry, pp. 295-312, vol. 64.
Bare, Simon R., "Xanes Measurements and Interpretation", Jul. 26-29, 2005, EXAFS Data Collection and Analysis course, APS, pp. 1-51.
Bergwitz et al., "Regulation of Phosphate Homeostasis by PTH, Vitamin D, and FGF23", 2010, The Annual Review of Medicine, pp. 91-104, vol. 61.
Rangiani et al., "Protective Roles of DMP1 in High Phosphate Homeostasis", Aug. 2012, PLoS One, pp. 1-16, vol. 7, Issue 8, e42329.
Termine et al., "Hydroxide and Carbonate in Rat Bone Mineral and Its Synthetic Analogues",1973, Calc. Tiss. Res., pp. 73-82, vol. 13.
Donnelly et al., Effects of tissue age on bone tissue material composition and nanomechanical properties in the rat cortex, Mar. 1, 2010, J Biomed Mater Res A., pp. 1048-1056, vol. 92, Issue 3.
Aruwajoye et al., "Microcrack density and nanomechanical properties in the subchondral region of the immature piglet femoral head following ischemic osteonecrosis", 2013, Bone, pp. 632-639, vol. 52.
Demirkiran et al., "XANES analysis of calcium and sodium phosphates and silicates and hydroxyapatite—Bioglass® 45S5 co-sintered bioceramics", 2011, Materials Science and Engineering C, pp. 134-143, vol. 31.
Kruse et al., "Phosphorus L2,3-edge XANES: overview of reference compounds", 2009, Journal of Synchrotron Radiation, pp. 247-259, vol. 16.

(56) References Cited

OTHER PUBLICATIONS

Rajendran et al., "XANES analysis of dried and calcined bones", 2013, Materials Science and Engineering C, pp. 3968-3979, vol. 33.
Toyosawa et al., "Dentin Matrix Protein 1 Is Predominantly Expressed in Chicken and Rat Osteocytes But Not in Osteoblasts", 2001, Journal of Bone and Mineral Science, pp. 2017-2026, vol. 16, No. 11.
Bigi et al., "Chemical and Structural Characterization of the Mineral Phase from Cortical and Trabecular Bone", 1997, Journal of Inorganic Biochemistry, pp. 45-51, vol. 68.
Burnell et al., Normal Maturational Changes in Bone Matrix, Mineral, and Crystal Size in the RatP, 1980, Calcified Tissue International, pp. 13-19, vol. 31.
Rey et al., "The Carbonate Environment in Bone Mineral: A Resolution-Enhanced Fourier Transform Infrared Spectroscopy Study", 1989, Calcified Tissue International, pp. 157-164, vol. 45.
Kuiper et al., "Chemical Composition of LPCVD Silicon Nitride and Silicon Oxynitride Layers", Philips Journal of Research, vol. 38, Nos. 1/2, 1983, pp. 1-18.
Varanasi et al., "Si and Ca Individually and Combinatorially Target Enhanced MC3T3-E1 Subclone 4 Early Osteogenic Marker Expression", 2012, Journal of Oral Implantology, pp. 325-336, vol. 35, No. Four.
Arias et al., "Micro- and nano-testing of calcium phosphate coatings produced by pulsed laser deposition", 2003 Biomaterials, pp. 3403-3408, vol. 24.
Amaral et al., "Wettability and surface charge of Si3N4-bioglass composites in contact with simulated physiological liquids", 2002, Biomaterials, pp. 4123-4129, vol. 23.
Correia et al., "Estimation of the Surface Tension of a Solid: Application to a Liquid Crystalline Polymer", 1997, Journal of Colloid and Interface Science, pp. 361-369, vol. 189.
Bosetti et al., "Type I collagen production by osteoblast-like cells cultured in contact with different bioactive glasses", 2002, J Biomed Mater Res, pp. 189-195, vol. 64A.
Li et al., "X-ray absorption spectroscopy of silicon dioxide (SiOr) polymorphs: The structural characterization of opal", 1994, American Mineralogist, pp. 622-632, vol. 79.
Elgayar et al., "Structural analysis of bioactive glasses", 2005, Journal of Non-Crystalline Solids, pp. 173-183, vol. 351.
Kasrai et al., "Sampling depth of total electron and fluorescence measurements in Si L- and K-edge absorption spectroscopy", 1996, Applied Surface Science, pp. 303-312, vol. 99.
Li et al., "High-Resolution Si K- and L23-Edge Xanes of a-Quartz and Stishovite", 1993, Solid State communications, pp. 613-617, vol. 87, Issue 7.
Pedone et al., "New Insights into the Atomic Structure of 45S5 Bioglass by Means of Solid-State NMR Spectroscopy and Accurate First-Principles Simulations", 2010, Chemistry of Materials, pp. 5644-5652, vol. 22.
Li et al., "Coordination of Si in Na2O—SiO2—P2Os glasses using Si K- and L-edge XANES", 1996, American Mineralogist, pp. 111-118, vol. 81.
Wilson et al., "Effect of thermal treatment on the growth, structure and luminescence of nitride-passivated silicon nanoclusters", 2011, Nanoscale Research Letters, pp. 1-12, vol. 6, Issue 168, pp. 1-12.
Criado et al., "Structural analysis of silicon oxynitride films deposited by PECVD", 2004, Materials Science and Engineering B, pp. 123-127, vol. 112.
Pinakidou et al., "XAFS characterization of buried SixNyOz samples", 2003, Nuclear Instruments and Methods in Physics Research B, pp. 66-72, vol. 200.
Fitzgerald et al., "A Neutron and X-Ray Diffraction Study of Bioglass® with Reverse Monte Carlo Modelling", 2007, Adv. Funct. Mater., pp. 3746-3753, vol. 17.
Skipper et al., "The structure of a bioactive calcia-silica sol-gel glass", Apr. 29, 2005, Journal of Materials Chemistry, pp. 2369-2374, vol. 15.
Martin et al., "A study of the formation of amorphous calcium phosphate and hydroxyapatite on melt quenched Bioglass using surface sensitive shallow angle X-ray diffraction", 2009, J Mater Sci: Mater Med, pp. 883-888, vol. 20.
Newport et al., "Physics and Chemistry of Glasses", Jun. 2009, European Journal of Glass Science and Technology Part B, pp. 137-143, vol. 50, No. 3.
Garvie et al., "Use of electron-energy loss near-edge tine structure in the study of minerals", American Mineralogist, vol. 79, 1994, pp. 411-425.
Fitzgerald et al., "Bioactive glass sol-gel foam scaffolds: Evolution of nanoporosity during processing and in situ monitoring of apatite layer formation using small- and wide-angle X-ray scattering", 2008, J Biomed Mater Res, pp. 76-83, vol. 91A.
Schmittgen et al., "Analyzing real-time PCR data by the comparative CT method", Jun. 5, 2008, Nature Protocols, pp. 1101-1108, vol. 3, No. 6.
Idris et al., "Film Characteristics of Low-Temperature Plasma-Enhanced Chemical Vapor Deposition Silicon Dioxide Using Tetraisocyanatesilane and Oxygen", 1998, Japanese Journal of Applied Physics, pp. 6562-6568, vol. 37, Part 1, No. 12A.
Harp et al., "Spatially-resolved X-ray Absorption Near-edge Spectroscopy of Silicon in Thin Silicon-oxide Films", 1990, Physica Scripta, pp. 23-27, vol. T31.
Nojiri et al., "Cytoplasmic Superoxide Causes Bone Fragility Owing to Low-Turnover Osteoporosis and Impaired Collagen Cross-Linking", 2011, Journal of Bone and Mineral Research, pp. 2682-2694, vol. 26, No. 11.
Liebschiner et al., Optimization of Bone Scaffold Engineering for Load Bearing Applications:, 2003, Topics in Tissue Engineering, Chapter 6, pp. 1-39.
Varanasi et al., "The ionic products of bioactive glass particle dissolution enhance periodontal ligament fibroblast osteocalcin expression and enhance early mineralized tissue development", 2011, J Biomed Mater Res Part A, pp. 177-184, vol. 98A.
Busscher et al., "The Effect of Surface Roughening of Polymers on Measured Contact Angles of Liquids", 1984, Colloids and Surfaces, pp. 319-331, vol. 9.
Cerruti et al., "Surface Modifications of Bioglass Immersed in TRIS-Buffered Solution. A Multitechnical Spectroscopic Study", 2005, Journal of Physical Chemistry, pp. 14496-14505, vol. 109.
Tilocca et al., "Structural Effects of Phosphorus Inclusion in Bioactive Silicate Glasses", 2007, J. Phys. Chem. B, pp. 14256-14264, vol. 111, No. 51.
Jones et al., "Dose-Dependent Behavior of Bioactive Glass Dissolution", 2001, J Biomed Mater Res, pp. 720-726, vol. 58.
Isaac et al., "Effects of Strontium-Doped Bioactive Glass on the Differentiation of Cultured Osteogenic Cells", 2011, European Cells and Materials , pp. 130-143, vol. 21.
Milona et al., "Expression of alternatively spliced isoforms of human Sp7 in osteoblast-like cells", 2003, BMC Genomics, pp. 1-11, vol. 4, Issue 43.
Varanasi et al., Enhanced osteocalcin expression by osteoblast-like cells (MC3T3-E1) exposed to bioactive coating glass (SiO2—CaO—P2O5—MgO—K2O—Na2O system) ions, 2009, Acta Biomaterialia, pp. 3536-3547, vol. 5.
Renno et al., "Characterization and In Vivo Biological Performance of Biosilicate" Hindawai Publishing Company, BioMed Research Internationals, vol. 2013, Article ID 141427, pp. 1-7.
Vert et al., "Terminology for biorelated polymers and application" (IUPAC Recommendations 2012), Jan. 11, 2012,J. Pure Appl. Chem., pp. 377-410, vol. 84, No. 2.
Kim et al., "Electrochemical surface modification of titanium in dentistry", 2009, Dental materials Journal, pp. 20-36, vol. 28, No. 1.
Sul et al., "The roles of surface chemistry and topgraphy in the strength and rate of osseointegration of titanium implant in the bone", 2009, Journal of Biomedical Materials Research Part A, pp. 942-950, vol. 89A.
Alghamdi et al., "Biological response to titanium implants coated with nanocrystals calcium phosphate or type 1 collagen in a dog model", 2013, Clin. Oral Impl. Res., pp. 475-483, vol. 24.
Kang et al., "The effect of calcium ion concentration on the on the bones response to oxidized titanium implants", 2012, Clin. Oral Impl. Res., pp. 690-697, vol. 23.

(56) References Cited

OTHER PUBLICATIONS

Branemark, Per-Ingvar, "Osseointegration and its experimental background", Sep. 1983, The Journal of Prosthetic Dentistry, vol. 50, No. 3, pp. 399-410.
Zupnik et al., "Factors Associated with Dental Implant Survival: A 4-Year Retrospective Analysis", Oct. 2011, J. Periodontol, pp. 1390-1395, vol. 82, No. 3.
Rho et al., "Mechanical Properties and the hierarchical structure of the bone",1998, Medical Engineering & Physics, pp. 92-102, vol. 20.
Athanasiou et al., "Fundamentals of Biomechanics in Tissue Engineering of Bone", 2000,Tissue Engineering, pp. 361-381, vol. 6, No. 4.
Ritchie, Robert O., "The conflicts between strength and toughness", Nov. 2011, Nature Materials, pp. 817-822, vol. 10.
Weiner et al., "Bone structure: from angstroms to microns", 1992, The FASEB Journal, pp. 879-885, vol. 6, No. 3.
Legros et al., "Age-Related Changes in Mineral of Rat and Bovine Cortical Bone", Calcified Tissue International, 1987, pp. 137-144, vol. 41.
Cashman, Kevin D., Milk minerals (including trace elements) and bone health), 2006, International Dairy Journal, pp. 1389-1398, vol. 16.
Hadjidakis et al., "Bone Remodeling", 2006, Annals New York Academy of Sciences, pp. 385-396, vol. 1092.
Raggatt et al., "Cellular and Molecular Mechanisms of Bone Remodeling", Aug. 13, 2010,The Journal of Biological Chemistry, pp. 25103-25108, vol. 285, No. 33.
Arnett, Timothy R. "Extracellular pH Regulates Bone Cell Function 1-3", 2008, The Journal of Nutrition, pp. 415S-418S, Second International Acid-Base Symposium, Nutrition-Health-Disease.
Deal, Chad, "Potential new drug targets for osteoporosis", Nov. 12, 2008, Nature Clinical Practice, vol. 5, No. 1, pp. 20-27.
Fisher et al., "Six Genes Expressed in Bones and Teeth Encode the Current Member of the SIBLING Family of Proteins", 2003, Connective Tissue Research, pp. 33-40, vol. 44, Supplemental No. 1.
George et al., "Characterization of a Novel Dentin Matrix Acidic Phosphoprotein", 1993, The Journal of Biological Chemistry, pp. 12624-12630, vol. 268, No. 17.
D'Souza et al., "Gene Expression Patterns of Murine Dentin Matrix Protein 1 (Dmp1) and Dentin Sialophosphoprotein (DSPP) Suggest Distinct Developmental Functions In Vivo*", 1997, Journal of Bone and Mineral Research, pp. 2040-2049, vol. 12, No. 12.
Feng et al., "Dentin Matrix Protein 1, a Target Molecule for Cbfa1 in Bone, Is a Unique Bone Marker Gene", Nov. 10, 2002, Journal of Bone and Mineral Research, pp. 1822-1831, vol. 17, No. 10.
MacDougall et al., "Identification of a Novel Isoform of Mouse Dentin Matrix Protein 1: Spatial Expression in Mineralized Tissues", 1998, Journal of Bone and Mineral Research, pp. 422-431, vol. 13, No. 3.
Ye et al., "Deletion of Dentin Matrix Protein-1 Leads to a Partial Failure of Maturation of Predentin into Dentin Hypomineralization, and Expanded Cavities of Pulp and Root Canal during Postnatal Tooth Development", Feb. 13, 2004, The Journal of Biological Chemistry, pp. 19141-19148, vol. 279, Issue 18.
Lorenz-Depiereux et al., "DMP1 mutations in autosomal recessive hypophosphatemia implicate a bone matrix protein in the regulation of phosphate homeostasis", Oct. 8, 2006, Nature Genetics, pp. 1248-1250, vol. 38, No. 11.
Qin et al., "Dentin Matrix Protein 1 (DMP1): New and Important Roles for Biomineralization and Phosphate Homeostasis", 2007, J Dent Res, pp. 1134-1141, vol. 86, No. 12.
He et al., "Nucleation of apatite crystals in vitro by self-assembled dentin matrix protein 1", Jul. 20, 2003, Nature Materials, pp. 552-558, vol. 2.
Gajjeraman et al., "Matrix Macromolecules in Hard Tissues Control the Nucleation and Hierarchical Assembly of Hydroxyapatite", Jan. 12, 2007, The Journal of Biological Chemistry pp. 1193-1204, vol. 282, No. 2.
Tartaix et al., "In Vitro Effects of Dentin Matrix Protein-1 on Hydroxyapatite Formation Provide Insights into in Vivo Functions", 2004, The Journal of Biological Chemistry, pp. 18115-18120, vol. 279, No. 18.
Feng et al., "The Dentin Matrix Protein 1 (Dmp1) is Specifically Expressed in Mineralized, but not Soft, Tissues during Development", 2003, J Dent Res, pp. 776-780, vol. 82, No. 10.
Ponche et al., Relative influence of surface topography and surface chemistry on cell response to bone implant materials. Part 1: Physico-chemical effects, Proceedings of the Institution of Mechanical Engineers, Part H: Journal of Engineering in Medicine, vol. 223, Dec. 2010, pp. 1471-1486.
Ye et al., "Dmp1-deficient Mice Display Severe Defects in Cartilage Formation Responsible for a Chondrodysplasia-like Phenotype", Dec. 7, 2004, The Journal of Biological Chemistry, pp. 6197-6203, vol. 280, No. 7.
Ling et al., "DMP1 Depletion Decreases Bone Mineralization In Vivo: An FTIR Imaging Analysis", 2005, J Bone Miner Res, pp. 2169-2177, vol. 20, No. 12.
Spiegel, Peter K., "The First Clinical X-Ray Made in America—100 Years", 1995, AJR, pp. 241-243, vol. 163.
Ratner et al., "Biomaterials Science: An Introduction to Materials in Medicine", 1996, Academic Press, San Diego, California, pp. 1-497.
Huec et al., "Influence of porosity on the mechanical resistance of hydroxyapatite ceramics under compressive stress", 1995, Biomaterials, pp. 113-118, vol. 16, No. 2.
Akao et al., "Dense polycrystalline β-tricalcium phosphate for prosthetic applications", 1982, pp. 343-346, vol. 17, No. 2.
Takeda et al., "Effect of microstructure on fretting fatigue and sliding wear of highly workable titanium alloy, Ti—4.5Al—3V—2Mo—2Fe", 2004, International Journal of Fatigue, pp. 1003-1015, vol. 26, Issue 9.
Teoh, S. H, "Fatigue of biomaterials: a review", 2000, International Journal of Fatigue, pp. 825-837, vol. 22.
Bronzino, J.D., "Medical Devices and Systems", Taylor & Francis Group, The Biomedical Engineering Handbook: Third Edition, Taylor & Francis Group, Boca Raton, 2006, pp. 1-1404.
Hench, Larry L., "The story of Bioglass", 2006, J Mater Sci: Mater Med, pp. 967-978, vol. 17.
Flemming et al., "Effects of synthetic micro- and nano-structured surfaces on cell behavior", 1999, Biomaterials, pp. 573-588, vol. 20.
Feng et al., "Loss of DMP1 causes rickets and osteomalacia and identifies a role for osteocytes in mineral metabolism", Nov. 2006, Nature Genetics, pp. 1310-1315, vol. 38, No. 11.
Bouxsein et al., "Guidelines for Assessment of Bone Microstructure in Rodents Using Micro-Computed Tomography", 2010, Journal of Bone and Mineral Research, vol. 25, No. 7, pp. 1468-1486.
Quarles, L. Darryl, "Role of FGF23 in Vitamin D and Phosphate Metabolism: Implications in Chronic Kidney Disease", May 15, 2012, Exp Cell Res., pp. 1040-1048, vol. 318, Issue 9.
Tranah et al., "Systemic inflammation and ammonia in hepatic encephalopathy", 2013, Metab Brain Dis., pp. 1-5, vol. 28, No. 1.
Lai et al., "Excretion of resorption products from bioactive glass implanted in rabbit muscle", 2005, J Biomed Mater Res, pp. 398-407, vol. 75A.
Li et al., "Insights into new calcium phosphosilicate xerogels using an advanced characterization methodology", 2011, Journal of Non-Crystalline Solids, pp. 3548-3555, vol. 357.
Galliano et al., "Analysis by Nuclear Magnetic Resonance and Raman Spectroscopies of the Structure of Bioactive Alkaline-Earth Silicophosphate Glasses", Materials Research Bulletin, pp. 1297-1306, vol. 29, No. 12.
Tilocca et al., "The Structure of Bioactive Silicate Glasses: New Insight from Molecular Dynamics Simulations", 2007, Chem. Mater., pp. 95-103, vol. 19.

* cited by examiner

Fig. 21A
Fig. 21B
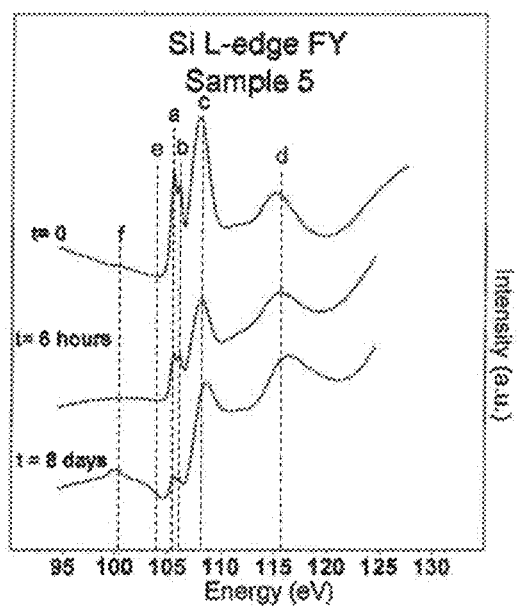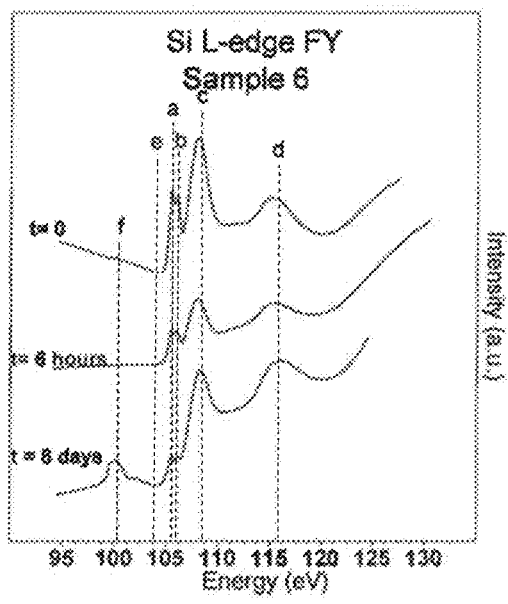

Fig. 28A
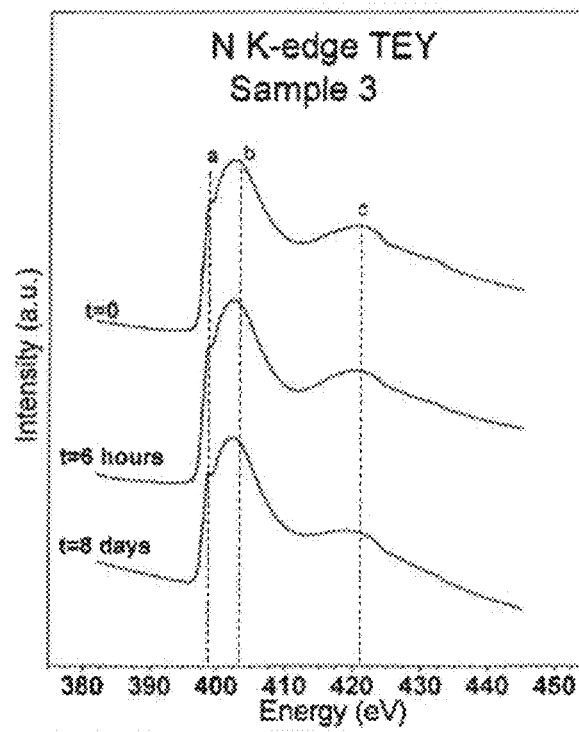
Fig. 28B
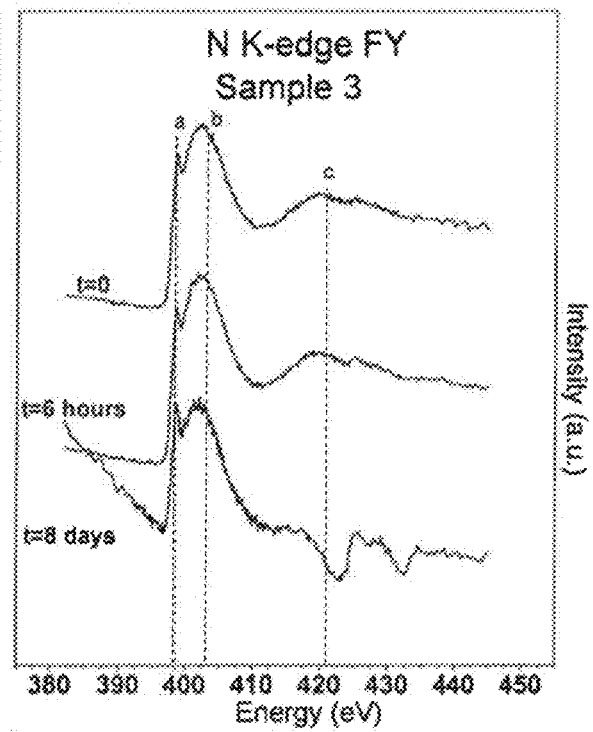
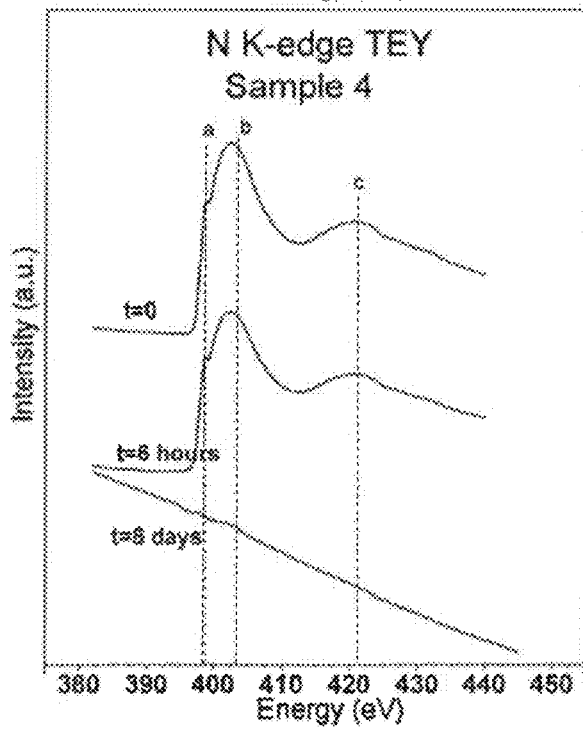
Fig. 28C
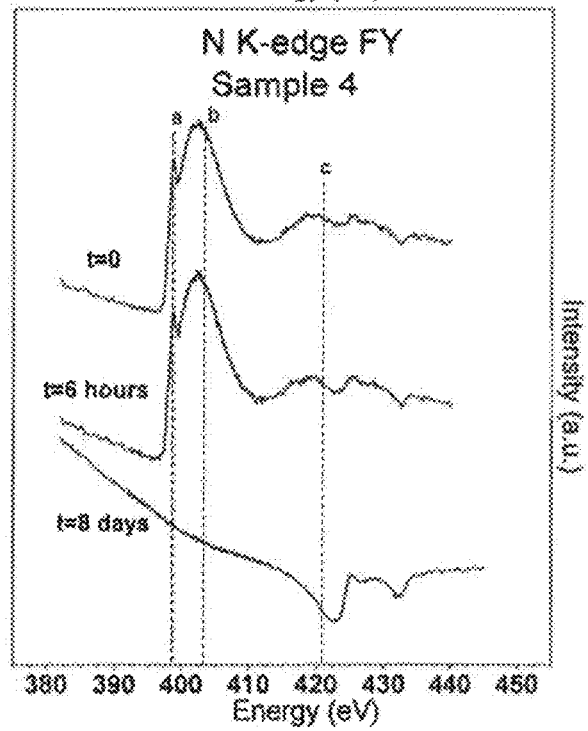
Fig. 28D

Fig. 36A
Fig. 36B
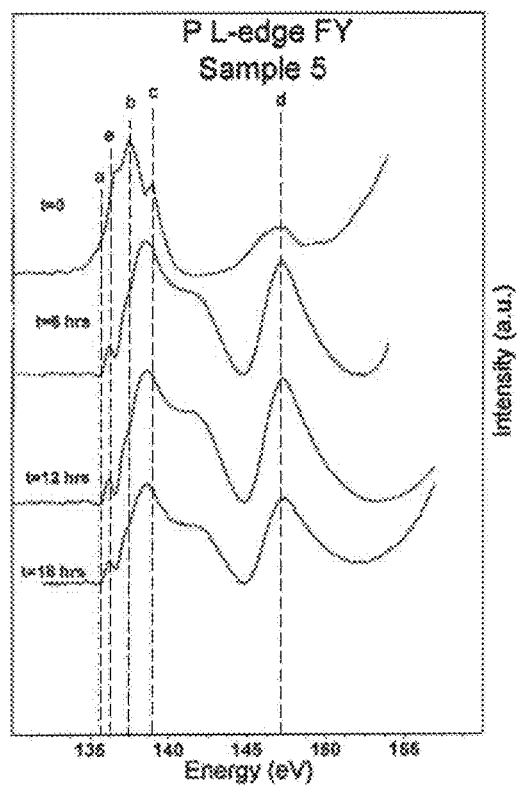
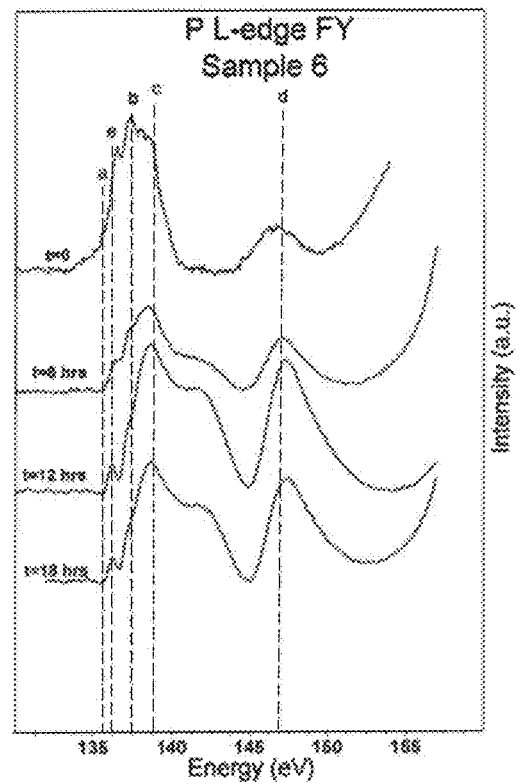

SiONP coated sample

No coatings (control)

Empty defect (control)

| Material | Bioglass | RBM SiONPx (high O content) | RMM SiONPx (high N content) |
|---|---|---|---|
| Stage III | $PO_4^{3-}$  $Ca^{2+}$  $Ca^{2+}$  $Ca^{2+}$  $PO_4^{3-}$  Silica Gel | $PO_4^{3-}$  $Ca^{2+}$  $Ca^{2+}$  $Ca^{2+}$  $PO_4^{3-}$  Silica Gel | $PO_4^{3-}$  $Ca^{2+}$  $Ca^{2+}$  $Ca^{2+}$  $PO_4^{3-}$  Silica Gel |
| Stage IV | $CO_3^{2-}$  $OH^-$  $OH^-$  $OH^-$  $CO_3^{2-}$  Amorphous Ca-P  Silica Gel | $CO_3^{2-}$  $OH^-$  $OH^-$  $OH^-$  $CO_3^{2-}$  Amorphous Ca-P  Silica Gel | $CO_3^{2-}$  $OH^-$  $OH^-$  $OH^-$  $CO_3^{2-}$  Amorphous Ca-P  Silica Gel |
| Stage V | CHA  Silica Gel | CHA  Silica Gel | CHA  Silica Gel |

Fig. 47A    Fig. 47B    Fig. 47C
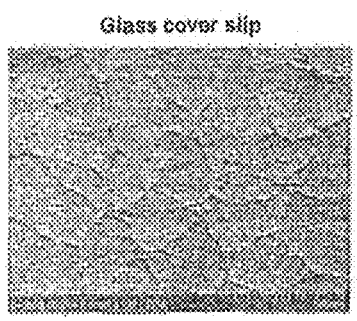 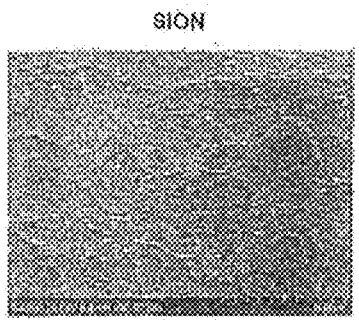 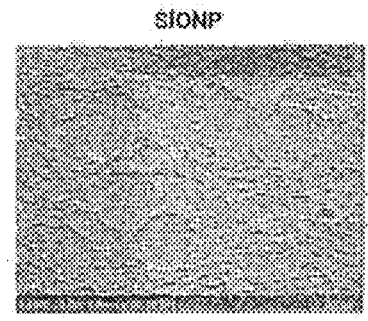
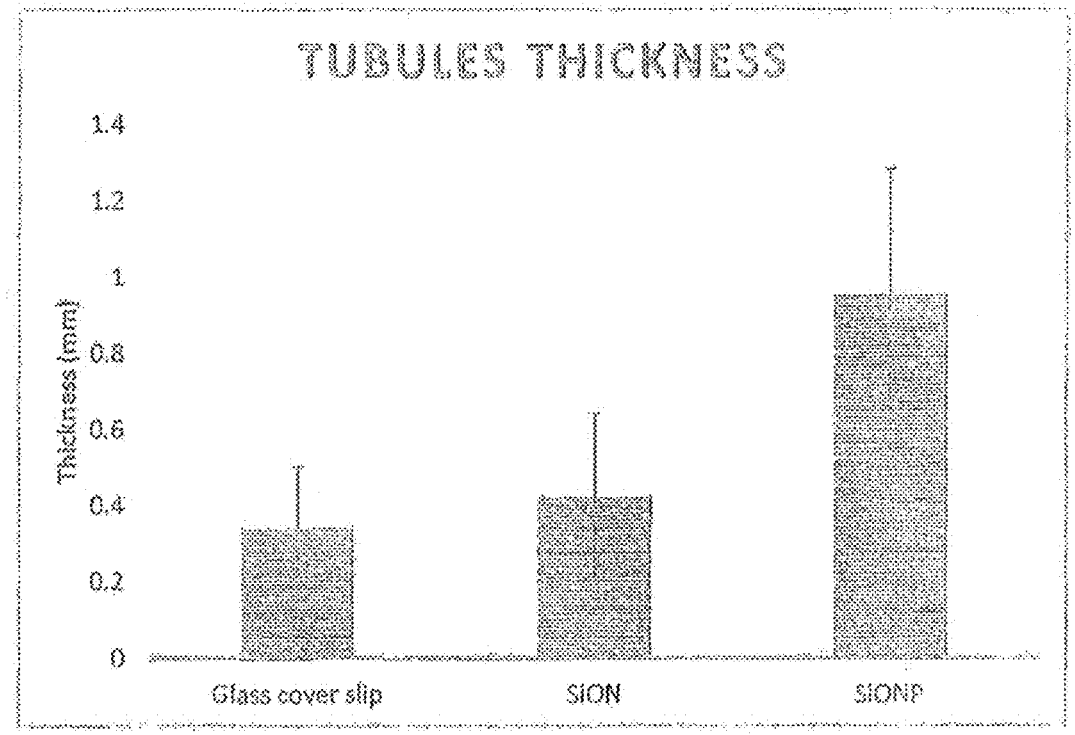
Fig. 47D Fig. 51A
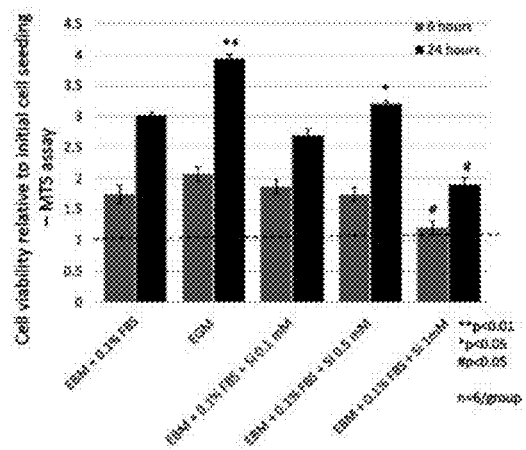
Fig. 51B
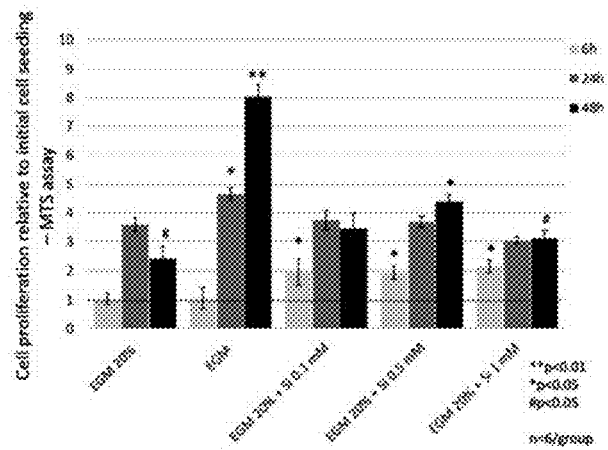
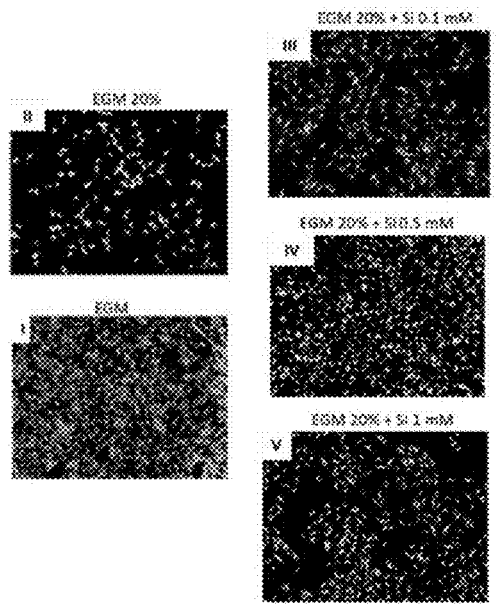
Fig. 51C
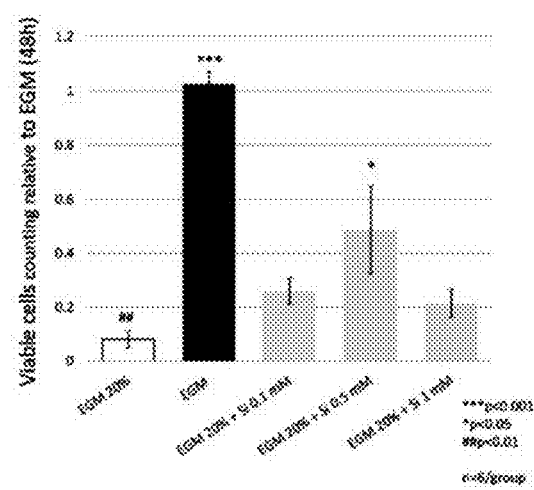
Fig. 51D

**p<0.01
*p<0.05
p<0.001
p<0.05 n=3/group

Fig. 52G
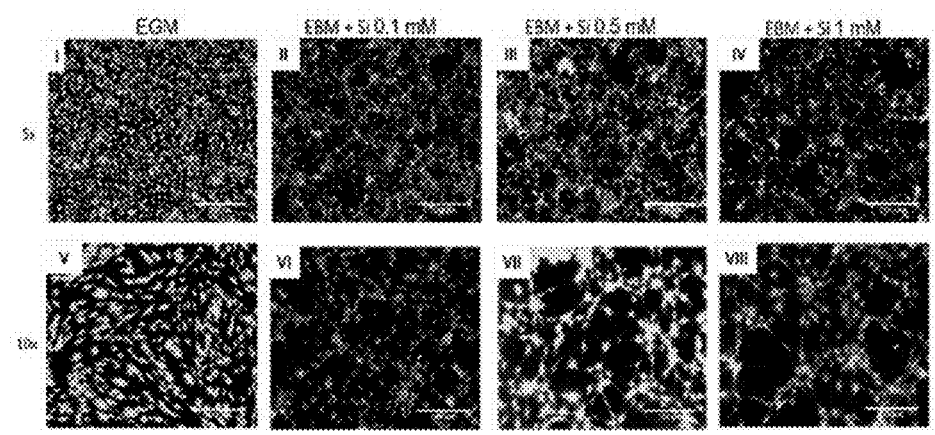
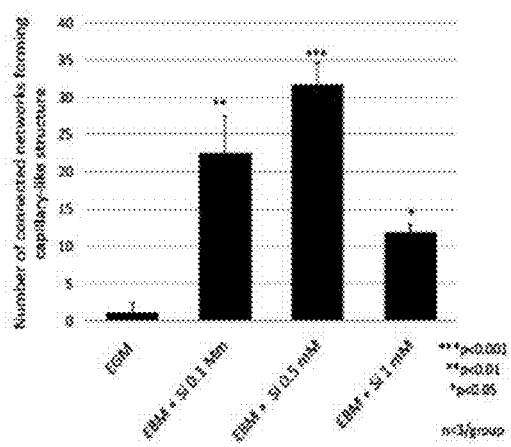
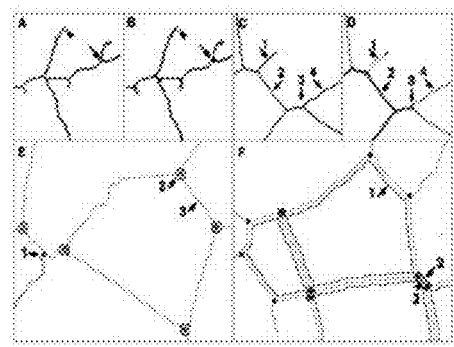
Fig. 52H
Fig. 52I

Fig. 53A
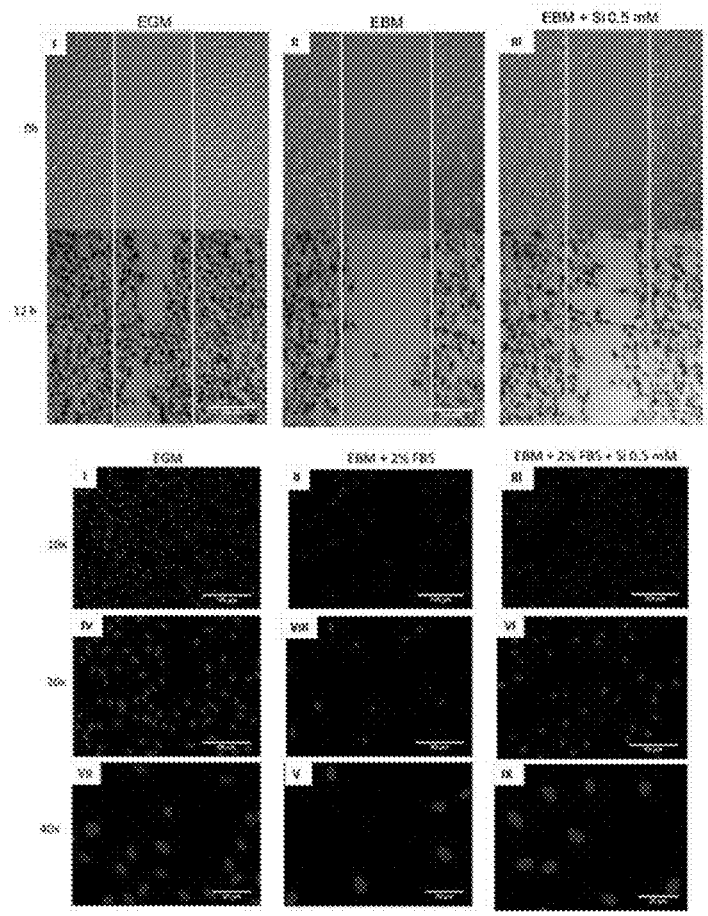
Fig. 53B
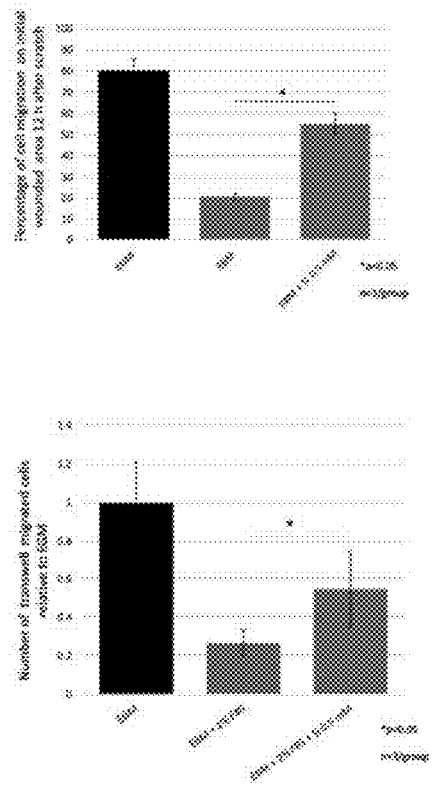
Fig. 53C
Fig. 53D

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Forward PCR Primer for VEGFA

<400> SEQUENCE: 1
tgcggatcaa acctcacca                                                  19

<210> SEQ ID NO 2
<211> LENGTH: 22
<212> TYPE: DNA
<213> ORGANISM: Artificial Sequence
<220> FEATURE:
<223> OTHER INFORMATION: Reverse PCR Primer for VEGFA

<400> SEQUENCE: 2
cagggatttt tcttgtcttg ct                                              22

<210> SEQ ID NO 3
<211> LENGTH: 22
<212> TYPE: DNA
<213> ORGANISM: Artificial Sequence
<220> FEATURE:
<223> OTHER INFORMATION: Forward PCR Primer for VEGFR2

<400> SEQUENCE: 3
gtgatcggaa atgacactgg ag                                              22

<210> SEQ ID NO 4
<211> LENGTH: 23
<212> TYPE: DNA
<213> ORGANISM: Artificial Sequence
<220> FEATURE:
<223> OTHER INFORMATION: Reverse PCR Primer for VEGFR2

<400> SEQUENCE: 4
```

```
catgttggtc actaacagaa gca                                           23

<210> SEQ ID NO 5
<211> LENGTH: 20
<212> TYPE: DNA
<213> ORGANISM: Artificial Sequence
<220> FEATURE:
<223> OTHER INFORMATION: Forward PCR Primer for HIF1-alpha

<400> SEQUENCE: 5
ccatgtgacc atgaggaaat                                               20

<210> SEQ ID NO 6
<211> LENGTH: 20
<212> TYPE: DNA
<213> ORGANISM: Artificial Sequence
<220> FEATURE:
<223> OTHER INFORMATION: Reverse PCR Primer for HIF1-alpha

<400> SEQUENCE: 6
cggctagtta gggtacactt                                               20

<210> SEQ ID NO 7
<211> LENGTH: 20
<212> TYPE: DNA
<213> ORGANISM: Artificial Sequence
<220> FEATURE:
<223> OTHER INFORMATION: Forward PCR Primer for 18S

<400> SEQUENCE: 7
cagccacccg agattgagca                                               20

<210> SEQ ID NO 8
<211> LENGTH: 20
<212> TYPE: DNA
<213> ORGANISM: Artificial Sequence
<220> FEATURE:
<223> OTHER INFORMATION: Reverse PCR Primer for 18S

<400> SEQUENCE: 8
tagtagcgac gggcggtgtg                                               20

<210> SEQ ID NO 9
<211> LENGTH: 19
<212> TYPE: DNA
<213> ORGANISM: Artificial Sequence
<220> FEATURE:
<223> OTHER INFORMATION: Forward PCR Primer for GAPDH

<400> SEQUENCE: 9
gatttggtcg tattgggcg                                                19

<210> SEQ ID NO 10
<211> LENGTH: 17
<212> TYPE: DNA
<213> ORGANISM: Artificial Sequence
<220> FEATURE:
<223> OTHER INFORMATION: Reverse PCR Primer for GAPDH

<400> SEQUENCE: 10
ctggaagatg gtgatgg                                                  17
```

SI—O—N—P RELATED FABRICATION METHODS, SURFACE TREATMENTS AND USES THEREOF

CROSS-REFERENCE TO RELATED APPLICATIONS

The present application claims priority to U.S. Provisional application Ser. No. 62/305,956, filed Mar. 9, 2016. The contents of the provisional application are specifically incorporated herein by reference in its entirety.

FEDERAL GRANT SUPPORT

The work was supported by a grant from National Institutes of Health 1R03DE023872-02. The United States federal government owns rights in the present invention.

FIELD OF THE INVENTION

The present invention relates to the field of surface treatments and/or surface thin-film/nano coatings for medical devices, dental implants and semi-conductor, solar cell, and microelectronic devices. The invention also relates to methods for enhancing osteogenesis, bone generation (formation), fracture healing and wound healing. The invention also relates to the field of medical device surface design and chemical deposition methods.

SUBMISSION OF SEQUENCE LISTING

The contents of the electronic submission of the text file Sequence Listing, which is titled HB521554.16.txt, which was created on May 22, 2017, and is 2.27 KB in size, is incorporated herein by reference in its entirety.

BACKGROUND OF THE INVENTION

Bone fracture incidence from trauma, as well as age-related fragility and/or disorders, contribute to ~$8 B in morbidity/mortality costs and ~800 k procedures annually. It is estimated that the incidence of these medical conditions will continue to rise, especially as life-expectancy increases[1-3].

When fractures occur, the site is structurally unstable and hypoxic due to severe bone loss and ischemia. Inflammation ensues after site re-vascularization, and oxygen metabolites accumulate as reactive oxygen species (ROS: $O^{2-}$, $H_2O_2$). In these fractures, ROS levels can be as much as 8 times that of normal patient levels[4]. An increase in ROS levels has been reported to interrupt bone healing by causing osteoblast DNA damage, apoptosis, and down-regulation of osteogenic differentiation marker expression[5-7]. High ROS levels also create a condition known as oxidative stress. The combination of oxidative stress and site fracture instability leads to a delay in and/or improper bony union[4, 8-12]. Therefore, targeting the prevention and/or inhibition of high ROS levels and oxidative stress, while simultaneously providing structural support at a fracture/trauma site, is vital to ensuring and promoting proper bone healing.

ROS levels must be controlled in order to promote proper fracture healing. Elevated ROS levels may be controlled by increasing available antioxidant enzyme, such as the antioxidant enzyme, superoxide dismutase (SOD1)[13,14]. SOD1 is also very important in stimulating the complex series of biochemical and physiological events needed for bone development and bone healing in vivo. Thus, it was envisioned by the present investigators that an increase in antioxidant enzyme expression would aid the bone healing process, and in particular, osteoprogenitor cell differentiation. It has been reported that without expression of SOD1, osteogenic transcription factors (e.g., osterix (OSX)) can potentially be down-regulated, and result in a reduction in bone strength[6]. However, methods and/or materials that provide for the effective and therapeutic control and/or prevention of destructive high ROS levels through enhancing the generation of anti-oxidants remain lacking in the medical arts.

Another aspect vital to the process of bone regeneration is the process of neovascularization that encompasses vasculogenesis and angiogenesis. Vasculogenesis involves the formation of perfuse blood vessels into the bone fracture or defect site. Angiogenesis refers to the process of vascular reperfusion in which blood vessel walls are solidified. When fractures occur, the site has an initial loss of vasculature. For bone regeneration and fracture repair, the site must form new blood vessels to provide a proper supply of oxygen and nutrients for the site to begin to regenerate. Because the site has a large volume of bone loss and as such a large loss of surface area for blood vessel invasion, the site requires that additional of biomaterials that can both promote vascular invasion and act as a surface to attach blood vessel tubules.

Biocompatibility is a concept that concerns the interaction of a biological system with a foreign material. It has recently been broadly defined by the IUPAC as the ability of a material to perform with an appropriate host response in a specific application.[1] In practice, the application of this definition, the creation of a biomaterial with the ability to perform favorably in a given biological context, requires knowledge of a material-host system on two levels: both the host tissue system and the biomaterial itself must be well understood. This dichotomy lends itself to a two-pronged approach focusing simultaneously on both the host tissue, particularly in the case diseased tissues, and the biomaterial in order to develop biocompatibility in a given host tissue-biomaterial system.

While the exact classification of an appropriate host response to a biomaterial is highly dependent on the type of host tissue system involved, the classification of biomaterial response to a host tissue is somewhat more straightforward. Biomaterials are generally classified into one of four categories: toxic, inert, resorbable, and bioactive.[2]

In the context of bone as the host tissue system the biocompatibility of a biomaterial is defined by the type of bond bone forms with the biomaterial surface. Inert biomaterials do not form a bond with host bone tissue and tend instead to form a fibrous encapsulation in vivo. Resorbable biomaterials degrade in vivo into non-toxic products and are replaced over time by host bone tissue. Though process seems ideal in theory in the sense that it appears to mimic the natural bone remodeling process, in practice it is difficult to control the rate of dissolution of the biomaterial to match the rate of replacement of the host bone tissue. These types of biomaterials are therefore rarely used in load-bearing tissue applications. Bioactive biomaterials form a strong chemical bond with local bone host tissue through a series of chemical reactions at the bioceramics-bone interface that results in the formation of a carbonated apatite layer at the interface surface.[2] This strong interface makes them ideal for use in load bearing bone implant applications such as hip stems and dental screws; however, most bioactive biomaterials used in bone tissue applications—particularly silica-based bioactive glasses—do not have the necessary mechanical strength required to replace load bearing bone.

Bioinert metals like titanium have traditionally been used in load bearing bone implant applications, but they do not bond to local bone tissue and have a finite fatigue life in vivo. Previous attempts to improve the biocompatibility of titanium implants have included the use of bioactive glass coatings. These Ti-bioglass systems generally suffer from the fact that while the bioglass-bone forms a strong interface, the bioglass-Ti interface is much weaker. There is a need, therefore, to explore the possibility of creating a new type of bioactive coating that is capable of forming a strong bond to both host bone tissue and a titanium implant.

Long term clinical success of titanium dental implants is largely a factor of initial bone host tissue response. Recent studies have focused on adapting the surface chemistry, roughness, and topography of titanium[3-5] to enhance the formation of bone around the implant, generally either through the creation of a calcium phosphate-based coating[6] or incorporation of relevant ions like $Ca^{2+}$ and $Mg^{2+}$[7] directly into titanium dioxide. Of particular interest is investigation into early-stage (from 0-3 days) osseointegration.

Current structural materials used to support large missing bone volume do not provide a mechanism whereby deleteriously high levels of ROS can be controlled. Nor do the metal surfaces of these implants foster the formation of an apatite surface layer, an important aspect of the bone formation process. Thus, while metal implants (e.g., titanium [Ti]) are useful as structural materials for bone implant because of their strength, they suffer the disadvantage of long healing times[15].

Hydroxyapatite and calcium phosphate-based coatings have also been used with bone implants to foster surface bone attachment to the implant. However, while these materials do provide for the formation of a surface hydroxyapatite layer, they unfortunately fail to provide stable, strong bone attachment because of the large coefficient of thermal expansion mismatch with the underlying metal. This thermal expansion mismatch problem results in resorption and delamination of the bone from the metal surface of the implant, and ultimately failure of the implant attachment[16]. In addition, these coatings fail to provide a solution to the damaging effects of high ROS levels, so common to the physiological environment of an implant site in vivo.

Synthesis routes for synthetic hydroxyapatite overlay cause inhomogeneity in the coating and have thermal expansion mismatch with the underlying Ti, leading to delamination and instability of the coating[1]. Bioactive glass coatings, which are modified from commercially available bioglass with added MgO for improved thermal expansion matching, have shown a drawback to down-regulate important osteogenic markers associated with bone formation due to $Mg^{2+}$ release[2].

Attempts to strengthen the amorphous silica network have involved the addition of nitrogen (N) as a constituent to the SiOx network. The addition of N changes the tetrahedrally coordinated network into one that is a combination of tetrahedral and trigonal[13]. Incorporation of N (through annealing with $N_2$ gas) into the amorphous silica-based bioactive glass matrix improved its mechanical strength[14]. This also strengthened amorphous silica-based bioactive glass-Ti interface. However these coating are limited in that they can only be applied by enameling, which has a large coating to interface thickness ratio (1000:1), leaving them more susceptible to delamination[15]. Sputter coated silicon oxynitride films have also been studied for their mechanical properties and showed a linearly increasing strength with N content[13]. Beyond its effect on SiOx mechanical strength, the effect of adding N on biomineralization and cells' response to Si(ON)x surfaces are still unknown. Bio-inspired surface topographies at nano and micrometer scales are known to influence cellular behaviors such as cell adhesion, migration, differentiation and growth[16-19], with moderately rough surfaces (1-2 μm) showing stronger bone responses than smoother or rougher surfaces[19]. Oral implants also have moderately rough surfaces that permit bone ingrowth into minor surface irregularities, promoting osseointegration[19] while a bioactive coating can add biochemical bonding with biomechanical bonding of these oral implants.

The natural degradation of a SiO2, Si3N4, and/or Si(ON)x-based film and/or nanofilm at a surface results in the release of ionic silicon (such as $Si^{4+}$). Increasing the availability of free ion, such as ionic silicon, at the site of, for example, a bone implant and/or dental implant, facilitates more rapid healing and bone attachment, at least in part, by reducing levels of reactive oxygen species ($ROS: O_2^-, H_2O_2$) in an in vitro or in vivo environment comprising osteoblasts, among other things. The formation of a mineralized tissue on the treated surface results, thus providing a site of attachment for bone, and a more secure bone-device connection that promotes healing and bone formation.

With the rise of permanent and semi-permanent osseoimplants, the need for a material that reacts favorably and adheres well to the in vivo bone environment has become increasingly critical. Bioglass, generally composed of $SiO_2$, $Na_2O$, CaO, and $P_2O_5$ in various proportions, is well-known to form a layer of apatite on the glass-tissue interface[87] and thus avoid problems associated with fibrous encapsulation that had previously been noted around less biocompatible implant surfaces.[32] Bioactive glasses, however, cannot be used in load-bearing osseoapplications. More recent work on bioactive glasses has looked at modifying their chemical structure with MgO and $K_2O$ to create a chemistry that can be coated on Ti and form a bond at both the metal-glass and glass-bone interfaces and therefore be used to coat the titanium implants that are used in load-bearing applications.[71-73, 110] While these glasses represent an improvement in terms of $TiO_2$-glass bonding, $Mg^{2+}$ has recently been shown to delay mineralization and partially down regulate osteoblast markers in combination with $Si^{4+}$ and $Ca^{2+}$.[111] This flexibility and alteration of chemistry leads to a treatment of bioactive glasses from an elemental perspective.

From an elemental standpoint, interface reactions based on the release and exchange of the primary cations in bioactive glasses—Si, Ca, P, and Na ions—are known to promote favorable cellular responses and rapid osseointegration.[34, 111, 138] $Si^{4+}$ and $Ca^{2+}$ in particular have been shown to enhance osteoblast markers in vitro. [139] Phosphate-free glasses, on the other hand, have also been shown to exhibit bioactivity, leading to the theory that the primary role of phosphate in these glasses is in lowering the energy barrier to nucleation of apatite on the surface.[41] This observation naturally leads to a question of some complexity: what reactions (in what local concentrations) are necessary to form an apatitic layer that can then form a strong bond to bone mineral tissue? From the sheer quantity of patented bioactive glass formulations, it is evident that there is some flexibility in terms of glass chemistries that allow for apatite formation under physiological conditions.

Bioactive glasses, which are generally formed from a mixture of $SiO_2$, $Na_2O$, CaO, and $P_2O_5$, bond to bone in vivo through the formation of carbonated hydroxyapatite layer.[87] The exact mechanism involves five basic steps: (1) First, there is a rapid exchange of cations ($Na^+$ or $Ca^{2+}$) with $H^+$ from the physiological environment which results in the formation of silanol bonds (Si—OH) on the glass surface. The local pH of the dissolving environment increases and a silica-rich layer forms near the exposed glass surface. Phosphate ions ($PO_4^{3-}$) are also lost from the surface region during this step. (2) The high pH leads to the breakdown of the silica network via Si—O—Si bond attack by hydroxide ions (OH). The soluble silicon ($Si^{4+}$) is lost in the form of $Si(OH)_4$ which again results in Si—OH bonds at the glass surface. (3) These silanol groups condense to form a silica-rich layer at the glass surface. (4) Calcium $Ca^{2+}$ and phosphate ions $PO_4^{3-}$ start to migrate through this surface layer to form an amorphous film of calcium oxide CaO and phosphate on the silica-rich layer. (5) Hydroxyl ($OH^-$) ions and carbonate ions ($CO_3^{2-}$) from the environment begin to incorporate within the Ca—P layer to form a carbonated apatite.

Though this process has been observed in vivo, the same process also occurs in bioactive glasses when immersed in a simulated body fluid (SBF) solution where ionic salt concentrations are roughly equivalent to those of human blood plasma.[88] SBF can be prepared via the dissolution of inorganic compounds in water that is buffered to a pH of ~7.4. Alpha minimum essential media, αMEM, which is commonly used in cell culture experiments, can also be used as a simulated body fluid since its composition is also similar to the salt concentrations of human blood plasma.

A need remains in the medical arts for improved materials useful for medical device and other device fabrication that supports and/or enhances all of the biological processes associated with healing, including vascularization and structural formation of the cellular elements associated therewith, such as microtubules.

SUMMARY OF THE INVENTION

The present invention provides a solution to the above and other medical and/or clinical needs. This invention provides new chemistry for implant coatings (thin films) to increase the usability of metal dental and orthopedic implants for patients afflicted with disorders involving soluble bone formation. These coatings use a Si—O—N—P elemental chemistry to provide sufficient insoluble mineral chemistries that promote the rapid formation of bone in both healthy and disordered bone. Applicants have found that the presence of an intrinsic phosphate concentration promotes rapid formation of bonelike hydroxyapatite formation within a few hours without the aid of osteoblast cells or bone. Hydroxyapatite is the mineral component of bone and this is needed to provide a sturdy substrate for bone regeneration in insoluble bone disorders. In addition, these coatings could also be used for implants to promote rapid regeneration of bone for healthy patients suffering from bone fractures.

In some aspects, the invention provides for a device or other implement that includes (comprises) at least one treated surface having a composition comprising a phosphorous-doped silicon oxynitride. In particular embodiments, the treated surface comprises an amorphous, stoichiometric, non-stoichiometric, or crystalline silicon oxynitrophosphide ($Si_zO_xN_yP_w$) layer. The treated surface may be composed of a metal, ceramic, polymer, glass or composite hybrid material of metal, ceramic, polymer or glass. Further, the device or other implement may be described in some embodiments may be described as a load-bearing, non-load bearing or low load bearing device. By way of example, the load-bearing device may be a medical implantable device, such as an implantable support member needed in bone repair of a long bone, such as a tibia.

The treated surface may be prepared according to any number of methods, one particular method that may be used for deposition of a desired composition employs a PECVD process using a silicon based reagent and PH3 to provide phosphorous-doped silicon oxynitride deposition on the desired surface. Once deposition has been completed, the treated surface may be described as comprising a phosphorous-doped silicon oxynitride, and more particularly, an amorphous phosphorous-doped silicon oxynitride.

The devices and other implements of the present invention may be described as comprising a treated surface that includes a composition having a nanoscale thin film, the nanoscale thin film having a thickness of about 1 nm to about 999 nm. In other embodiments, the composition of the treated surface may be described as having a micro-scale thin film having a thickness of about 0.001 mm to about 0.999 mm.

In some embodiments, the treated surface may be described as having a deposition of phosphorous-doped silicon oxynitride defined by a formula SiONPx.

In some embodiments, the specific composition may be defined by reference to a Random Bonding Model (RBM), utilizing the formula $Si_zO_xN_yP_w$, where the "z", "x" "y" and "w" equals 1. In the RBM, nitrogen is considered to incorporate into the basic silicon dioxide tetrahedral network and form a chemistry of the form $Si_zO_xN_yP_w$. In a particular embodiment, the $Si_zO_xN_yP_w$ is $Si_{2.27}O_{1.58}N_{0.13}P_{0.018}$. The RBM would form an elemental chemistry of the form $Si_zO_xN_yP_w$, where the "z", "x" "y" and "w" equals 1.

In other embodiments, the thin film of the treated surface is defined as comprising a composition that may be defined by reference to a Random Mixing Model (RMM). The RMM states that a non-stoichiometric silicon oxynitride can be treated as a simple mixture of a-Si—P, SiO2P, Si3N4P, and P2O5[112].

The devices and other implements of the invention may also be described as having a treated surface with a thin film that comprises about 0.2 atomic % to about 1.5 atomic % of P, about 55 atomic % to about 65 atomic % of Si, about 2.0 atomic % to about 34.0 atomic % of N, and about 1.0 atomic % to about 40 atomic % O, in a phosphorous-incorporated silicon oxynitride coating. In some embodiments, the treated surface comprises a thin film having about 55 atomic % to about 65 atomic % of Si in a phosphorous-incorporated silicon oxynitride coating. In other embodiments, the treated surface comprises a thin film having about 0.2 atomic % to about 0.5 atomic % of P in a phosphorous-incorporated silicon oxynitride coating. In yet other embodiments, the treated surface comprises a thin film of about 1 atomic % to about 45 atomic % of O in a phosphorous-incorporated silicon oxynitride coating.

In some embodiments, the treated surface may be described as having a phosphorous-doped silicon oxynitride having a composition of: (a) 3.2% SiO2-37.7% a-Si-58.9% Si2N4-0.24% P2O5, (b) 6.3% SiO2-39.6% a-Si-53.8% Si2N4-0.25% P2O5, (c) 11.0% SiO2-35.4% a-Si-53.4% Si2N4-0.28% P2O5, (d) 21.27% SiO2-31.5% a-Si-46.9% Si2N4-0.27% P2O5; (e) 2.28% SiO2-1.54% a-Si-0.16% Si2N4-0.015% P2O5; or (f) 2.27% SiO2-1.58% a-Si—0.13% Si2N4-0.018% P2O5.

In another aspect, a device is provided that may comprise at least one treated surface comprising multiple or stacked layers of silicon-based thin films, wherein the thin films are deposited by a PECVD deposition process to provide one or more treated surfaces having a phosphorous-doped silicon oxynitride thin film.

The device or other implement of the invention may comprise a medical device (for example, a bone implant, screw or other dental, orthopedic, calvarial or tibial device), a semi-conductor, a solar cell or micro-electronics device.

In another aspect, the devices may be described as providing a treated surface that enhances neovascularization to the treated surface, thus providing for an increase in vasculogenesis and angiogenesis to the treated surface, compared to a surface not treated with a composition comprising the phosphorous-doped silicon oxynitride.

Method of Fabrication:

In yet another aspect, methods are provided for preparing a surface of a device or other implement to include a Si—O—N—P layer. In some embodiments, the method comprises providing a cleaned surface; depositing an amorphous SiONPx thin film overlay on said cleaned surface using a chemical vapor deposition system with plasma enhancement in the presence of a silica-based reagent, wherein said chemical vapor deposition system is a Si—O—N—P chemical deposition system comprising a source of silicon, oxygen, nitrogen, and phosphorous, wherein said silica-based reagent comprises $SiH_4$, $Si(OC_2H_5)_4$, or a combination thereof; providing a treated surface having a thin film amorphous stoichiometric Si—O—N—P layer, wherein said treated surface provides for release of Si-ion at said treated surface.

In some embodiments, the method of fabrication for forming a SiONPx layer onto a surface to provide a treated surface employing a PECVD method, may be described as comprising: providing a source of gas reagents in a mixture of 15% silane ($SiH_4$)/2% phosphine ($PH_3$)/83% argon (Ar) (15%/2%/83%) (24 sccm), nitrous oxide ($N_2O$), nitrogen ($N_2$), and ammonia ($NH_4$).) at the indicated ratios in Table 6, at the surface to be treated, increasing temperature at the surface to between about 100-500 C (below the glass transition temperature of amorphous silica) to provide an SiONPx deposit on said surface, and lowering pressure to between about 0.1 to about 100 Torr at the surface sufficient to maintain a vacuum and induce plasma formation at the surface, and forming an SiONPx film on said surface so as to provide a treated surface having a SiONPx film. The reaction of the formation of the SiONPx film occurs on the substrate surface to form the film. Spent reagent gases are trapped in a Ti pump and captured and removed in appropriate waste containers.

The specific chemical composition of the film layers may be manipulated by modification of the amounts/ratios of the source gasses used in the deposition process.

In some embodiments, the silica-based reagent comprises SiH4 or Si(OC2H5)4.

The surface to be treated may comprise a metal, ceramic, a biopolymer, or a composite material of a composite of a metal, ceramic and biopolymer.

Method of Enhancing Vascularization to a Surface:

In yet another aspect, a method for enhancing vascularization at a surface is provided. In some embodiments, the method comprises providing a surface with an amorphous SiONP coating using a PECVD method to provide a treated surface comprising a coating of an elemental Si—O—N—P, wherein said coating comprises phosphorous-doped silicon oxynitride; providing a population of cells comprising cells suitable for vascularizing a surface to said treated surface to provide a vascularization at said surface, wherein cellular vascularization at said treated surface is enhanced over vascularization at a surface not having an amorphous SiONP coating.

Modified/Stacked Treated Surfaces and Devices:

In some embodiments, the treated surface is a nano-grooved surface. In particular embodiments, the treated surface may be described as comprising a nano-scale film of phosphorous-doped silicon oxynitride. The treated surface may comprise a metal surface, a ceramic surface, or a biopolymer surface.

The devices and implements described may include any particular of In particular those embodiments, where 1 wherein the treated surface comprises a nanoscale amorphous SiONP coating having a nano-film thickness of about 1 nm to about 999 mu or a micro-film thickness of about 0.001 mm to about 0.999 mm.

The treated surface may comprise a phosphorous-incorporated silicon oxynitride coating, said coating comprising about 0.2 atomic % to about 1.5 atomic % of P in a phosphorous-incorporated silicon oxynitride coating. In some embodiments, the treated surface is a titanium surface comprises about 0.2 atomic % to about 0.5 atomic % of P in a phosphorous-incorporated silicon oxynitride coating. In other embodiments, the treated surface comprises a phosphorous-incorporated silicon oxynitride coating, said coating comprising: about 0.2 atomic % to about 1.5 atomic % of P in a phosphorous-incorporated silicon oxynitride coating; about 55 atomic % to about 65 atomic % of Si in the phosphorous-incorporated silicon oxynitride coating; about 3.0 atomic % to about 35.0 atomic % of N in the phosphorous-incorporated silicon oxynitride coating; and about 1 atomic % to about 45 atomic % of 0 in the phosphorous-incorporated silicon oxynitride coating.

The methods for preparing the treated surfaces may be via etching by optical or electron-beam lithography to provide a patterned treated surface, wherein said patterned treated surface comprises a grooved, pegged, or other topical surface pattern, and wherein said patterned treated surface is a nano-film having a thickness of about 1 nm to about 999 nm, or a micro-scale thin film having a thickness of about 0.001 mm to about 0.999 mm.

The devices provided may also comprise at least two treated surfaces to provide a multiple stacked construct, wherein at least two of the treated surfaces comprise phosphorous-doped silicon oxynitride. In some of these embodiments, the multiple stacked construct may comprise at least two treated surfaces that include a layer of $SiO_x$, $SiON_x$, SiONP, or any combination of a $SiO_x$, $SiON_x$, and $SiONP_x$ layers. The multiple stacked construct may be described as comprising a series of treated surfaces that have a configuration of (1) $SiO_x$—$SiON_x$—SiONP, (2) Si—$O_x$—SiONP, (3) $SiON_x$—$SiONP_x$; or any combination of these types of treated surfaces or multiples thereof.

Various modifications and other embodiments of the invention are also contemplated and anticipated to be within the spirit and scope of the present invention, and the examples provided herein are not intended to limit the scope or application of the invention.

DESCRIPTION OF THE SEVERAL VIEWS OF THE DRAWINGS

FIG. 21A—Silicon L-edge XANES FY spectra of Sample 5 and FIG. 21B of Sample 6 high-oxygen content SiONPx coating chemistries at t=0, 6 hours, and 8 days (a) and (b) indicate silica tetrahedral structure (c) and (d) indicate $Si^{4+}$ (e) indicates Si—N bonding and (f) indicates the presence of Si—Si bonding.

FIGS. 28A and 28B—Nitrogen K-edge XANES TEY and FY spectra of Sample 3 and FIGS. 28C and 28D of Sample 4 intermediate nitrogen and oxygen SiONPx coating chemistries showing (a) the presence of 2-fold coordinated nitrogen.

Figure 33:
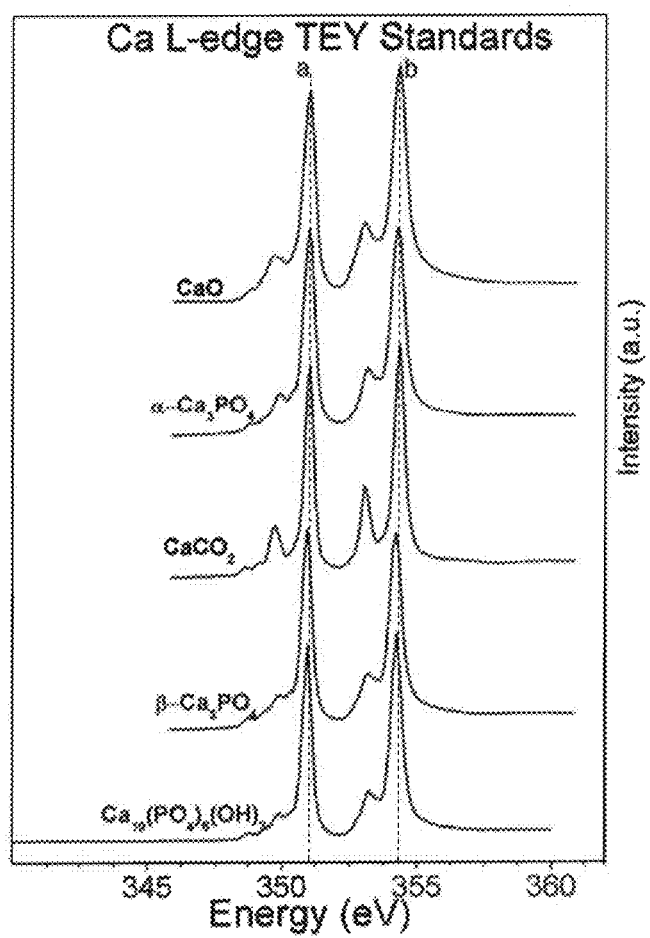

FIG. 33—Ca $L_{2,3}$-edge XANES TEY spectra of some possible calcium precipitate standards showing main (a) and (b) Ca L2 and L3 edges with pre-edge features.

Figure 34A:
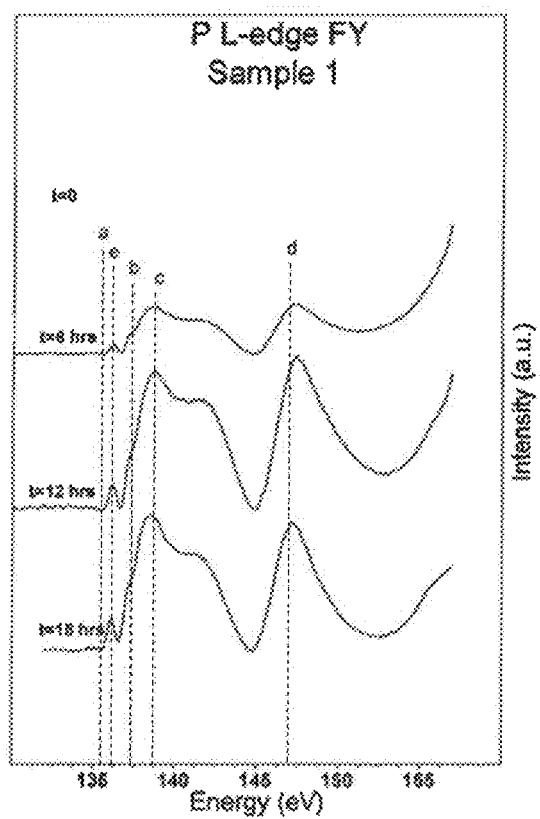
Figure 34B:
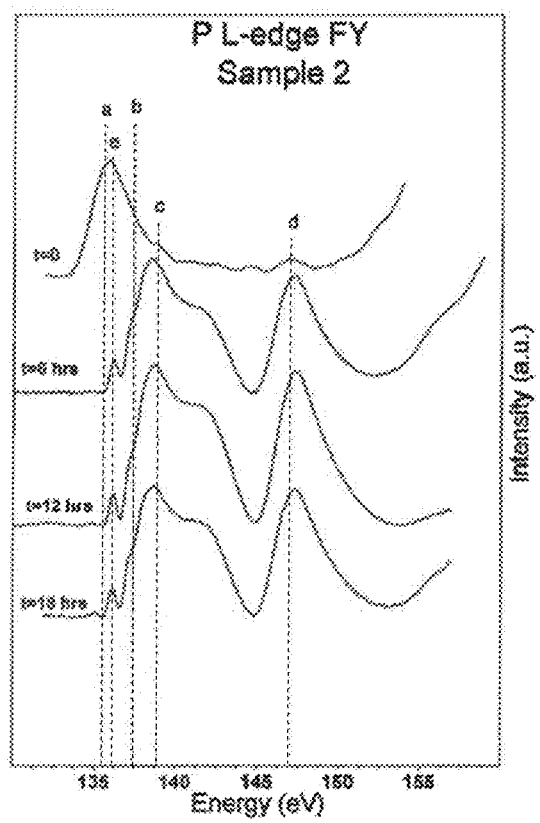

FIG. 34A-P $L_{2,3}$-edge XANES FY of Sample 1 and FIG. 34B of Sample 2 SiONPx coating chemistries at t=0, 6, 12, and 18 hours peaks (c) and (d) show precipitation of phosphate species on the samples after 6 hours in solution.

Figure 35A:
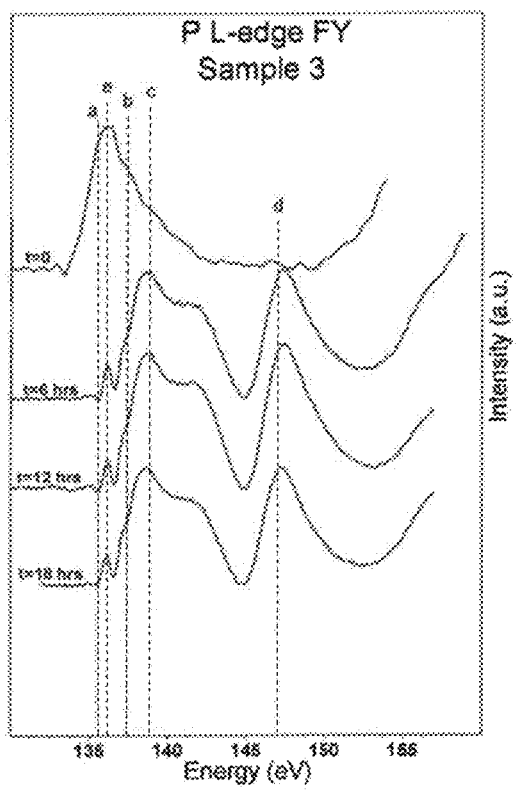
Figure 35B:
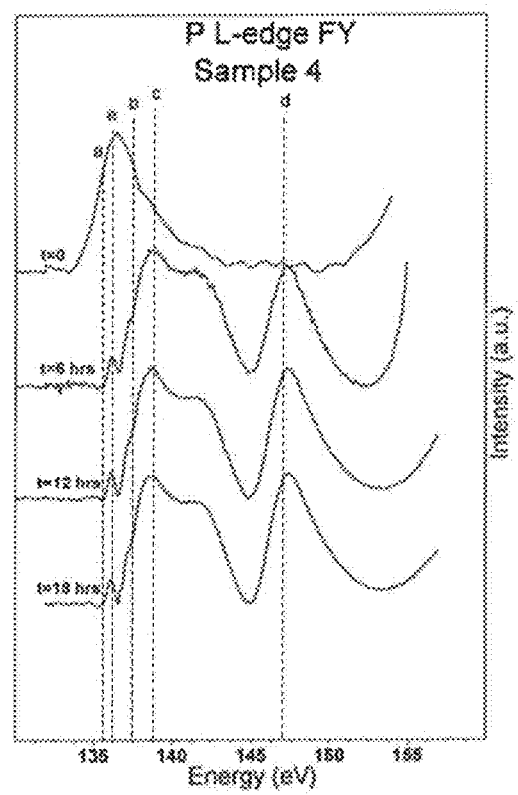

FIG. 35A-P $L_{2,3}$-edge XANES FY of Sample 1 and FIG. 35B of Sample 2 SiONPx coating chemistries at t=0, 6, 12, and 18 hours peaks (c) and (d) show precipitation of phosphate species on the samples after 6 hours in solution FIG. 36A-P $L_{2,3}$-edge XANES FY of Sample 1 and FIG. 36B of Sample 2 SiONPx coating chemistries at t=0, 6, 12, and 18 hours peaks (c) and (d) show precipitation of phosphate species on the samples after 6 hours in solution.

Figure 37:
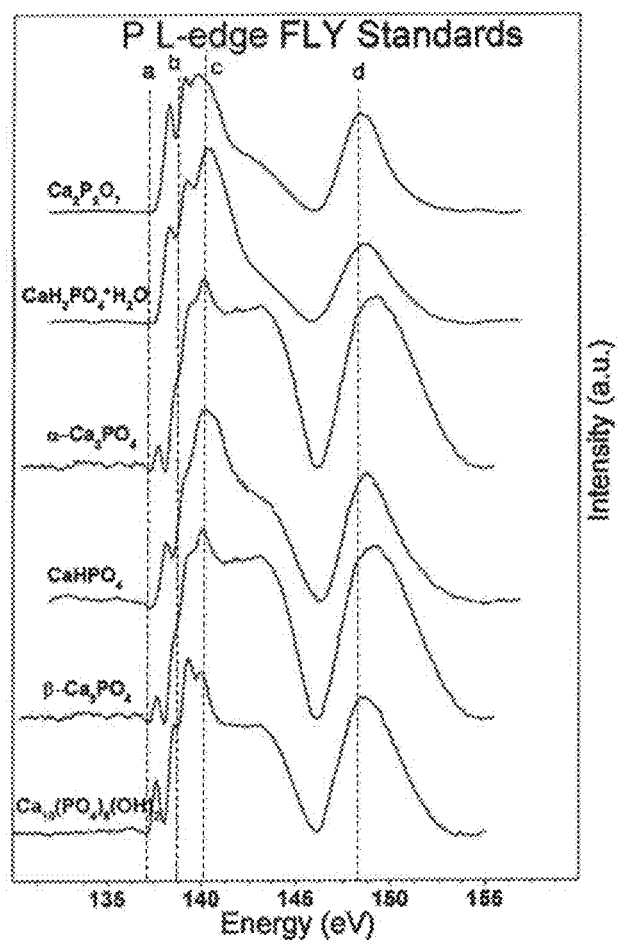

FIG. 37—P $L_{2,3}$-edge XANES FLY spectra of some possible calcium phosphate precipitate standards with well-defined peak (a) and (b) spectral features.

Figure 38A:
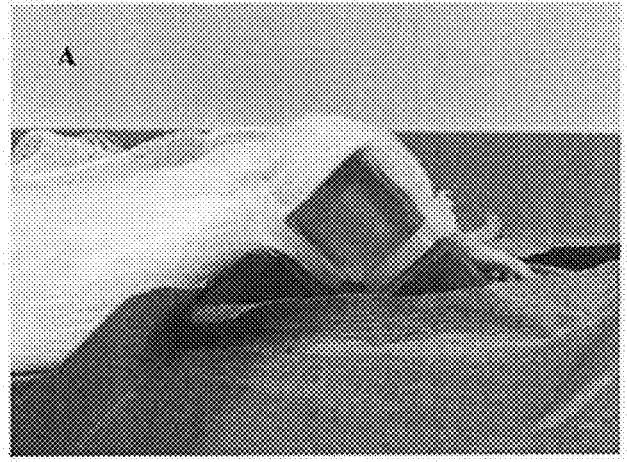
Figure 38B:

FIG. 38A—placement of rat leg on the triangular support; FIG. 38B—placement of the rod inside the tibia by transpatellar tendon approach. Animal after sacrifice used for other study.

Figure 39:
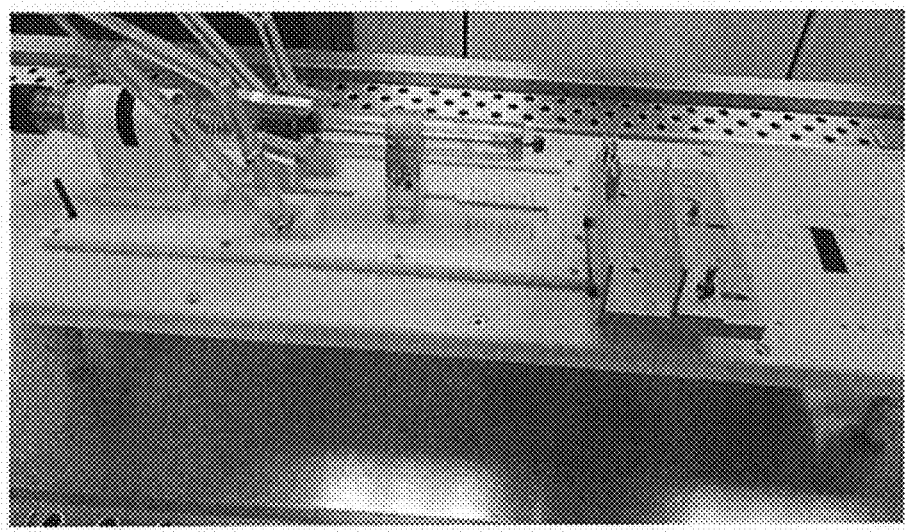

FIG. 39—Guillotine like apparatus to provoke the fracture.

Figure 40:
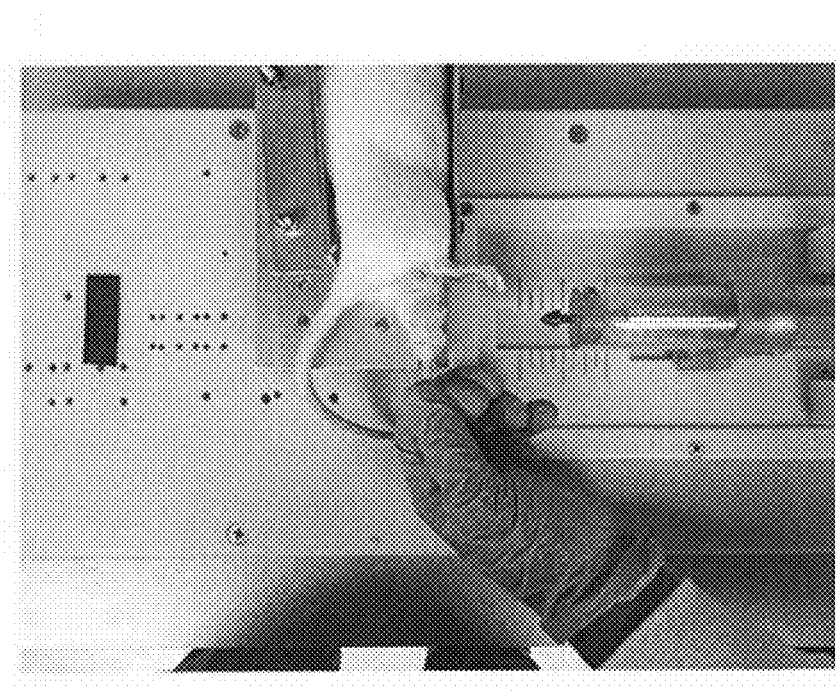

FIG. 40—Animal positioned on apparatus support and held with zip tight. Animal after sacrifice used on other study.

Figure 41A:
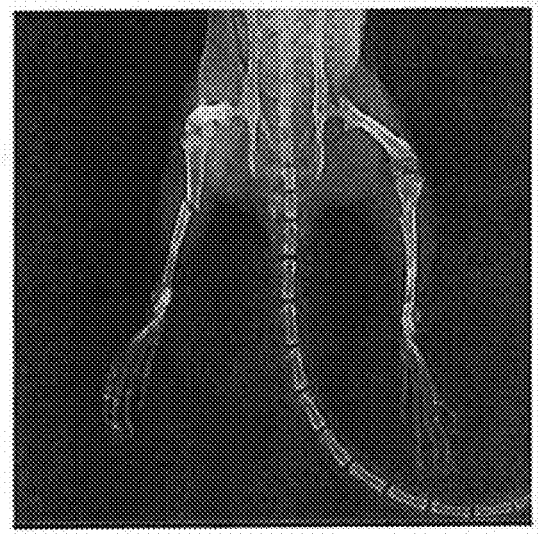
Figure 41B:
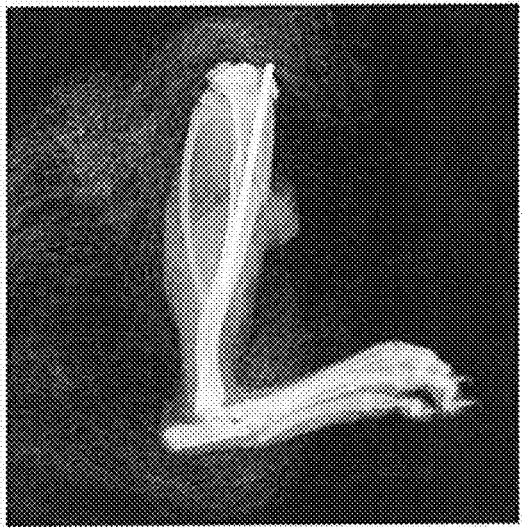

FIG. 41A—The picture above shows the X-ray image of tibia fracture induced by guillotine like device without rod (left) and FIG. 41B X-ray image with rod (right). Animal after sacrifice used for other study.

Figure 42A:
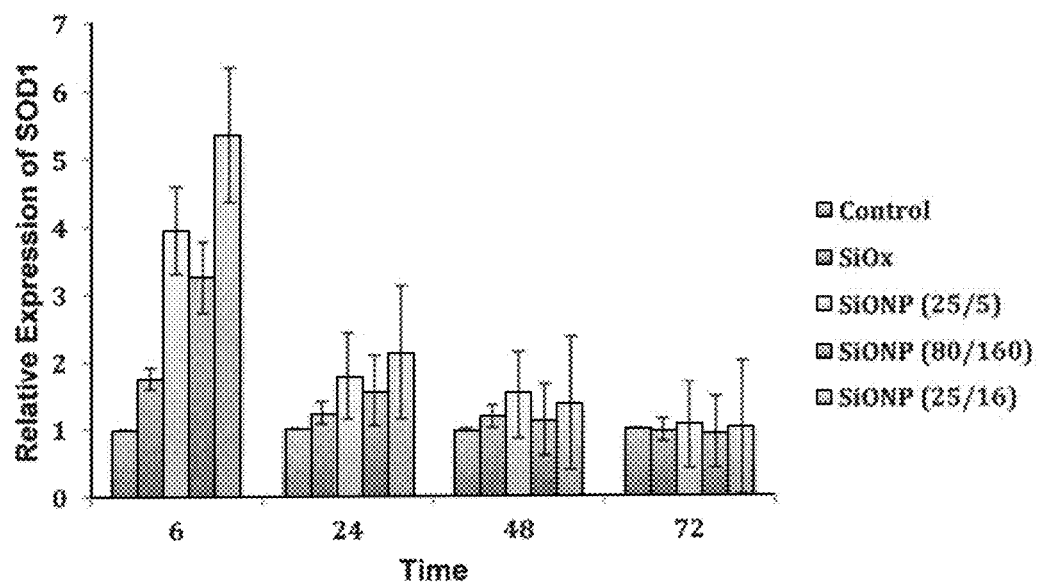

FIG. 42A—Relative expression of SOD1 onto SiOx and SiONP surfaces at 6 hours, 24 hours, 48 hours, and 72 hours.

Figure 42B:
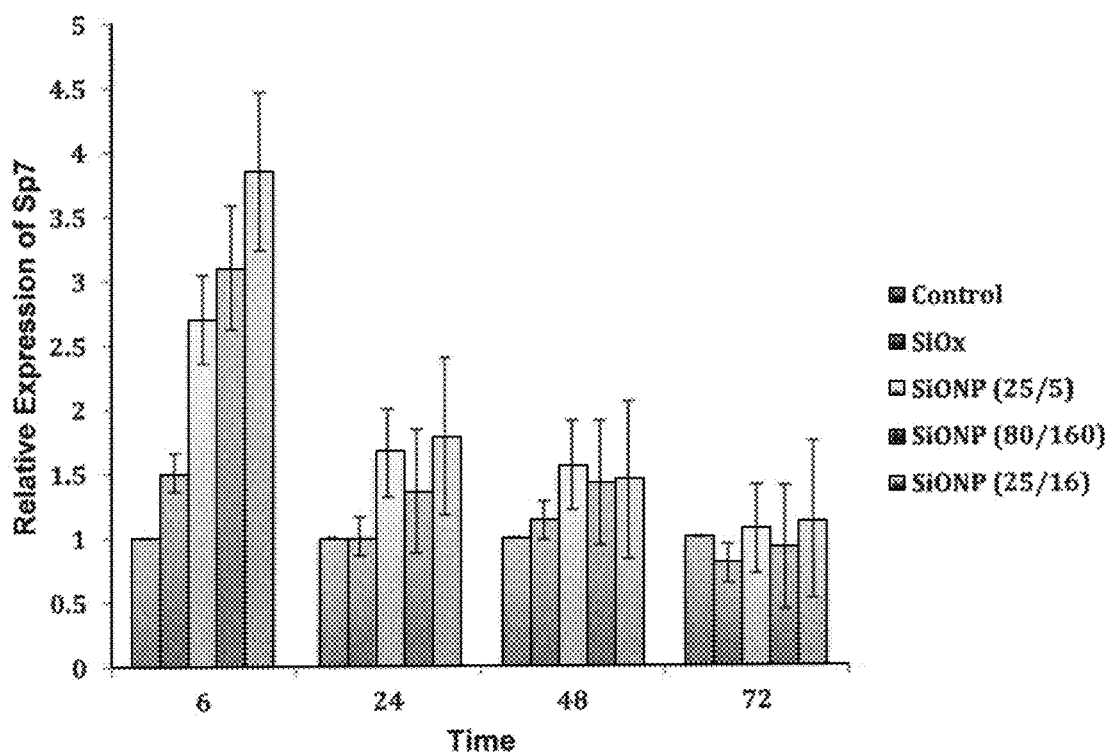

FIG. 42B—Relative expression of Sp7 onto SiOx and SiONP surfaces at 6 hours, 24 hours, 48 hours, and 72 hours.

Figure 42C:
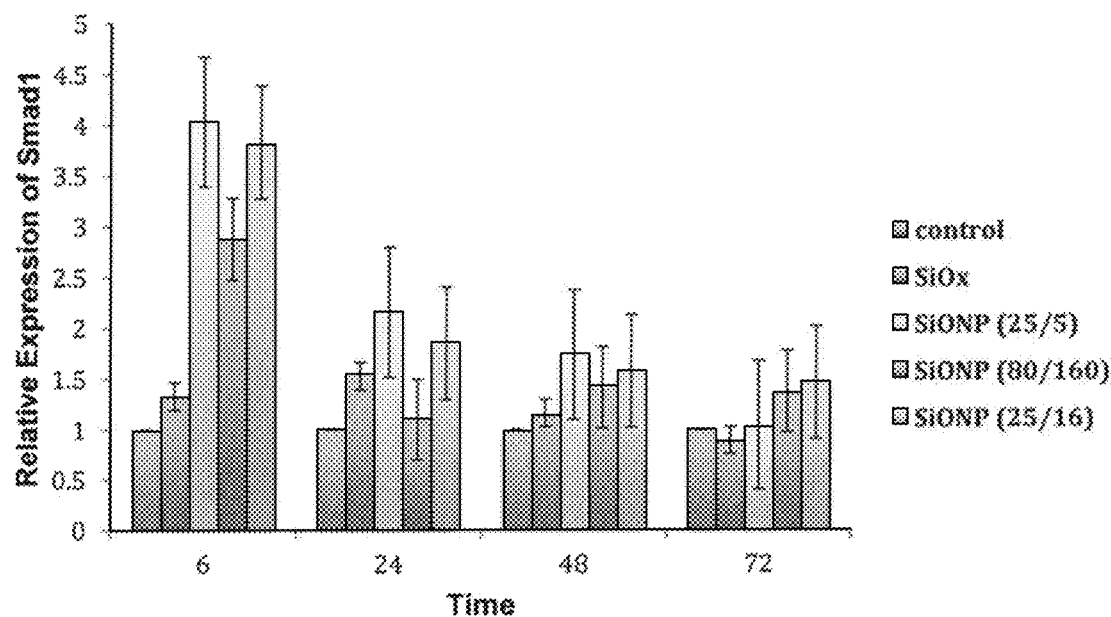

FIG. 42C—Relative expression of Smad1 onto SiOx and SiONP surfaces at 6 hours, 24 hours, 48 hours, and 72 hours.

Figure 42D:
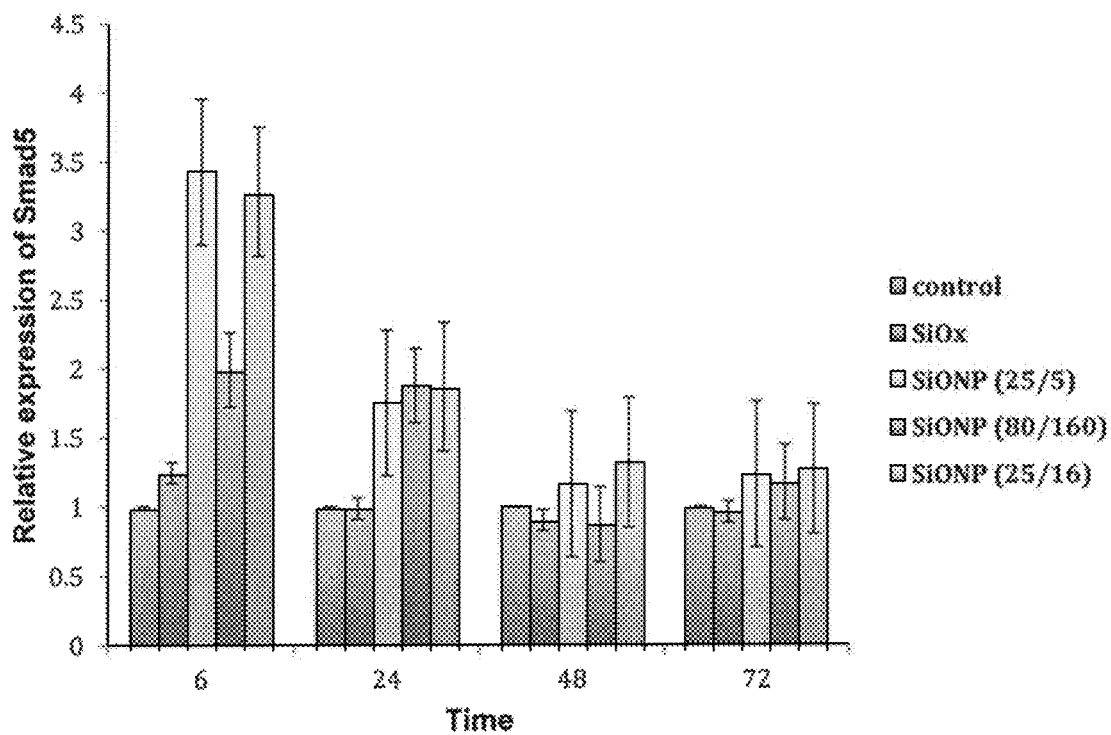

FIG. 42D—Relative expression of Smad5 onto SiOx and SiONP surfaces at 6 hours, 24 hours, 48 hours, and 72 hours.

Figure 42E:
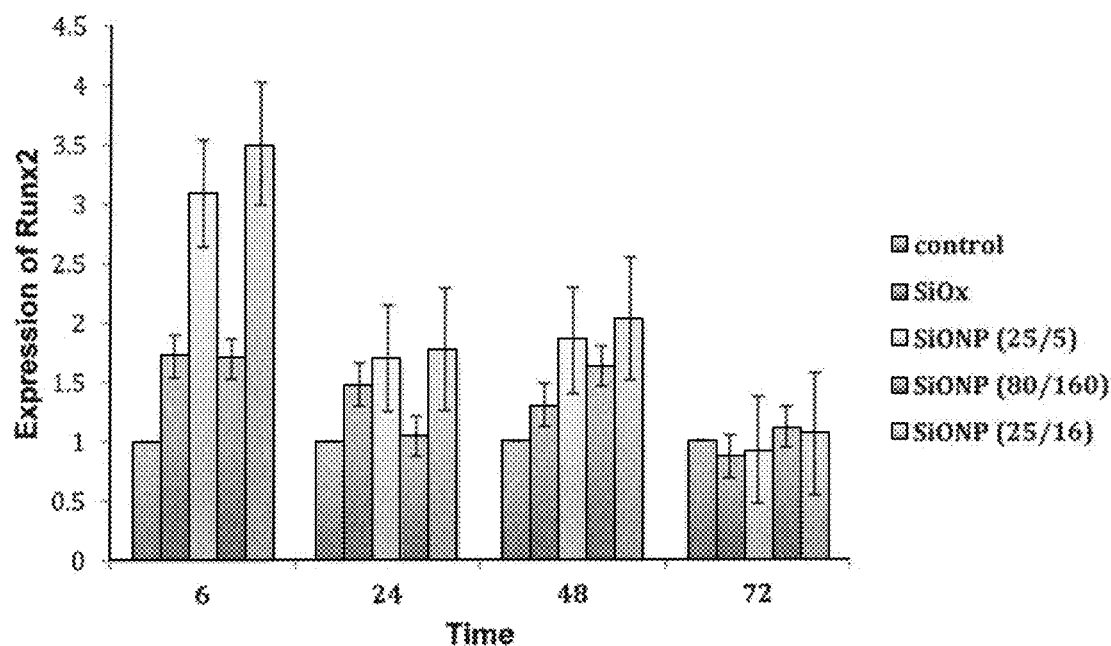

FIG. 42E—Relative expression of Runx2 onto SiOx and SiONP surfaces at 6 hours, 24 hours, 48 hours, and 72 hours.

Figure 42F:
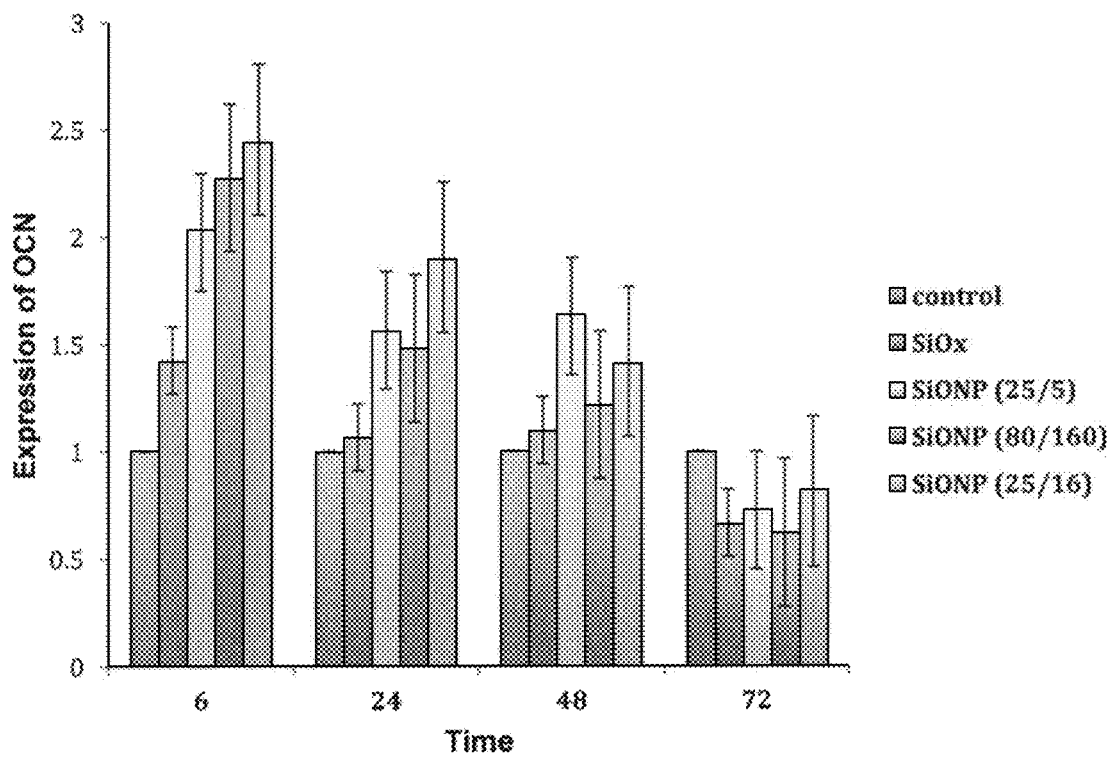

FIG. 42F—Relative expression of OCN onto SiOx and SiONP surfaces at 6 hours, 24 hours, 48 hours, and 72 hours.

Figure 42G:
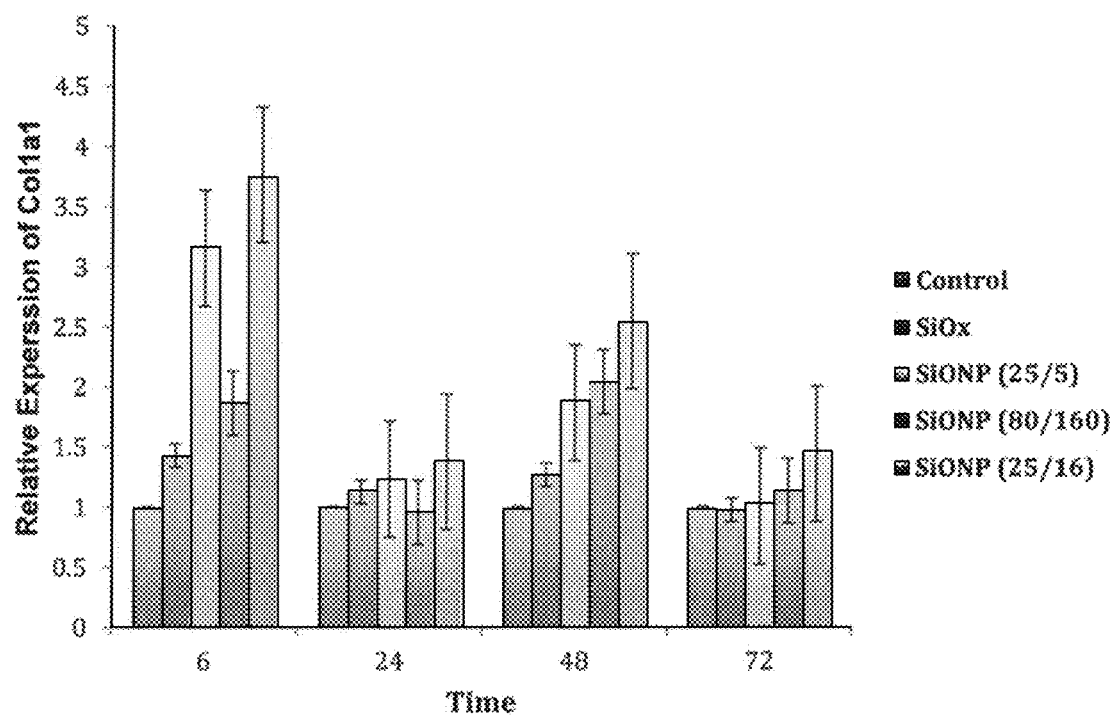

FIG. 42G—Relative expression of Col1a1 onto SiOx and SiONP surfaces at 6 hours, 24 hours, 48 hours, and 72 hours.

Figure 43A:
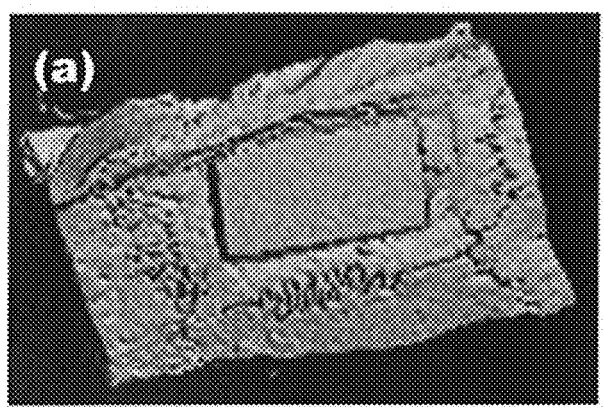
Figure 43B:
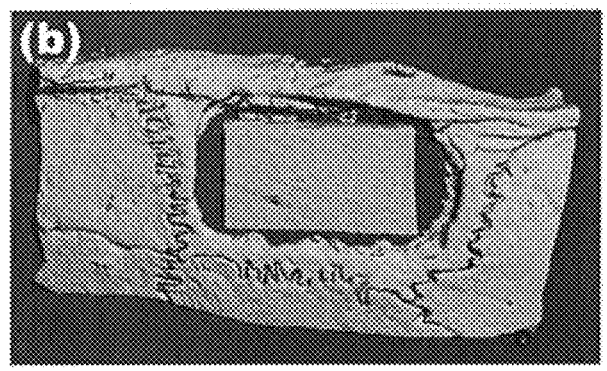
Figure 43C:
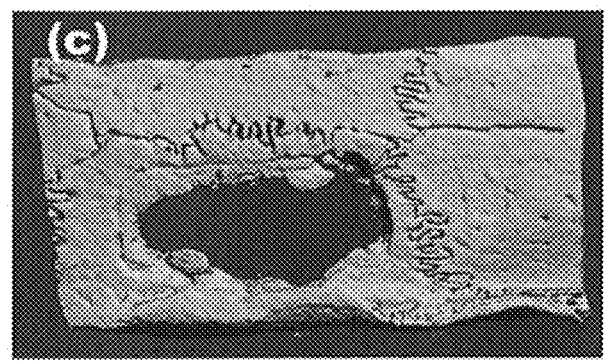

FIG. 43A—In vivo data on SiONP coated surfaces. MicroCT micrographs showed that Si(ON)x samples triggered the rapid bone-regeneration process and filled the gap completely within 5 weeks. FIG. 43B—In vivo data on non-SiONP coated surface (control samples) do not show much bone to fill the interfacial gap over the same time period. FIG. 43C—In vivo data on empty defect (control).

Figure 44:
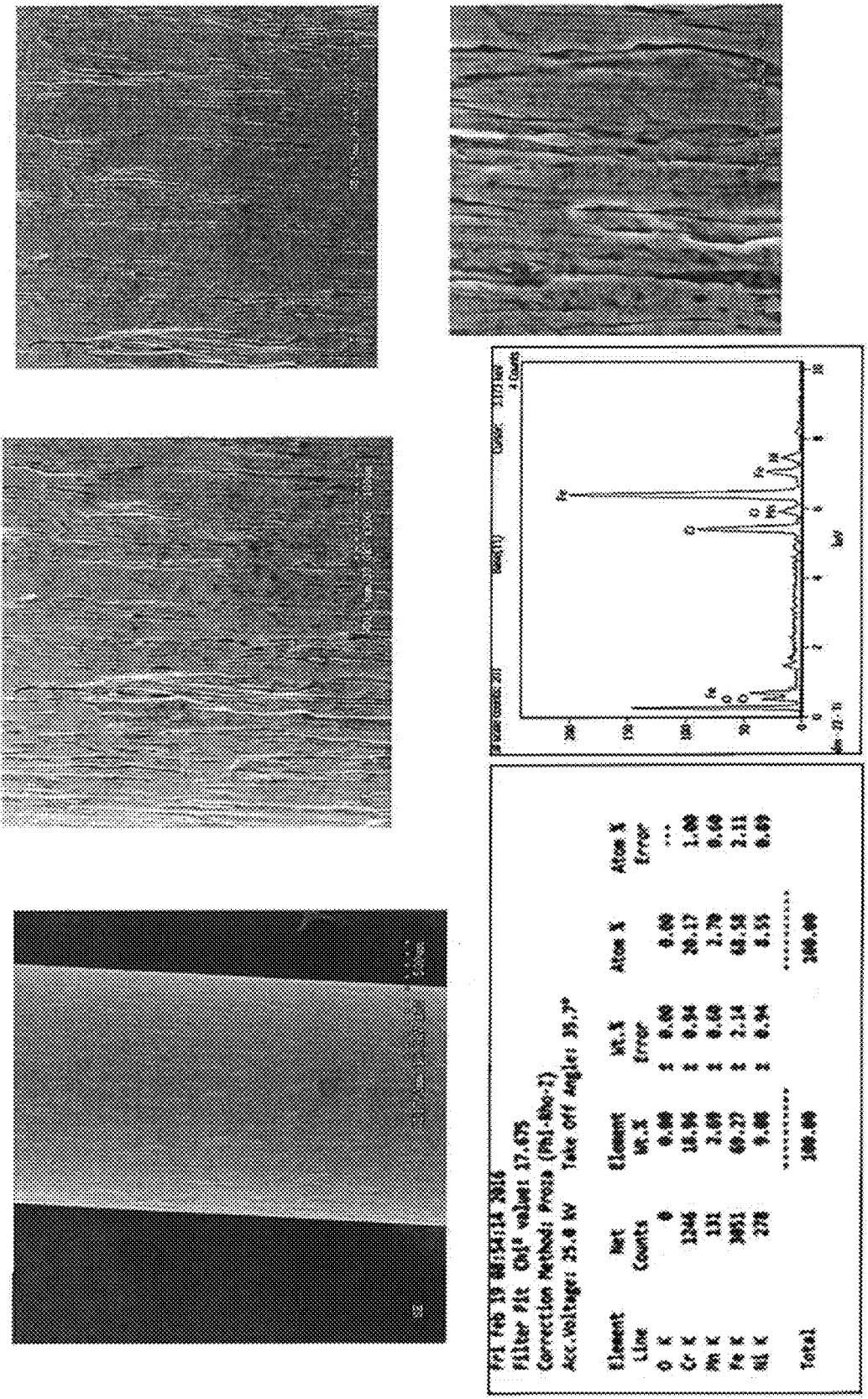

FIG. 44—SEM/EDX data from Kirschner wire (K-wire) rods without a SiONP coating.

Figure 45A:
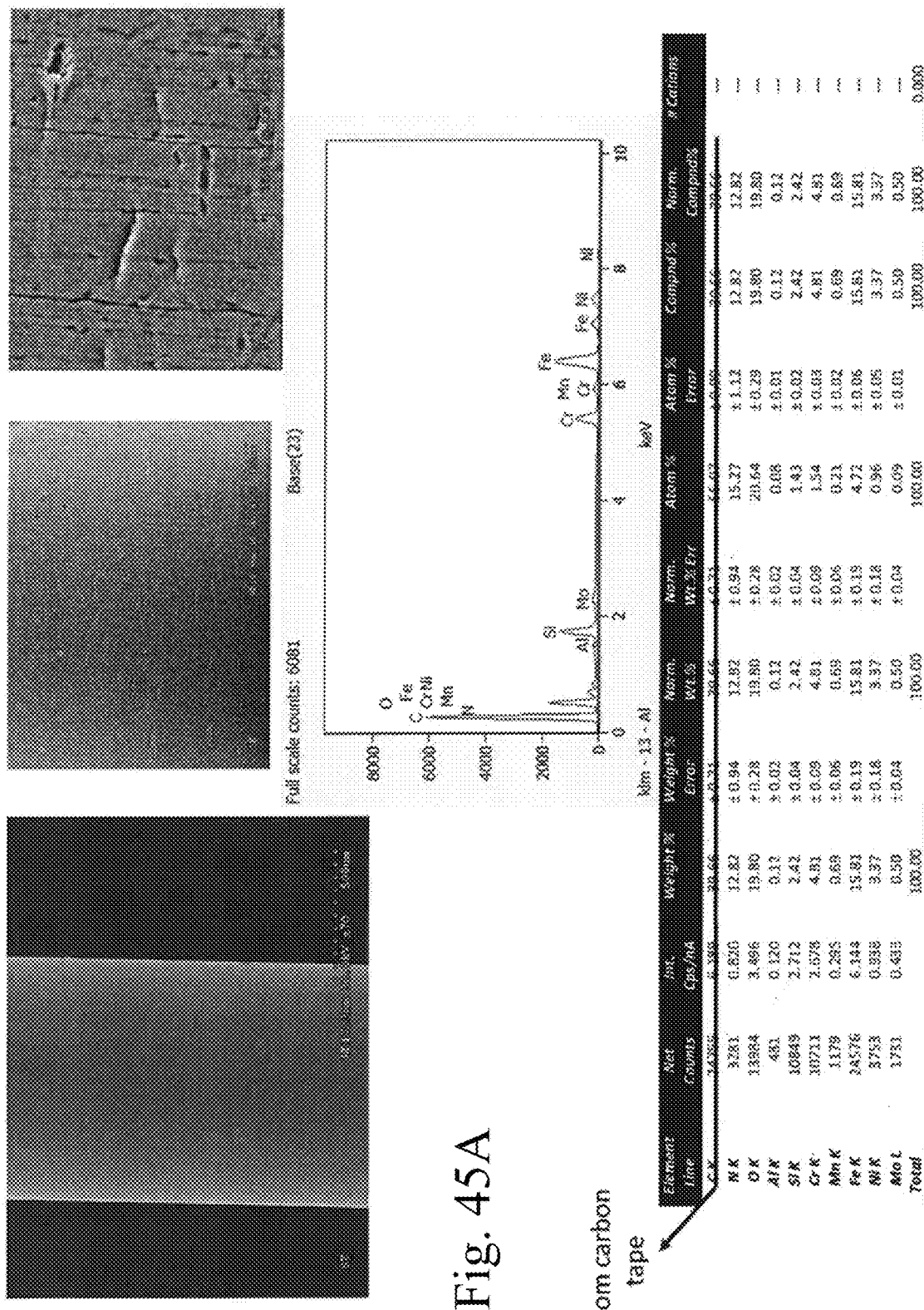
Figure 45B:
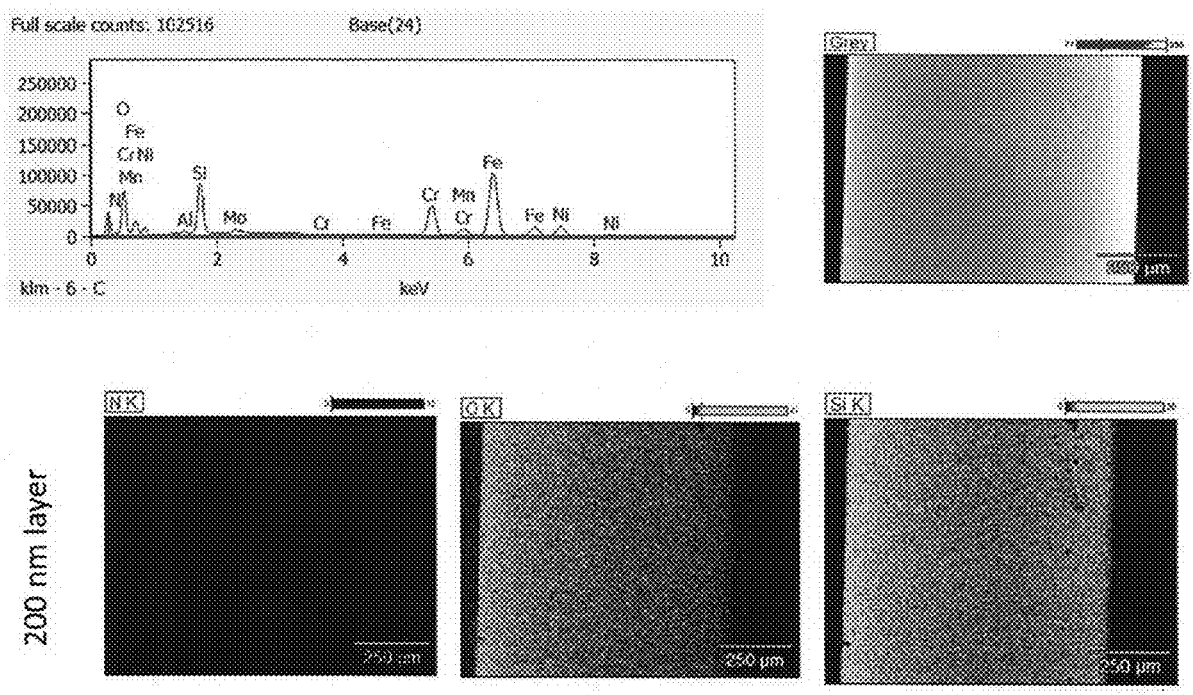

FIG. 45A—SEM/EDX data from Kirschner wire (K-wire) rods with a SiONP coating (200 nm SiNO). FIG. 45B—EDX/Mapping coated rods (200 nm SiNO).

Figure 46A:
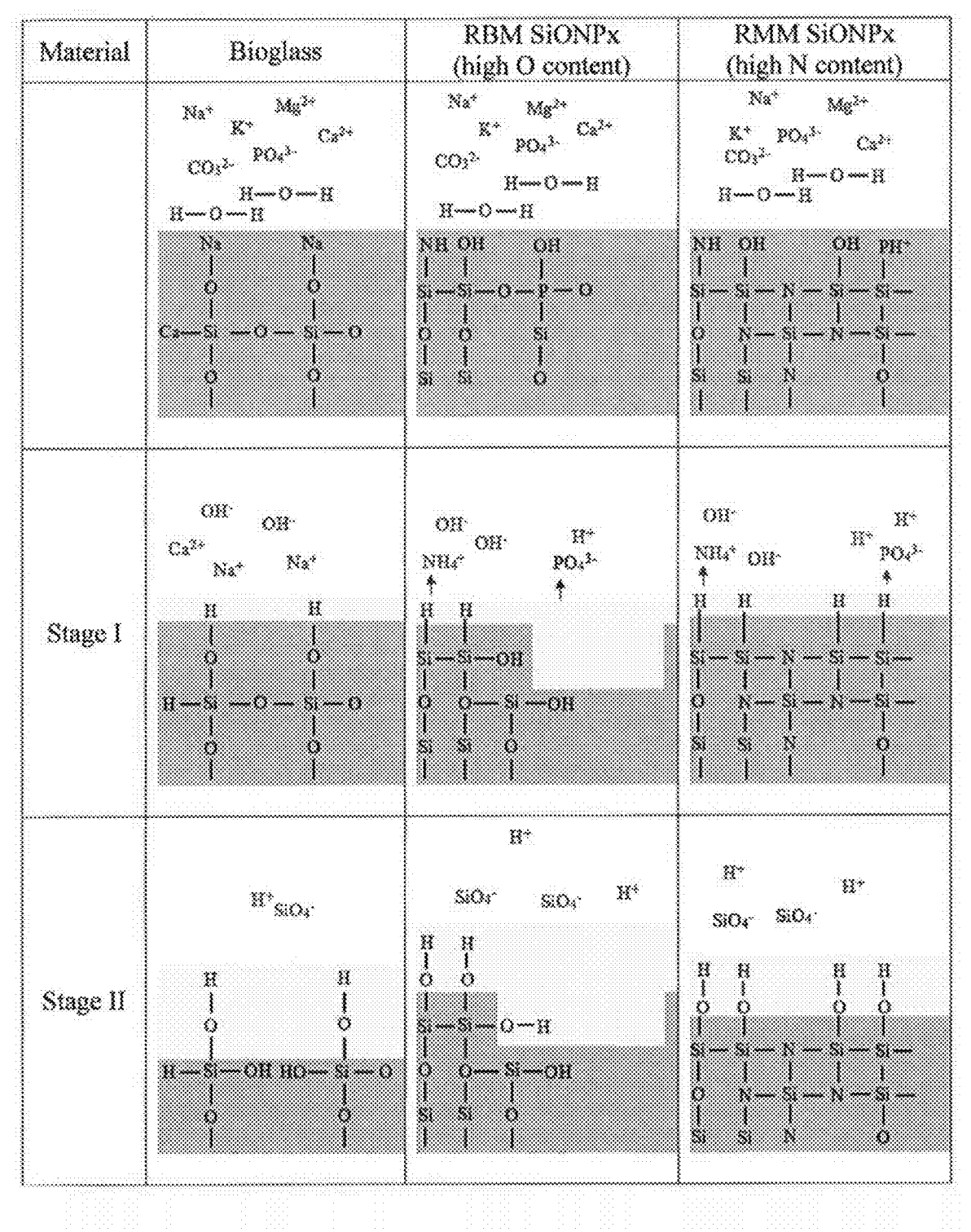

FIG. 46A—Initial stages of the dissolution of a bioglass and RBM and RMM forms of SiONPx coating chemistries. Stage I, Stage II; FIG. 46B—Stage III, Stage IV and Stage V.

FIGS. 47A-47D; FIG. 47A Glass cover slip Tubules Thickness; FIG. 47B SiON Tubues Thickness; FIG. 47C SiONP Tubules Thickness; FIG. 47D Bar graph showing glass cover slip, SiON and SiONP Tubules Thicknesses.

Figure 48A:
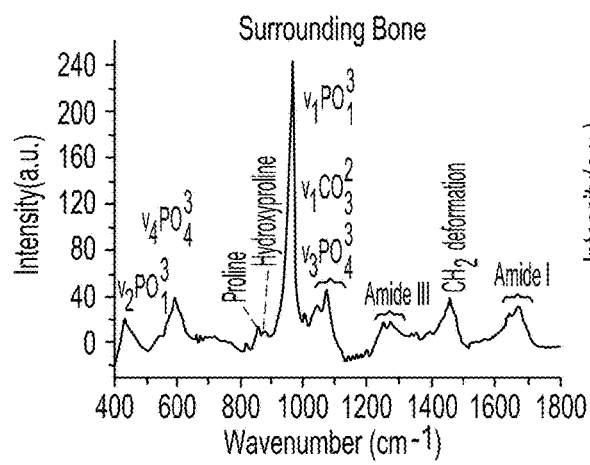
Figure 48B:
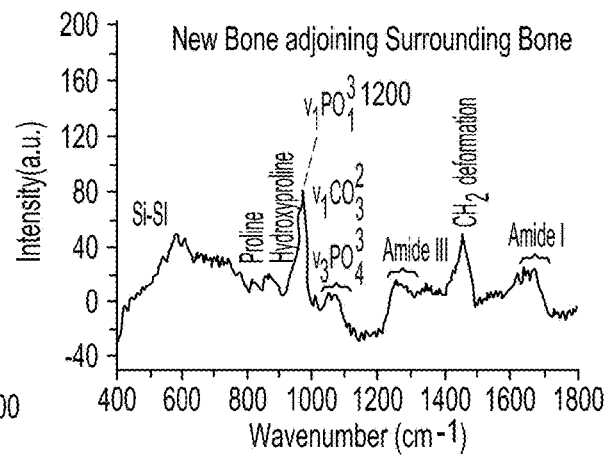
Figure 48C:
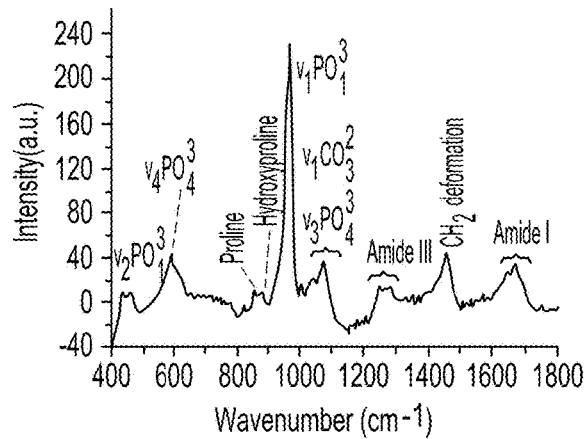
Figure 48D:
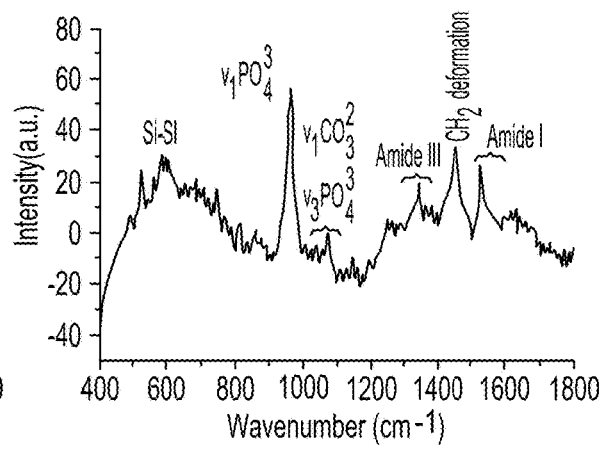

FIGS. 48A-48D; FIG. 48A Surrounding Bone; FIG. 48B New Bone Adjoining Surrounding Bone; FIG. 48C New Bone Adjoining SiONP Surface; FIG. 48D New Bone on the SIONP Surface.

Figure 49A:
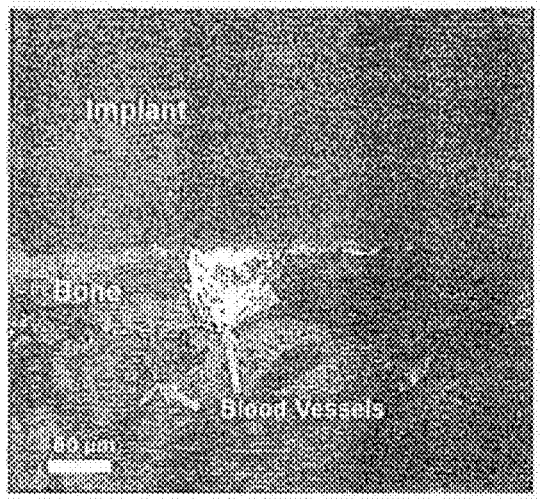
Figure 49B:
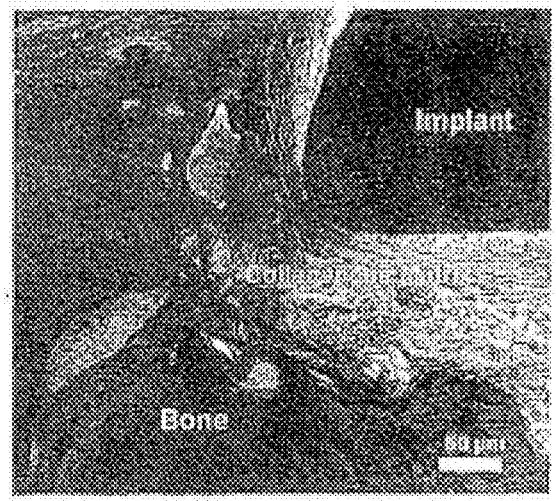

FIGS. 49A-49B; FIG. 49A no collagen formation; FIG. 49B collagen formation.

Figure 50A:
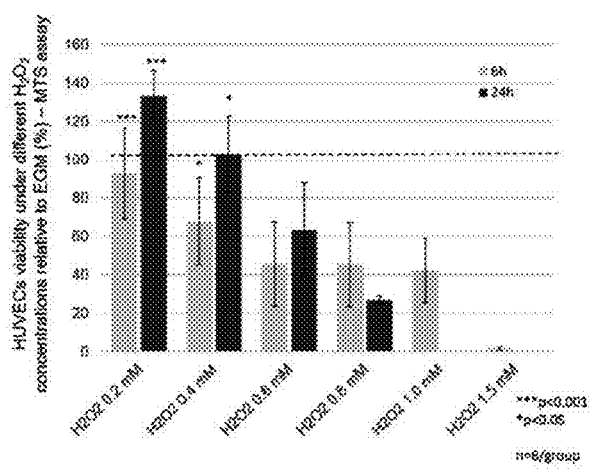
Figure 50B:
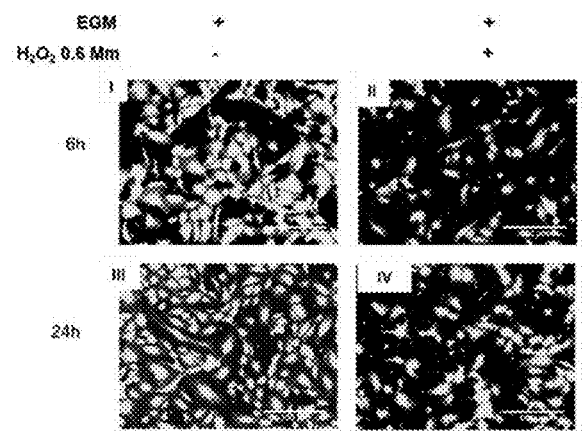

FIGS. 50A-50B: FIG. 50A shows the cells number relative to control at 6 and 24-hour time points. At 6 hours $H_2O_2$ 0.2 and 0.4 mM were significant higher than others with $H_2O_2$ 0.6, 0.8 and 1 mM at the same level. At 24 hours $H_2O_2$ 0.6 mM was significant lower than 0.4 mM and higher than 0.8 mM (***$p<0.001$, *$p<0.05$, n=6/group). FIG. 50B Show fluorescent pictures of HUVECs stained with Calcein-AM at 6 h (I and III) and 24 h (II and IV). Pictures I and III show cells exposed to endothelial cell growth media (EGM) and pictures II and IV show cells exposed to EGM and Hydrogen peroxide ($H_2O_2$).

FIGS. 51A-51D: FIG. 51A The bar graph shows the viable cells number measured by MTS assay after 6 and 24 hours. At 24 hours the EGM presented the best result among all groups. However, $Si^{4+}$ 0.5 mM was the best among the silica groups and EBM. $Si^{4+}$ 1 mM was the worst at 24 hours. (**$p<0.01$, *$p<0.05$, #$p<0.05$) (n=6). FIG. 51B Bar graph shows cells proliferation relative to initial cell seeding after 6, 24 and 48 hours. At 6 hours all silica groups similarly presented a significantly higher relative cell number compared with controls. At 24 and 48 hours, among all groups, EGM was significatly higher and $Si^4+1$ and EBM was the lowest at 24 h and 48 h, respectively. FIG. 51C Fluorescent pictures (5× view) of HUVECs stained with Calcein-AM after 48 h, showing enhancement of cell proliferation after exposure to silica ion. Picture I shows the lowest cell number on negative control (EGM 20%). The higher cell number was obtained on positive control (picture II), followed by EGM 20%+$Si^{4+}$ 0.5 mM group (picture IV). The other two silica ion groups (picture III and V) showed similar results and were lower than positive control and EBM 20%+$Si^{4+}$ 0.5 mM. FIG. 51D Bar graph showing cell number relative to positive control (EGM). EGM 20%+$Si^{4+}$ 0.5 mM relative cell number was 2 fold higher than the other silica groups, and 5 fold higher than negative control (EBM 20%). (*$p<0.001$, $p<0.01$, *$p<0.05$, ##$p<0.01$, #$p<0.05$) (n=6). EGM→endoltheleial cell growth media; EBM→endothelail cell basal media.

Figure 52A:
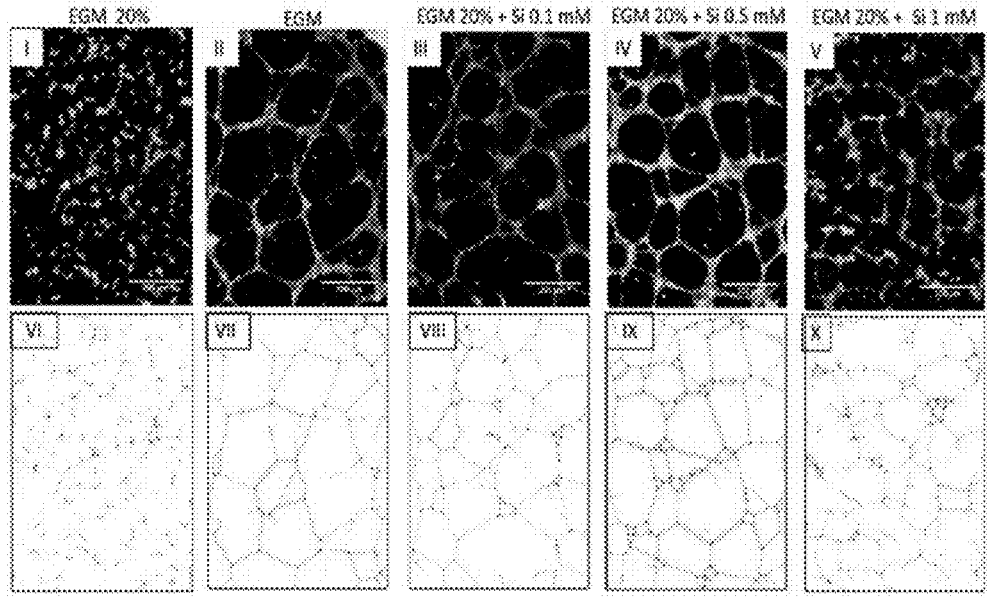
Figure 52B:
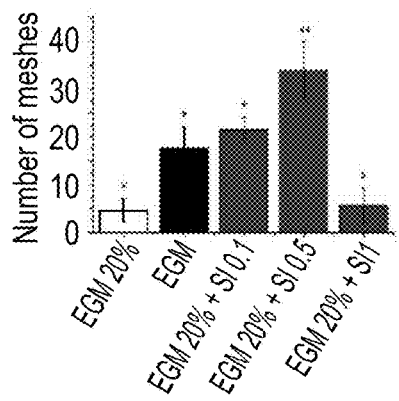
Figure 52C:
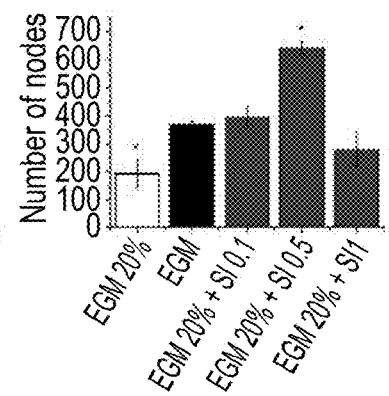

FIGS. 52A-52I: FIG. 52A Pictures I, II, III, IV and V show fluorescent pictures (5× view) of HUVECs stained with Calcein-AM 6 hours after seeding on bed of Matrigel using a specific cell culture media. Pictures VI, VII, VIII, IX, X show the lines traced on fluorescent pictures made by Angiogenesis Analyzer (ImageJ plug-in). $Si^{4+}$ 0.5 mM presented the best parameters among all groups, especially on number of meshes and nodes. FIGS. 52B-52F Show analysis of data collected from ImageJ. $Si^{4+}$ 0.5 mM presented significant higher number of nodes, meshes, junctions and segments when compared with other groups. FIG. 52G Fluorescent pictures (5× and 10× view) of HUVECs stained with Calcein-AM 3 hours after media change and 27 hours after initial cell seeding. Pictures I and V show a low number of circles. Pictures II, III, IV, VI, VII and VIII represent the cells exposed to different silica ion concentrations and show a higher number of circular structures similar to pre-capillary tubes. FIG. 52H Bar graph showing the data analysis from the fluorescent pictures of number of circles according to group relative to control (EGM). EBM+$Si^{4+}$ 0.5 mM produced a significant higher number of circles followed by 0.1 mM, and 1 mM. FIG. 52I Angiogenesis analyzer (Image J plug-in). (Arrow head A-B); nodes, identified as pixels that had at least 3 neighbor, corresponding to a bifurcation (arrow A-B); twig (C1, D1), segment (C2, D2) delimited by two junctions (C3, D3) (note that this pointed junction is composed by several nodes) and branch (C4, D4). E shows a junction implicated only in branch (E1) and master junctions like E2 delimiting master segments (E3). F shows the master tree composed from master segments associated by master junctions delimiting the meshes (F1). Optionally, two close master junctions can be fused into an unique master junction (F2). Note the underlying segment (F3). (*$p<0.001$, $p<0.01$, *$p<0.05$, ### $p<0.001$, # $p<0.05$). EBM→endothelial cell basal media; EGM→endothelial cell growth media.

FIGS. 53A-53D: FIG. 53A Scratch wound healing assay. Pictures (5× view) of wounded area on time 0 h (no staining) and 12 h (toluidine blue staining). Picture I shows EGM (positive control) group with higher wounded area occupied by migrated cells. Picture II shows EBM (negative control) group with lower number of cells on wounded area and picture III represents EBM treated with $Si^{4+}$ 0.5 mM showing the effect of silicon on cell migration compared to EBM (picture II). FIG. 53B Graph shows percentage of occupied initial wounded area by migrated cells relative to control (EGM) 12 h after scratch. EBM+$Si^{4+}$ group presented almost 3 times more occupied area than EBM without silicon. FIG. 53C Fluorescent pictures of HUVECs stained with DAPI 12 hours after transwell cell migration. Pictures I, IV and VII show EGM (positive control), Pictures II, V and VIII EBM+2% FBS (negative control), and pictures III, VI and IX silicon treatment group. FIG. 53D Bar graph presents number of transwell migrated cells relative to EGM (positive control). Silicon treatment group showed 2 times more cell migration than negative control. (*$p<0.05$) (n=3/group). EGM→endothelial cell growth media; EBM→endothelial cell basal media; FBS→fetal bovine serum.

Figure 54A:
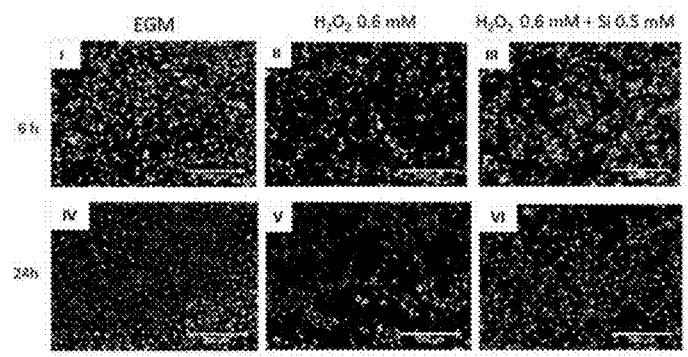
Figure 54B:
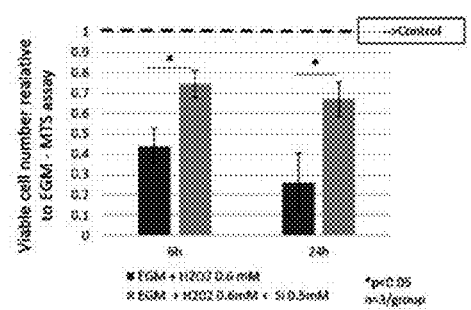
Figure 54C:
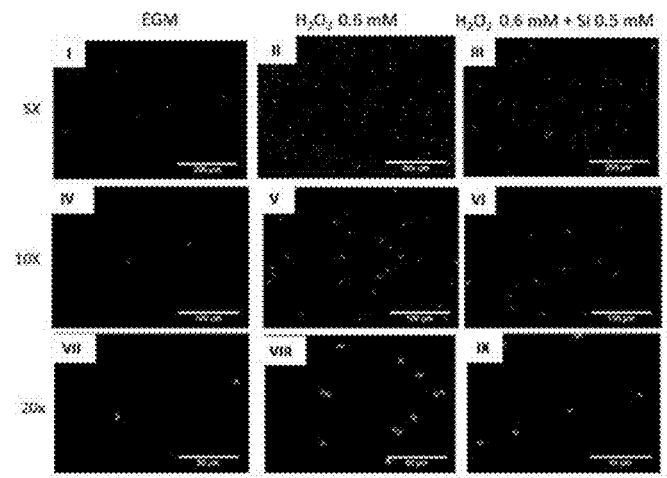
Figure 54D:
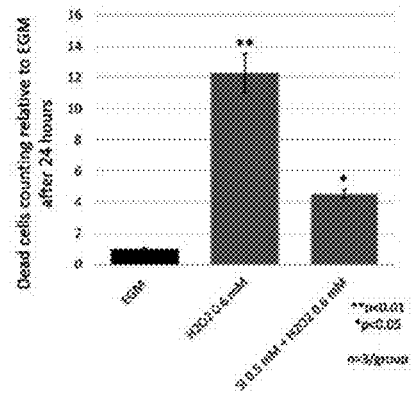

FIGS. 54A-54D: FIG. 54A Pictures (5× view) of HUVECS stained with Calcein-AM under hydrogen peroxide oxidative stress with and without silica ion treatment compare to control. Pictures I and IV show EGM (control) group. Pictures II and V show cells exposed to $H_2O_2$. And pictures III and VI show HUVECs under $H_2O_2$ environment and treated with $Si^{4+}$ 0.5 mM. FIG. 54B Graph presents data of comparison between treated and non-treated group relative to control (EGM). Treatment group shows twice and three times more viable cells than $H_2O_2$ 0.6 mM group at 6 hours and 24 hours, respectively. FIG. 54C Fluorescent pictures after propidium iodide staining 24 hours after cell seeding. Pictures I, IV and VII show different magnification of lowest number of dead cells on negative control (EGM). Pictures II, V and VIII show different magnifications of highest number of dead cells on positive control ($H_2O_2$ 0.6 mM). Pictures III, VI and IX show lower number of died cells than positive control. FIG. 54D Bar graph shows that silicon treatment group ($H_2O_2$+Si 0.5 mM) have 3 times less dead cells than positive control ($H_2O_2$ 0.5 mM). (*$p<0.001$, $p<0.01$, *$p<0.05$) (n=3/group). EGM→endothelial cell growth media.

Figure 55A:
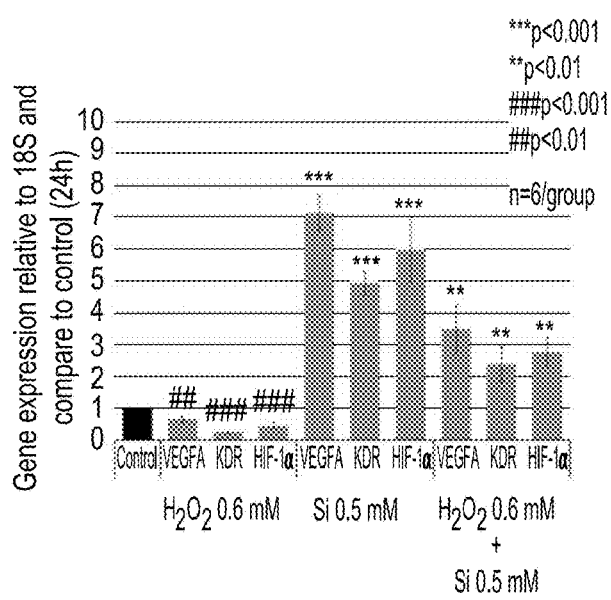
Figure 55B:
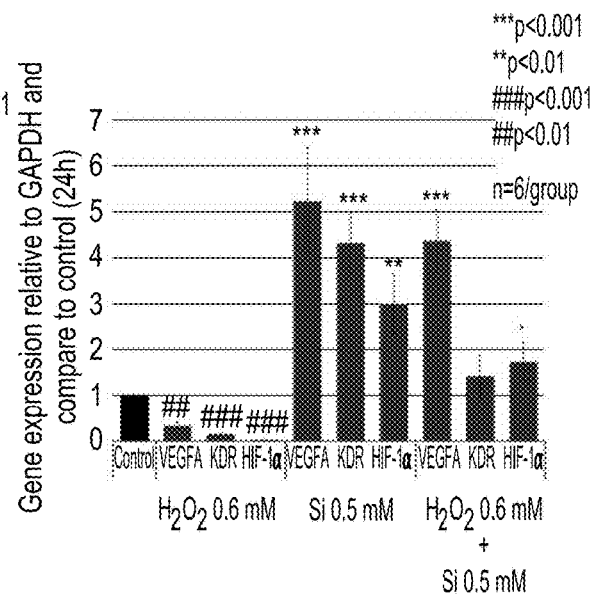

FIGS. 55A-55B: FIG. 55A Bar graph showing gene expression of VEGFA, KDR and HIF-1α 24 hours after cell seeding relative to 18S (housekeeping gene) compare to control (endothelial cell culture media). All genes were significantly over expressed in the silicon group ($p<0.01$) and $H_2O_2$ treated with silicon group ($p<0.05$). FIG. 55B Bar graph presenting gene expression of VEGFA, KDR and HIF-1α 24 hours after cell seeding relative to GAPDH (housekeeping gene) compare to control (endothelial cell culture media). VEGFA, KDR and HIF-1α presented significant overexpression in the silicon group ($p<0.05$) and VEGFA was significant increased on cells exposed to $H_2O_2$ and treated with silicon ($p<0.01$). (**$p<0.01$, *$p<0.05$) (n=4/group). VEGFA→vascular endothelial growth factor A; KDR→vascular endothelial growth factor receptor 2; HIF-1α →hypoxia-inducible factor 1-alpha; GAPDH→Glyceraldehyde 3-phosphate dehydrogenase.

Figure 56:
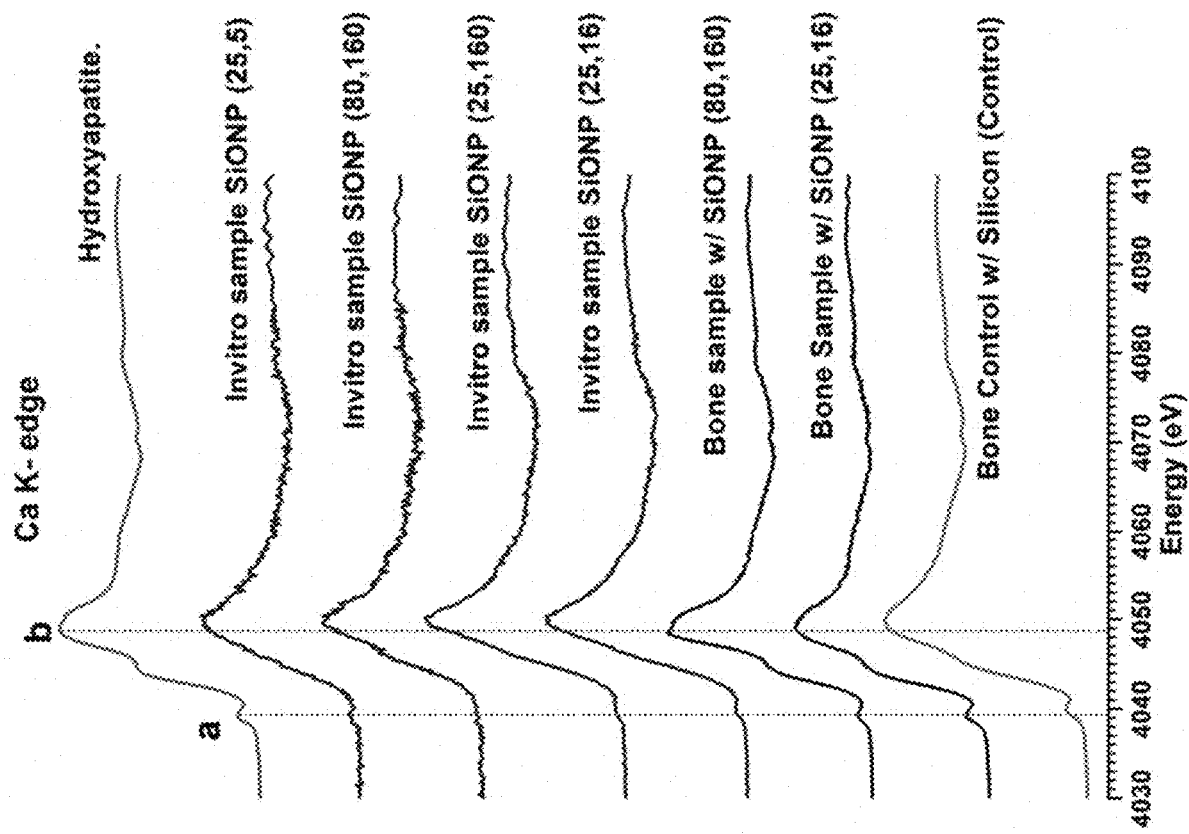

FIG. 56 shows the Ca K edge spectra for various samples examined in the SiONP studies. It can be seen that SiONP samples after in vivo implantation and recovery from the rat cranium show the presence of Ca—P phases consistent with new bone formation. Here, HA is used as a model compound for comparison of the mineral phase of HA in bone. The Ca K edge peak of HA is different from other model compounds with a pre edge peak "a" at 4039.1 ev. It has a pre edge shoulder at 4044.4 and main peak "b" at 4048.27 ev. The post edge shoulder corresponds to transition to unoccupied states, mainly 5s states. The main edge peak "b" is assigned to 1 s to 4p transition. The shift in energy towards higher energy levels for peak "b" could represent differences in the type of mineral formed in vitro as compared to the mineral formed in vivo. The mineral formed in vitro could be amorphous Ca—P (precursor to the formation of HA).

Figure 57:
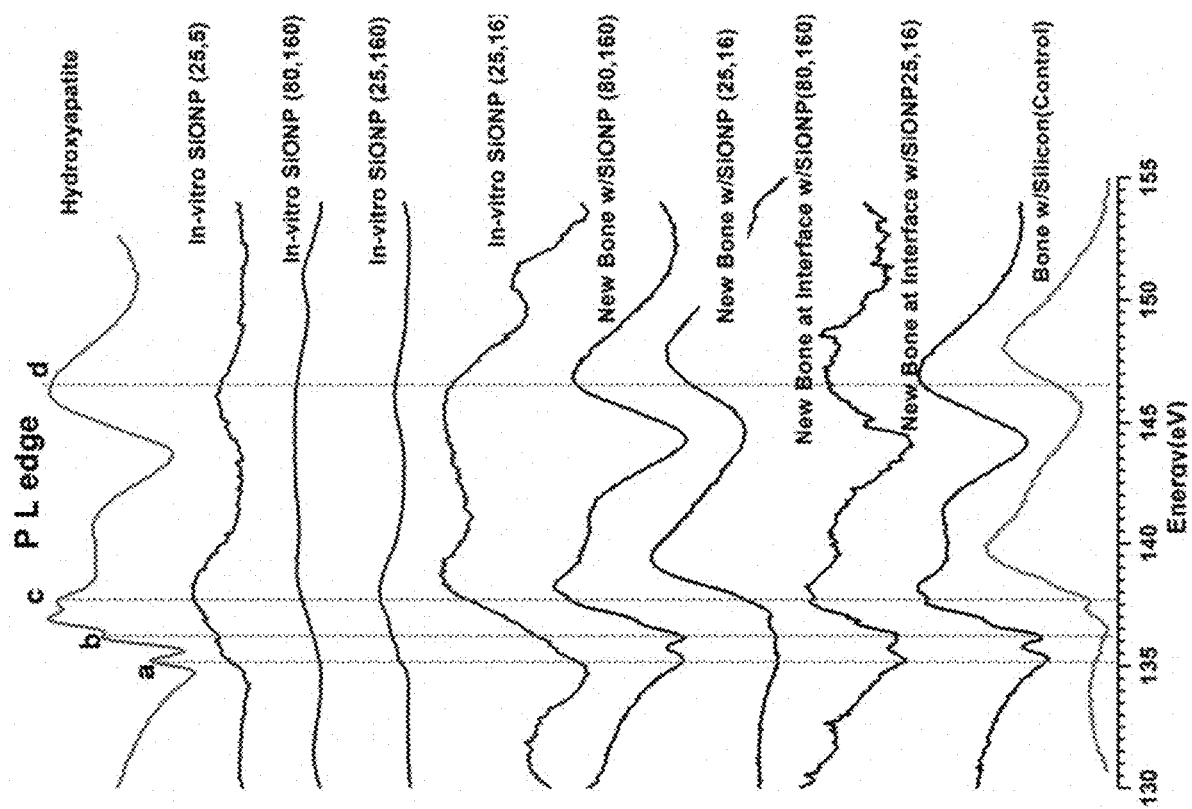

FIG. 57 shows the phosphorus L edge spectra for SiONP samples examined in this study. Similar to Ca K edge spectra, the P L edge spectra indicate the newly formed bone on SiONP samples has a similar P structure as that in HA model compounds. The main Peak c is at 137.8 eV, pre edge peak "a" at 135.7 and pre edge peak "b" around 136.5. There is also shoulder after peak "c" around 141 eV and secondary peak "d" at 146.7 eV. Peak "a" and "b" at the lower energy side are separated by 1 ev and arise from the spin orbit split into 2p electron into $2p_{3/2}$ and $2p_{1/2}$ levels. The main peak "c" is attributed to transitions to 3p orbital made possible due to presence of other elements such as oxygen and cationic species like Si and Ca. The shoulder after peak "c" is characteristic of Ca phosphates and arises from transitions from P 2p to empty Ca 3d orbitals. Peak "d" seen in all phosphates is due to transitions from 2p to 3d orbital in phosphorous.

DETAILED DESCRIPTION OF THE INVENTION

While preferred embodiments have been shown and described herein, it will be apparent to those skilled in the art that such embodiments are provided by way of example only. Numerous variations, changes, and substitutions will now occur to those skilled in the art without departing from the spirit of the disclosure. It should be understood that various alternatives to the embodiments described herein may be employed in practicing the subject matter described herein. It is intended that the following claims define the scope of the disclosure and that methods and structures within the scope of these claims and their equivalents be covered thereby.

Certain Definitions

The term "amorphous" as it is used in the description of the present materials, thin films, nano-films, deposition chemistries, compositions, surfaces, devices, and methods of use is defined as a solid phase material that has no crystalline structure and no stoichiometric formula. A particular attribute of the amorphous materials and methods of the present invention is that they possess the characteristic of permitting the ingress of protons into them when they are in an aqueous or partially aqueous environment, such that protons are able to invade the amorphous network of the material (such as the thin film/nano-film treatment provided on a surface), and subsequently release cations (e.g., Si) into the surrounding environment. This is different from conventional and/or standard amorphous materials, such as a glass window, in that conventional amorphous materials are reinforced with other elements and/or constituents, resulting in an amorphous material that does not readily allow it to dissolve in an aqueous environment. Thus, the term amorphous as it is used in the present materials are soluble or at least partially soluble in an aqueous in vitro and/or in vivo environment.

As used in the description of the present invention, all reference to silica, Si—O, and, or other silicon oxygen materials will be denoted $SiO_x$ or $SiO_2$.

As used in the description of the present invention, all Si—N, silicon nitride, $Si_3N_4$, or other silicon and nitrogen compounds are referred to as $SiN_x$ or $Si_3N_4$.

As used in the description of the present invention, all $Si_zO_xN_y$, (Si—Si)$_z$(Si—O)$_x$(Si—N)$_y$, silicon oxynitride, or any other combination of silicon, oxygen and nitrogen are referred to as $Si(ON)_x$.

As used in the description of the present invention, all $Si_zO_xN_yP_w$, (Si—Si)$_z$(Si—O)$_x$(Si—N)$_y$(Si—P)$_w$, Phosphorous-Containing Silicon Oxynitride, or any combination of silicon, oxygen, nitrogen and phosphorous are referred to as SiONPx.

As used in the description of the present invention, the term "coating" or "nanofilm" includes any film or layer comprising SiONPx in the form of nanoparticles, nanospheres, or nanorods. In some embodiments, the nanofilm comprises nanoscale particles that form a nano-network film on a surface.

As used in the specification and the appended claims, the singular forms "a", "an" and "the" include plural references unless the context clearly dictates otherwise. Thus for example, reference to "the method" includes one or more methods, and/or steps of the type described herein and/or which will become apparent to those persons skilled in the art upon reading this disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Abbreviations

PECVD—Plasma-Etched Chemical Vapor Deposition
XANES—X-ray absorption near-edge structure
sccm—standard centimeter cubed per minute
SiONPx—Phosphorous-Containing Silicon Oxynitride
SiONx—Silicon Oxtnitride
SEM—Scanning electron microscopy
RBM—Random Bindng Model
RMM—Random Mixing Model
TEOS—$Si(OC_2H_5)_4$ Tetraethyl orthosilicate SiONPx Formation The present invention provides Si—O—N—P thin films for osseoapplications. Inventors have found through detailed chemical characterization of a disordered bone model and by fabrication of a surface incorporating phosphorous that is based on the chemistry of silicon/silicon oxide to enhance osteogenic markers in bioactive glasses. These glass coatings will form a bond with bone through the formation of a mineral layer in a simulated body fluid environment in vitro, in a manner similar to commercially available bioglass. The composition of the formed mineral layer is controlled by the coating chemistry. This control, in turn, may be leveraged in diseased bone systems where the mineral is believed to be altered in order to form a strong interface between the mineral in disordered bone and the implant glassy coating.

The present invention provides a bioactive glassy Ti-coating for improved osseointegration that bond well to the $TiO_2$ surface. This improved interface is achieved via a ceramic plasma-etched chemical vapor deposition (PECVD) coating process which is commonly used to deposit glassy layers onto titanium in the semiconductor industry while simultaneously attempting to incorporate P into the coating. Some embodiments of the invention incorporate an amorphous phosphorous-containing silicon oxynitride (SiONPx) as a possible $TiO_2$-compatible, bioactive thin film for osseointegration. Two distinct theoretical models have been developed to approximate the chemistries formed from these types of coatings: the Random Mixing Model (RMM) and the Random Bonding Model (RBM). The Random Mixing Model (RMM) states that a non-stoichiometric silicon oxynitride can be treated as a simple mixture of a-Si—P, SiP2P, Si3N4P, and P2O5 [112] while in the Random Bonding Model (RBM), nitrogen is considered to incorporate into the basic silicon dioxide tetrahedral network and form a chemistry of the form $Si_zO_xN_y$ $P_w$, where z+x+y+w=4. [74] Both approaches have been used to examine PECVD SiONxPw films with a variety of reaction conditions.[66-71] Modified for this P-incorporated system, the RMM would comprise a mixture of: a-Si—P, $SiO_2P$, $Si_3N_4P$, and $P_2O_5$. The RBM would form an elemental chemistry of the form $Si_zO_xN_yP_w$ where z+x+y+w=4.

Ratios:

X-ray absorption near-edge structure (XANES) spectroscopy is particularly well-suited to an elemental study of PECVD-fabricated SiONPx sample chemistry. While XANES has been used previously to study CVD and PECVD silicon oxynitride (SiONx) chemistries and their structures;[66-71] SiONPx systems have not been well studied. Inventors have discovered SiONPx coatings with various oxygen-nitrogen-phosphorous ratios, fabricated via a PECVD process designed to yield a potentially bioactive coating. Process validity and repeatability measures were obtained via ellipsometry and refractometry. X-ray diffraction is used to ensure no crystalline phases were formed during processing. Scanning electron microscopy with energy dispersive spectroscopy is used to evaluate coating composition. Surface energy has been evaluated via a sessile drop technique and calculated according to a two-component method, and X-ray absorption near-edge structure (XANES) spectroscopy is used to evaluate the chemical structure of the SiONPx coatings.

Degradation:

The phosphorous doped silicon oxynitride amorphous coatings (SiONPx) of this invention, with various oxygen and nitrogen ratios, fabricated via the plasma enhanced chemical vapor deposition (PECVD) process were immersed in αMEM and incubated at 37° C. in a humidified 5% $CO_2$ atmosphere for a period of up to 8 days. Scanning electron microscopy with energy dispersive spectroscopy was used to evaluate the microstructure of the surfaces after soaking for 6 hours and 8 days, and X-ray absorption near-edge structure (XANES) spectroscopy was used to evaluate any changes in the chemical structure of the SiONPx coatings after soaking. Applicants have found that calcium phosphate mineral forms on the surface suggesting that these coating chemistries would be bioactive in vivo.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In the following Examples 1-5, the fabrication and characterization of Si—O—N—P coatings is discussed, followed by the degradation study of amorphous Si—O—N—P coatings in Examples 6-13. Additional examples 14-20 are also provided.

Example 1—Fabrication of SiONP$_w$ Coatings

A wet oxidation method was used to deposit a uniform (non-uniformity<1%) 100 nm oxide layer onto <1 0 0> p-type test grade Si wafers (Nova Electronic Materials, Flower Mound, Tex.). A TRION ORION II PECVD/LPCVD system was then used to coat the oxidized wafers with 100-1000 nm of a Si—O—N—P amorphous coating via a PECVD (plasma enhanced chemical vapor deposition) process. All coating were fabricated at a substrate temperature of 400° C., chamber pressure of 900 mTorr, an ICP power of 30 W with a 13.56 MHz excitation frequency applied. Source gases included silane ($SiH_4$) and phosphine ($PH_3$) diluted in argon (Ar) (15% $SiH_4$/2% $PH_3$/85% Ar), nitrous oxide ($N_2O$), nitrogen ($N_2$), and ammonia ($NH_3$). The silane flow rate was kept low at 24 sccm (15% $SiH_4$) to prevent undesirable gas-phase reactions, and the silane to phosphine ratio was kept constant due to source gas limitations. The nitrogen and ammonia flow rates were kept high at 225 sccm and 50 sccm, respectively, to try and increase the nitrogen (and N—H as well as Si—H) content of the films. Six different types of coatings were prepared by varying the nitrous oxide flow rate as seen in Table 1. The refractive indices and the thickness of the wafer coatings were measured using ellipsometry at a wavelength of 632.8 nm (Gaertner LS300), and results were confirmed through the use of a reflectometer (Ocean Optics NC-UV-VIS TF Reflectometer) and a scanning electron microscope (Hitachi S-3000N VP SEM). From the thickness measurements and plasma-on times, deposition rates were also determined.

For comparison, six SiONx coatings were prepared using the same deposition conditions, with the exception of the 2% $PH_3$ flow. The 15% Silane/2% Phosphine/83% Argon cylinder was swapped with a 15% Silane/85% Argon cylinder to create amorphous PECVD silicon oxynitride coatings without phosphorous incorporation. Amorphous Si—O—N PECVD coatings have been more widely studied and provide a basis for meaningful comparison with the less-well understood amorphous Si—O—N—P PECVD chemistries.

TABLE 1

Gas flow rates for the deposition of six silicon oxynitride coating chemistries

| | Gas Flow Rates (sccm) | | | |
|---|---|---|---|---|
| Sample | 15% $SiH_4$/ 2% $PH_3$/ 83% Ar | $N_2O$ | $N_2$ | $NH_3$ |
| 1 | 24 | 0 | 225 | 50 |
| 2 | 24 | 3 | 225 | 50 |
| 3 | 24 | 5 | 225 | 50 |
| 4 | 24 | 16 | 225 | 50 |
| 5 | 24 | 155 | 225 | 50 |
| 6 | 24 | 160 | 225 | 50 |

Figure 1A:
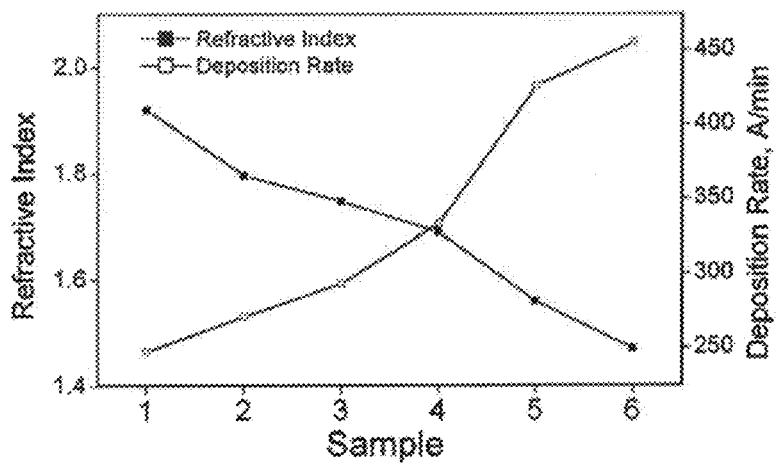
FIG. 1A—Refractive index of thin (~100 nm) SiONPx sample layers and their deposition rate.
Figure 1B:
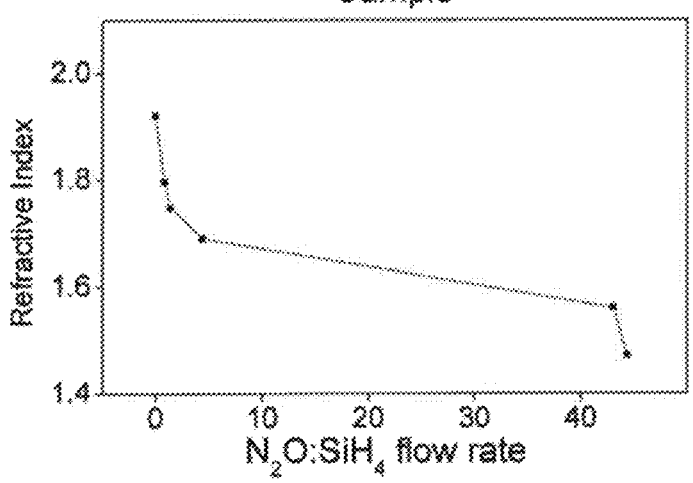
FIG. 1B—Refractive index as a function of $N_2O:SiH_4$ flow rate.

The refractive indices and deposition rates for each set of gas flow conditions was determined using ellipsometry. Refractive index inhomogeneity was determined to be less than 0.007 and the thickness non-uniformity as measured at 15 points on each 4" wafer in the range of 1.6-2.8%. The refractive indices ranged from near that of silicon nitride ($Si_3N_4$ n=2.0) to near than of silicon dioxide ($SiO_2$ n=1.46).[74] Deposition rate decreased and refractive index increased as flow of nitrous oxide decreased which is expected as $N_2O$ is the primary source of oxygen that is incorporated into the film. FIG. 1A gives the refractive indices and deposition rates for the sample set. Refractive index of the samples as a function of the ratio of the flow rates of the primary reactive gases, $N_2O$ and $SiH_4$, has been plotted in FIG. 1B. Note that the $SiH_4$:$PH_3$ ratio is a constant, so a similar general trend of index vs. $N_2O$:$PH_3$ flow rate also exists.

Figure 2A:
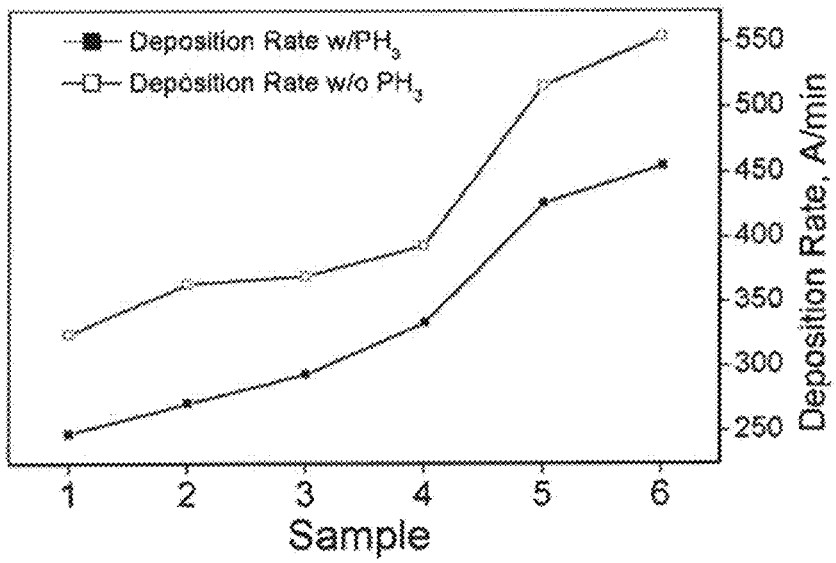
FIG. 2A—The deposition rate of (~100 nm) SiONx and SiONPx coatings.
Figure 2B:
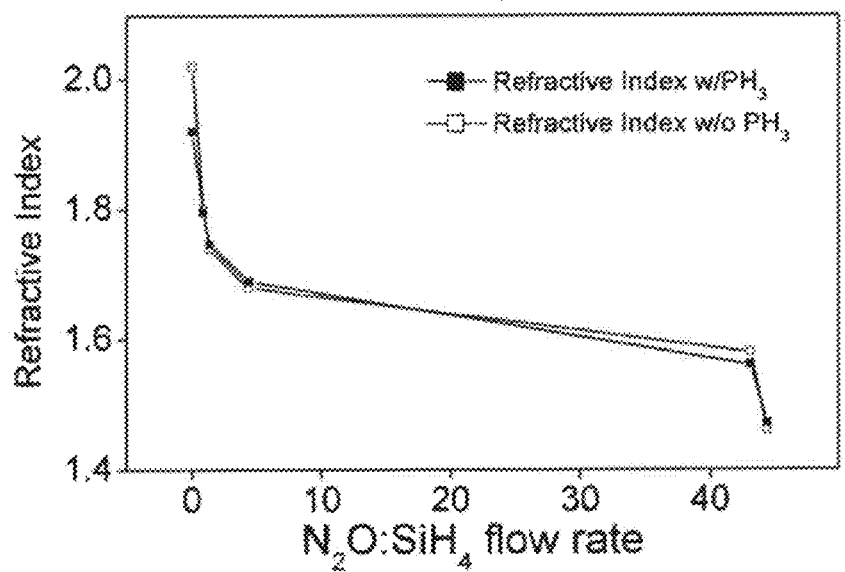
FIG. 2B—Refractive index of SiONx and SiONPx coatings as a function of $N_2O:SiH_4$ flow rate.

A similar trend for the refractive index and sample deposition rate is observed in the coatings deposited without the use of $PH_3$ (SiONx chemistries), however there are significant differences in the two sets of reaction conditions. A comparison of the SiONx and SiONPx refractive indices and deposition rates for similar reaction conditions can be seen in FIGS. 2A and 2B. With the addition of 2% $PH_3$, deposition rates are considerably lower than those observed in similar reaction conditions without phosphine. The only sample conditions that result in a significantly different refractive index is that of the 0 sccm $N_2O$ samples. For the non-$PH_3$ condition, this sample has a refractive index close to that of $Si_3N_4$, while the P-containing sample made under similar conditions has a lower refractive index, which is not entirely unanticipated as the index for $P_2O_5$ (n=1.51) is lower than that of $Si_3N_4$ (n=2.0) and small amounts of oxygen contamination are common in PECVD processing.[65, 148]

Six distinct SiONPx chemistries were fabricated via a repeatable PECVD process designed to create potentially bioactive phosphorous-doped silicon oxynitride coatings. These coatings ranged from oxygen-poor silicon oxynitride (for coatings produced at low nitrous oxide flow rates between 0-16 sccm) to nitrogen-poor silicon oxinitride (for coatings produced at high nitrous oxide flow rates 155 and 160 sccm).

Example 2—XRD Characterization

X-ray diffraction was used to investigate the film for the formation of any crystalline phases. A Bruker D8 Advance diffractometer was used to collect Bragg-Brentano scans using Cu kα radiation (λ=1.5418 Å) at room temperature. Data was recorded over the 2θ range of 20-80° with a 0.02° step size and a dwell time of 1 second.

Figure 3:
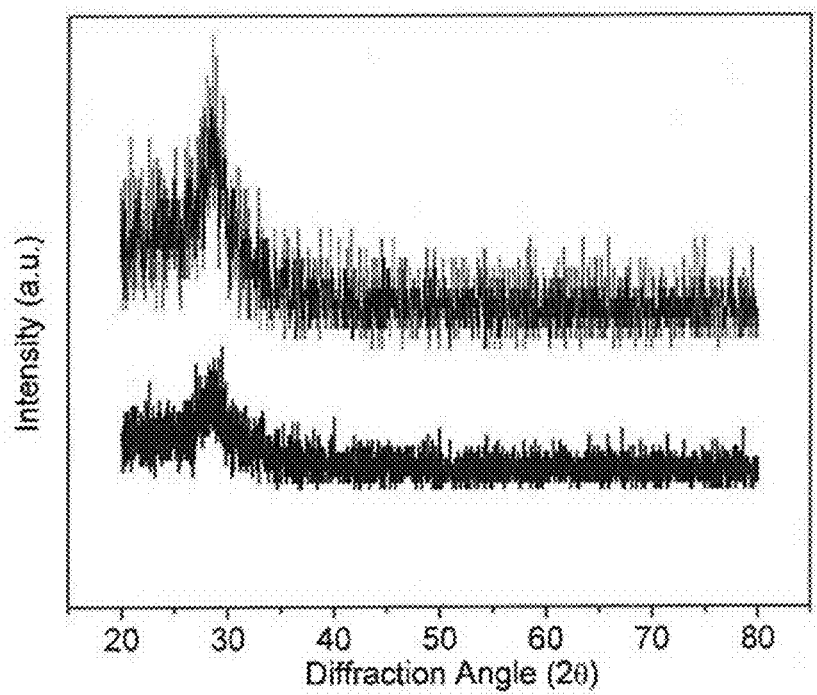
FIG. 3—XRD spectra of samples showing the formation of amorphous silica in both a high oxygen chemistry (Sample 6, top) and a low oxygen chemistry (Sample 1, bottom).

X-ray diffraction was used to confirm the amorphous nature of the coatings. Though X-ray spectra do not show two broad 2theta peaks typical to amorphous silicon oxynitrides[117]: one around 20-30° and one around 60-80°; it is assumed that the $SiO_2$ sub-layer dominates the spectra resulting in one amorphous silica peak. FIG. 3 shows representative spectra from the highest N content Sample 1 and the highest O content sample 6. Other samples show the same general spectra, and spectra are too noisy to provide a basis for comparison and establish a general trend in the data.

XRD spectra confirm that the coatings formed were amorphous.

Example 3—SEM and EDS Evaluation

Surface morphology, film composition, and film thickness were investigated using scanning electron microscopy (Hitachi S-3000N Variable Pressure SEM) equipped with an energy dispersive X-ray spectrometry system (EDAX). SEM images were taken with an acceleration voltage of 20 keV and scans for EDX mapping and compositional studies were taken at 12 keV to prevent interference from sub-coating layers. EDAX software was used to quantify spectral mapping data from 50 μm×50 μm areas. Four regions of interest (ROIs) corresponding to Si, O, N, and P Kα lines were defined and compositional information was calculated using EDAX's proprietary ZAF method.

Figure 4A:
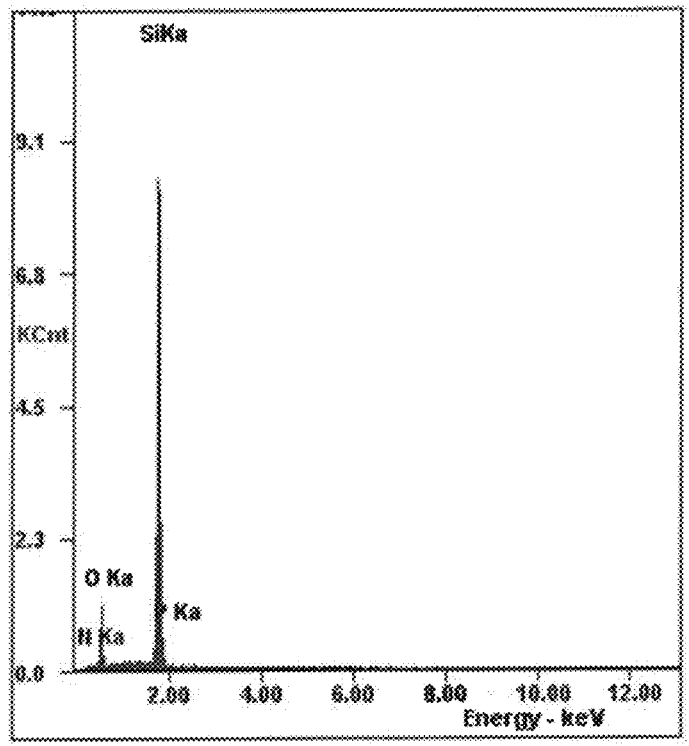
FIGS. 4A and 4B—EDS spectra showing low contaminant element levels for a Phosphorous-containing (FIG. 4A) and non-Phosphorous-containing (FIG. 4B) sample fabricated under similar conditions.
Figure 4B:
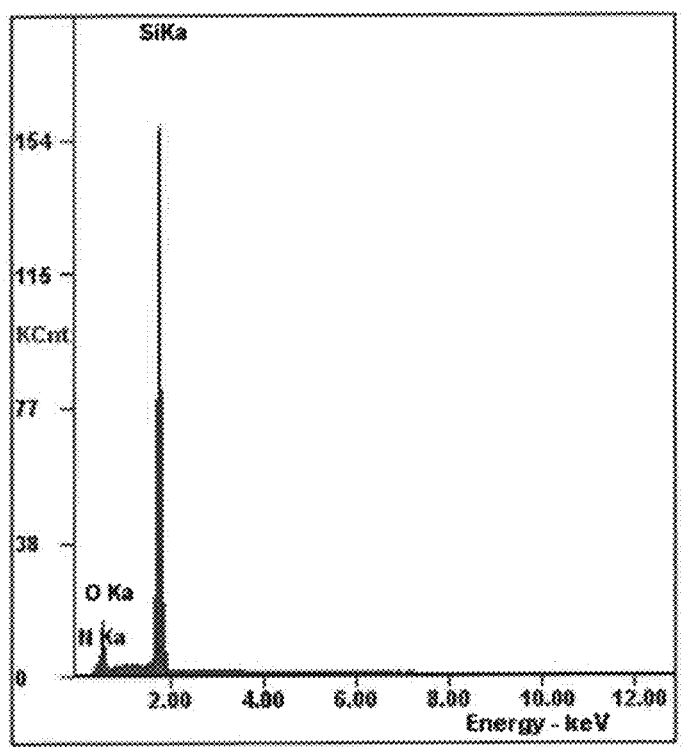
Figure 5:
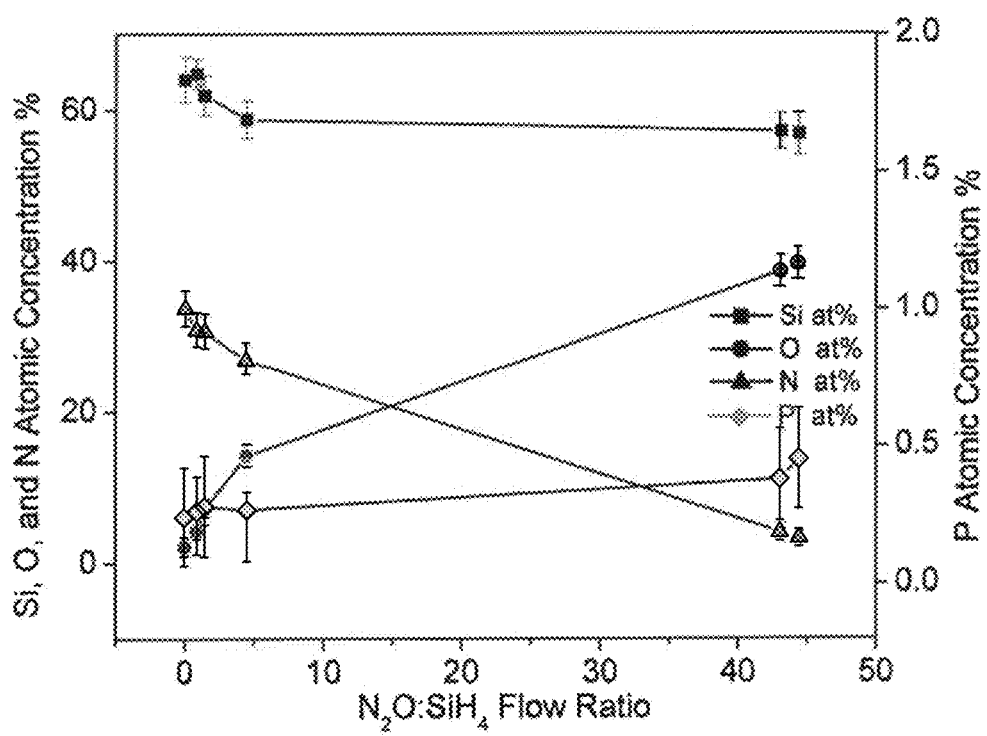
FIG. 5—Atomic composition of SiONPx coatings as determined by EDS spectra as a function of $N_2O:SiH_4$ flow rate. Samples are presented in order from left (Sample 1) to right (Sample 6). Note that phosphorous has been plotted on a secondary axis.

Coating thickness and surface morphology was confirmed by SEM imaging and found to be in agreement with ellipsometry measurements. EDS mapping showed no major carbon or other contaminants and a uniform elemental distribution normal to the wafer surface. A ZAF quantification method was used to determine the atomic % of each element in the coating. FIGS. 4A and 4B show representative spectra of a P-containing and a non-P-containing sample generated under similar conditions, and FIG. 5 shows the coating composition of the SiONPx coatings in terms of atomic % of Si, O, N, and P. Increasing $N_2O:SiH_4$ flow ratio increased oxygen to nitrogen content as well as an unanticipated modest increase in the P content of the coatings. In the sample deposited with 0 sccm $N_2O$ flow, some oxygen is still observed in the coating. This may be due to oxidation of the surface post-deposition, or contamination from the component gases or the deposition chamber itself. For the sample range studied, silicon content was found to be relatively independent of the $N_2O:SiH_4$ flow. The silicon content of the samples was found to be between 56.7-64.7 atomic %.

With these atomic concentrations, the RMM can be applied to calculate the atomic % of each phase in each sample coating, and the RBM can be applied to calculate the coating stoichiometry. Note that the applicability of either model cannot be determined from this data alone. Table 2 shows the RMM and RBM calculated chemistries for each of the coatings.

TABLE 2

RMM and RBM calculations of coating chemical structure according to EDS compositional data

| | RMM (%) | | | | RBM (SizOxNyPw) | | | |
|---|---|---|---|---|---|---|---|---|
| Sample | $SiO_2$ | a-Si | $Si_3N_4$ | $P_2O_5$ | z | x | y | w |
| 1 | 2.3 | 38.1 | 58.8 | 0.85 | 2.56 | 0.08 | 1.35 | 0.010 |
| 2 | 5.4 | 39.9 | 53.8 | 0.87 | 2.59 | 0.17 | 1.23 | 0.010 |
| 3 | 10.0 | 35.7 | 53.4 | 0.98 | 2.48 | 0.29 | 1.22 | 0.011 |
| 4 | 20.3 | 31.9 | 46.9 | 0.95 | 2.35 | 0.57 | 1.07 | 0.011 |
| 5 | 56.4 | 35.2 | 7.1 | 1.33 | 2.28 | 1.54 | 0.16 | 0.015 |
| 6 | 57.7 | 35.1 | 5.6 | 1.58 | 2.27 | 1.58 | 0.13 | 0.018 |

Figure 6:
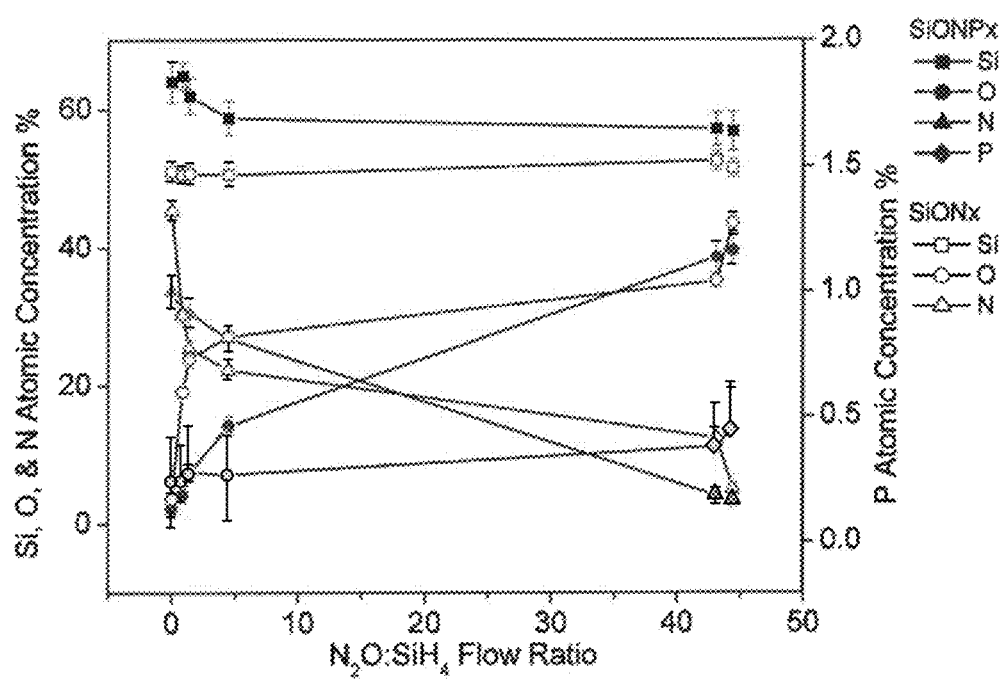
FIG. 6—Comparison of the atomic composition of SiONx and SiONPx coatings fabricated under similar conditions as determined by EDS spectra as a function of $N_2O:SiH_4$ flow rate.

Though both SiONx and SiONPx chemistries show a similar trend in terms of nitrogen and oxygen content as a function of the ratio of the $N_2O:SiH_4$ flow rates, there are important differences between the sample stoichiometries. While it is readily apparent that the SiONPx coatings contain phosphorous while the SiONx coatings do not, a somewhat unanticipated result is that the Si content in terms of atomic % in an SiONPx coating is significantly higher than that of the equivalent SiONx coating. The additional Si content in the SiONPx films may be due to the presence of competing gas phase reactions of phosphine with nitrous oxide.[65] That is, while some oxygen from the $N_2O$ flow reacts before reaching the sample surface, the $SiH_4$ is continuing to deposit a-Si. This has the net effect of slowing O incorporation into the film, and lower O content is observed for all P-deposition conditions with the exception of the highest 160 sccm $N_2O$ flow rate, where the O content is roughly equivalent. FIG. 6 compares the atomic composition of the SiONx and SiONPx coatings deposited under similar conditions.

EDS spectra showed little evidence of non-reaction elemental contamination, and the oxygen and nitrogen content of coating chemistry was found to be dependent on the ratio of nitrous oxide to silane flow rate. Though no carbon contamination was observed, in the coating generated in the absence of nitrous oxide (theoretically the only oxygen source in the PECVD process), [65] oxygen was still observed on the sample surface, which may have been due to the formation of an oxide layer post-process via reaction with air. Surface energy calculations demonstrated the dependence of the polar component of the surface energy on sample chemistry, in particular the nitrogen content of the coating, which has implications for protein adsorption and cell attachment to the surface.[92,93]

Example 4—Surface Energy Evaluation

A sessile drop technique was used to determine contact angles of distilled, deionized water and diiodomethane (>99%, Sigma-Aldrich, St. Louis, Mo., USA) on the wafer coating surface. For each liquid, 9 repeat drops were measured at 25° C. and samples were tested in triplicate. The surface tension of the testing fluids including the polar and dispersive components was taken from literature values at the same experimental conditions and can be seen in Table 3. Surface energy ($\gamma_{LV}$) and its corresponding dispersive ($\gamma^d$) and polar ($\gamma^p$) component values for probing liquids[113,114].

TABLE 3

| Probing fluid | $\gamma_{LV}$ (mJ m$^{-2}$) | $\gamma^d$ (mJ m$^{-2}$) | $\gamma^p$ (mJ m$^{-2}$) |
|---|---|---|---|
| Water | 72.8 | 21.8 | 51.0 |
| Diiodomethane | 50.8 | 50.4 | 0.4 |

The hydrophilicity of the surface was inferred from the contact angle with water and the surface energy values of the samples were obtained by relating the measured probing liquid contact angles (θ) and relating them to solid surface energy dispersive and polar components by the Owens-Wendt-Kaeble equation:

$$\gamma_{LV}(1+\cos\theta)=2(\gamma_L^d\gamma_S^d)^{1/2}+2(\gamma_L^p\gamma_S^p)^{1/2}$$

where subscripts S and L represent solid and liquid surfaces, respectively. Surface roughness measured via SPM imaging indicated that the as-deposited roughness for all sample groups (Ra<1 nm) has no effect on the measurement of equilibrium contact angles.[115, 116, 140]

Figure 7A:
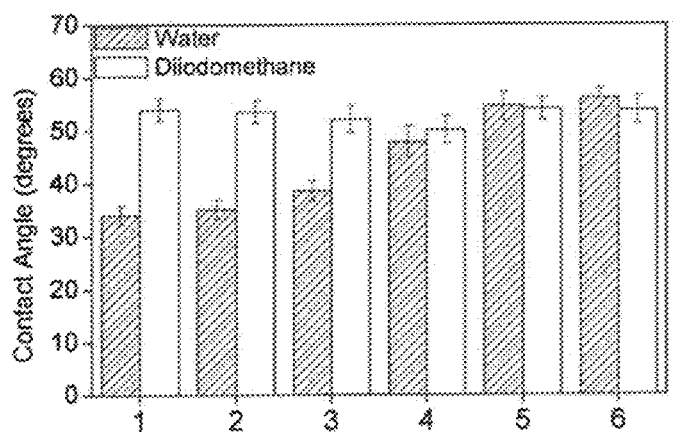
FIG. 7A—Sessile drop contact angle of water and diiodomethane.
Figure 7B:
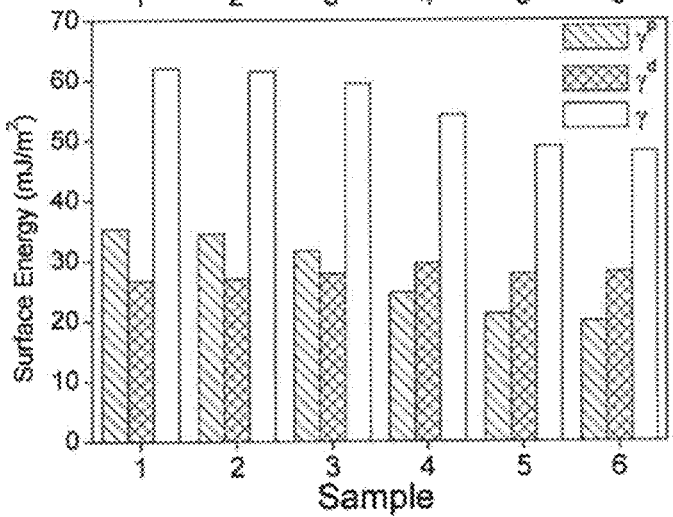
FIG. 7B—calculated surface energy of SiONPx coatings, broken into polar $\gamma^p$ and dispersive $\gamma^d$ components.

The contact angles as determined by a sessile drop technique for the two probing liquids (water and diiodomethane) are shown in FIG. 7A. The water contact angle increases with increasing oxygen content from 34.0±1.3° to 56.1±1.7°. High nitrogen content samples are therefore considered more hydrophilic than the high oxygen samples. Diiodomethane, which is a relatively non-polar probing liquid, and has a contact angle that is relatively constant for these coatings, measured between 50.2±2.1° and 54.1±2.1° which indicates that the dispersive component is relatively constant for these surfaces. Differences observed in the contact angle with water can therefore be primarily attributed to a change in the polar component of the surface energy. FIG. 7B shows the polar ($\gamma^p$), dispersive ($\gamma^p$) and total surface energy (γ) values calculated from the Owens-Wendt-Kaeble equation in mJ/m². The dispersive component for all samples ranges from 26.7 to 28.1 mJ/m² while the polar component varies with nitrogen content. The highest nitrogen content sample (Sample 1) has a polar component of 35.3 mJ/m² while the highest oxygen content sample (Sample 6) has a polar surface energy component of 20.0 mJ/m². The polar surface energy seems to increase as a function of nitrogen content in the sample.

Figure 8:
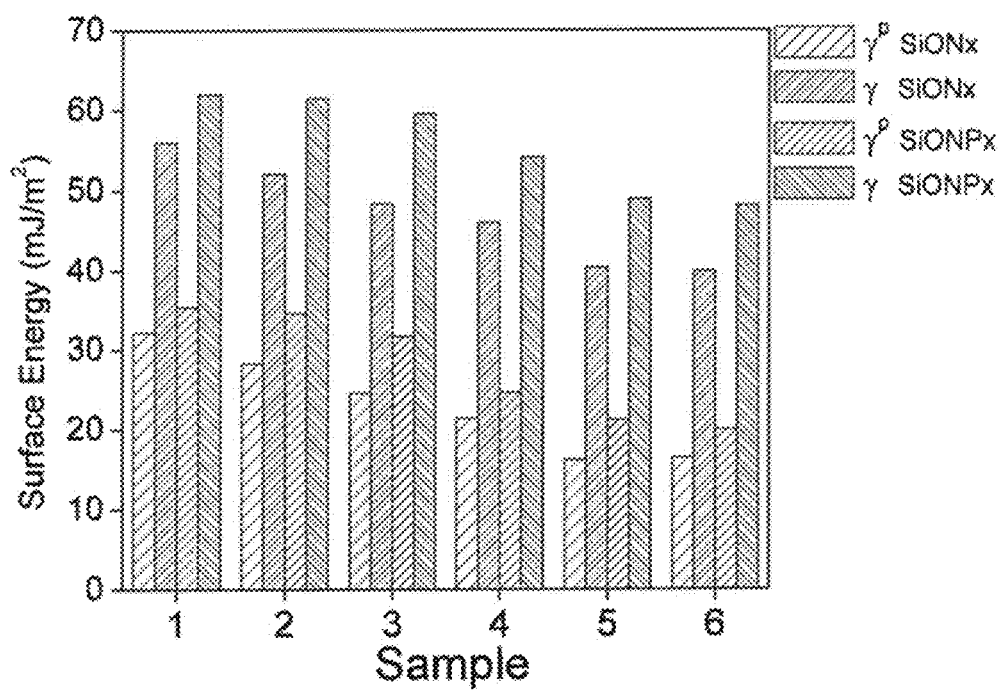
FIG. 8—Comparison of calculated surface energy of SiONx and SiONPx coatings, broken into polar $\gamma^p$ and dispersive $\gamma^d$ components.

In general, the SiONPx chemistries have higher total surface energies than those of the SiONx chemistries. While the dispersive component of the surface energy for all coating surfaces calculated using water and diiodomethane sessile drop contact angles is similar, a greater variability is observed in the polar component of surface energy. The effect of the addition of phosphorous into the coatings on both the polar component of the surface energy and the total surface energy is summarized in FIG. 8, which compares SiONx and SiONPx coatings made under similar conditions.

Example 5—XANES Characterization

XANES spectroscopy was carried out on $SiO_2$ and $Si_3N_4$ model compounds and all six SiONPx coating chemistries. The acquired XANES sample spectra are compared with each other and with the model compounds for silicon (Si), oxygen (O), and nitrogen (N) and phosphorous (P) atoms. The Si- and P-$L_{2,3}$ edge and Si—, O—, and N—, and P—K edges were used to characterize the chemical nature and structural environment of the amorphous coatings. XANES spectra were obtained at the Canadian Light Source (CLS, Saskatoon, Canada) using the Variable Line Spacing Plane Grating Monochromator (VLS-PGM, 11ID-2), the High Resolution Spherical Grating Monochromator (SGM, 11ID-1), and the Soft X-ray Microcharacterization (SXRMB, 06B1-1) beam lines.

Sample sections of 12 mm×12 mm were attached to the sample stage with carbon tape and examined under vacuum. The sample was aligned so that the beam was normal to the sample surface. For the Si- and P-$L_{2,3}$ edges acquired on the VLS-PGM beam line, the total electron yield (TEY) and fluorescence yield (FY) signal was recorded. For the Si—K, O—K and N—K edges acquired on the SGM beam line, TEY and partial fluorescence yield (PFY) data was recorded. For the P—K edge data acquired on the SXRMB beam line, TEY and FY data was recorded with a 1 second dwell time and a step size of 5/1/2 eV for the pre-edge/edge/post-edge spectral features. All sample edges on the SGM and PGM beam lines were acquired with a 1 second dwell time and a step size of 0.5/0.1/0.25 eV for the pre-edge/edge/post-edge spectral features. At least two spectra were acquired per sample per edge. Spectra were energy shifted using reference compounds collected in the same session with well-known peak positions, $Si_3N_4$ nanopowder (Nanostructed & Amorphous Materials Inc, Houston, Tex., USA) and $SiO_2$ (>99.5%, Sigma-Aldrich, St. Louis, Mo., USA). Linear background subtraction was performed using the spectral pre-edge for peak area calculations; however, some spectra are presented without background subtraction for clarity.

Figures 9A, 9B:
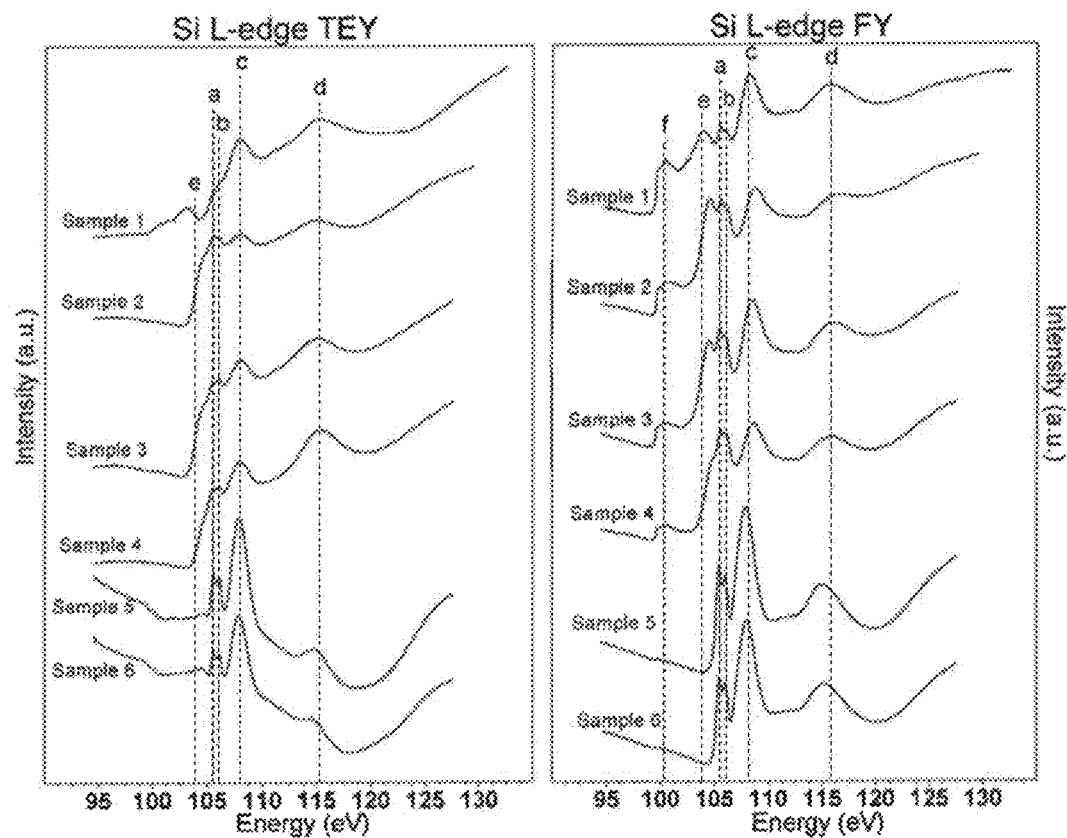
FIGS. 9A and 9B—Silicon $L_{2,3}$-edge TEY and FY XANES spectra of SiONPx coating chemistries (a) and (b) indicate silica tetrahedral structure (c) and (d) indicate $Si^{4+}$ (e) indicates Si—N bonding and (f) indicates the presence of Si—Si bonding.

XANES Silicon $L_{2,3}$-Edge:

The Silicon Si-$L_{2,3}$ edge can be used to investigate both the chemical species that give rise to changes in binding energies as well as to distinguish between four-fold and six-fold coordination of Si.[119] Silicon Si-$L_{2,3}$ spectra were acquired from 95-130 eV using the VLS-PGM beamline. FIGS. 9A and 9B show the TEY and FY data for the six SiONPx sample chemistries. The TEY data can be considered to be collected from the near-surface ~5 nm while the FY data contains information from more of the bulk coating ~70 nm. [120] Six peaks of interest have been identified and labeled a-f. Peaks a and b at 105.5±0.1 eV and 106.1±0.1 eV, respectively, arise due to the transition of 2p electrons to unoccupied 3d orbitals that have been split by ~0.6 eV by spin-orbital splitting.[119, 120] The ratio of these peaks has been used to differentiate the contribution from disparately substituted $SiO_4$ tetrahedra.[103] That is, the a:b integrated peak area ratio can be used as a semi-quantitative measure of nitrogen substitution into a $SiO_4$ tetrahedron. Table 4 shows the calculated a:b peak area ratio for both the TEY and FY signals for the $SiO_2$ and $Si_3N_4$ model compounds and six sample coatings. The a:b peak area ratio FY data suggests that while the silica tetrahedron structure may provide a useful approximation of the Si—O and Si—N bonding in the lower nitrogen containing samples 5 and 6, the high nitrogen content samples (1-4) may form a structure better approximated by that of the β-$Si_3N_4$ standard. The a:b peak area ratio TEY data suggests that all of the higher nitrogen content samples form a surface silica layer that has little nitrogen content.

The highest intensity peak c is the found in both standards and all samples is the main Si $L_{2,3}$-edge peak, and its position can be used to distinguish between fourfold ([4]Si) and six-fold ([6]Si) coordinated silicon in silicate glasses.[103, 121] For [4]Si, the main peak is centered at 107.9±0.2 eV while in [6]Si an additional main edge peak is observed at 106.7±0.2 eV.[123] In FIGS. 9A and 9B, the peak c line is centered at 108.0±0.2 eV indicating that [4]Si is found in all samples and standards. Second order derivative fitting of Samples 1 through 4, however, indicates that there may be a peak centered near 106.8 eV which would be an indication that a mix of $^{[4]}$Si and $^{[6]}$Si is present in these chemistries. Peak d centered at 115.3±0.2 eV is a resonance Si-peak found in both $Si_3N_4$ and $SiO_2$ and therefore cannot be used to distinguish between the chemical finger print of either structure. Peak e is characteristic of Si—N resonance bonding[124], and is found centered at 103.2±0.2 eV for the $Si_3N_4$ standard. This peak is observed to shift to higher energies in high-N content samples: for the FY data, it is found at 103.9±0.2 eV (Sample 1), 104.5±0.2 eV (Sample 2), 104.5±0.2 eV (Sample 3), and 104.9±0.2 eV (Sample 4) which indicates an increasing distortion of the Si—N bond in a nitride matrix.[124] For samples 5 and 6, where it is not observed, the structure of the Si may be better described as an $SiO_2$-like matrix with limited Si—N bonding occurring and fit into a silica tetrahedral-like structure. Peak f at 99.7±0.2 eV is found in all samples, though the intensity of the main edge peak makes it difficult to ascertain in Samples 5 and 6. This peak has previously been observed in other SiONx coatings with excess Si and is attributed to Si—Si bonding in silicon nanoclusters (Si-nc) found within the coating.[124] It is also possible that this peak arises from the contribution of the underlying Si wafer since it is seen more prominently in the FY data, which has a higher escape volume in terms of signal that reaches the detector.

TABLE 4

Integrated peak area ratios for peak a to peak b in Si $L_{2,3}$-edge of $Si_3N_4$, $SiO_2$, and six sample coating chemistries

| Sample | EDS Compositional data (at %) | | | | a:b peak area ratio TEY | a:b peak area ratio FY |
|---|---|---|---|---|---|---|
| | Si | O | N | P | | |
| $Si_3N_4$ | 43.8 | 0.8 | 55.3 | — | 1.73 | 1.73 |
| 1 | 64.0 | 2.1 | 33.7 | 0.24 | 0.84 | 1.65 |
| 2 | 64.8 | 4.2 | 30.8 | 0.25 | 1.02 | 1.68 |
| 3 | 61.8 | 7.3 | 30.5 | 0.28 | 0.98 | 1.71 |
| 4 | 58.7 | 14.2 | 26.8 | 0.27 | 0.97 | 1.51 |
| 5 | 57.1 | 38.6 | 4.0 | 0.38 | 1.18 | 1.13 |
| 6 | 56.74 | 39.6 | 3.26 | 0.45 | 1.12 | 1.08 |
| $SiO_2$ | 32.2 | 67.8 | 0.0 | — | 1.02 | 1.02 |

Silicon L-edge data collected support the theory that the high-oxygen content SiONPx sample coating chemistries 5 and 6 can be well-described as N-substituted silica tetrahedrons ($^{[4]}$Si) according to the RBM view of the structure. The high-nitrogen content samples, however, maybe be better described using a RMM view of the bonding structure.

XANES Silicon K-Edge

Figure 10:
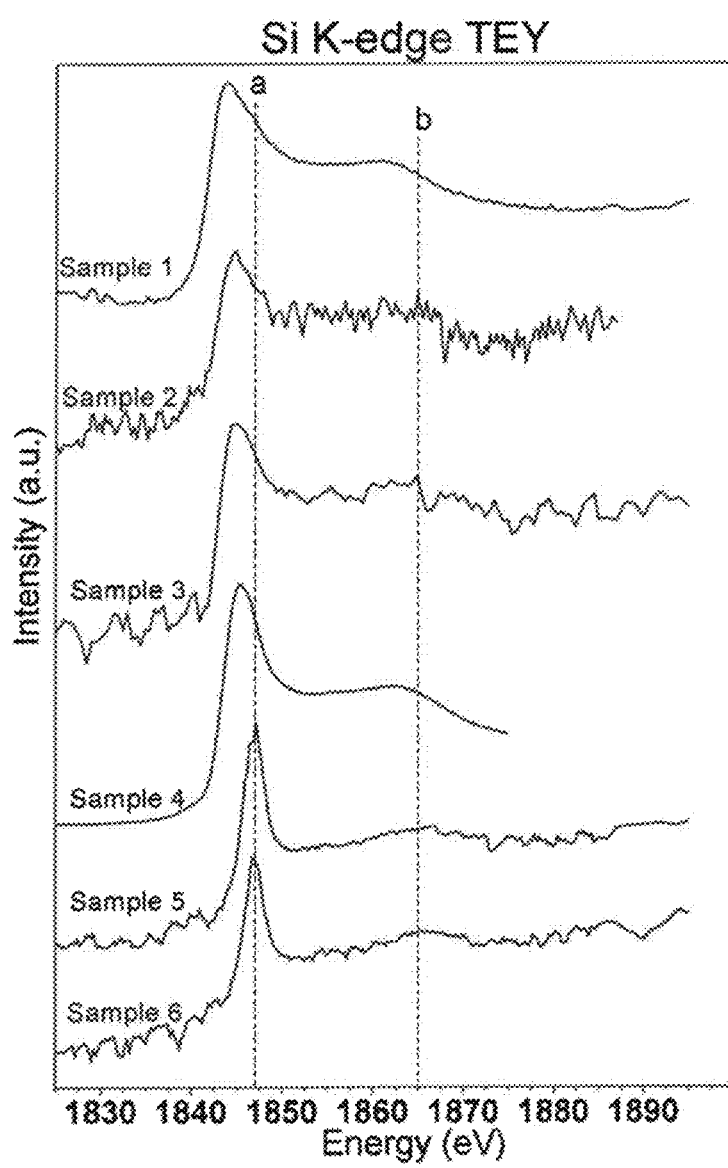
FIG. 10—Silicon K-edge XANES spectra of six SiONPx coating chemistries main line peak broad spectral contributions are attributed to Si—Si, Si—O, and Si—N bonding.

The Silicon Si—K edge can also be used to investigate chemical changes and structural changes in silicon.[119] Silicon Si—K edge spectra were acquired from 1820-1890 eV using the SGM beam line. FIG. 10 shows the Si K-edge TEY data for the 6 SiONPx sample chemistries. This TEY data can be considered to be collected from the near-surface ~70 nm.[120] There are two main peaks of interest in these spectra: peak "a", the main Si K-edge peak around 1847±0.3 eV and a post edge peak b feature common to all spectra around 1864.8±0.2 eV. Peak a can be thought of as the sum total contribution of Si—Si bonding (~1841 eV), Si—N bonding (~1844.5 eV) and Si—O bonding (1847 eV) resonances.[124] In the $Si_3N_4$ standard, some oxygen contamination is observed and the peak is split between Si—N and Si—O resonant energies. The high-N content samples, on the other hand, show evidence of all three bonding fours with a leading edge around 1841 eV and a broad absorption peak encompassing both Si—N and Si—O resonant energies. The high-O content samples show primarily Si—O bonding, with a small spectral contribution around 1841 eV, suggesting some Si—Si bonding occurring. The $SiO_2$ standard peak "a" edge, in contrast, is centered at 1847±0.3 eV and has a leading edge at 1843±0.3 eV, which is well above the energy level suggesting Si—Si bonding.

XANES Oxygen K-Edge

Figures 11A, 11B:
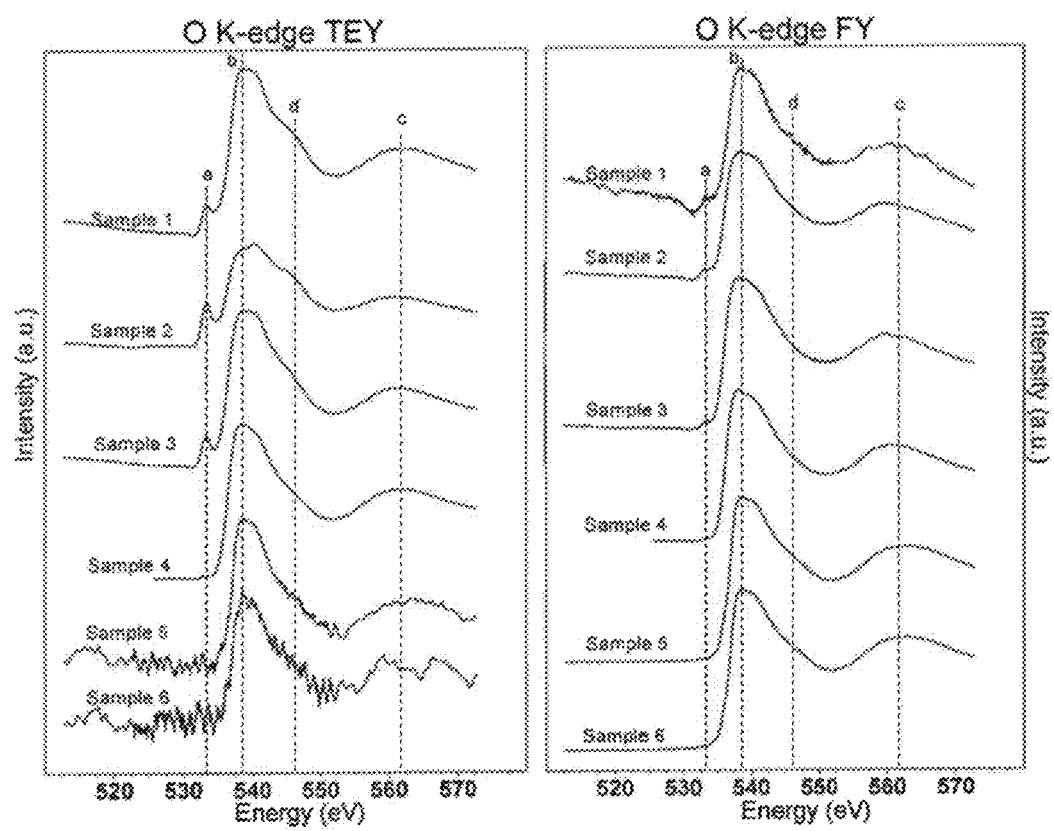
FIGS. 11A and 11B—Oxygen K-edge XANES TEY and FY spectra of six SiONPx coating chemistries (a) shows evidence of Si—OH type bonding while post edge features (b), (c) and (d) show evidence of Si—O bonding.

The Oxygen K-edge can be used to investigate local oxygen structure. All O—K edge spectra were acquired from 525-585 eV using the SGM beam line. FIGS. 11A and 11B show the O K-edge TEY and FY data for the 6 sample chemistries. The TEY data for this edge can be considered to be collected from the near-surface (~25 nm) while the FY data contains information from a deeper interaction area of about ~150 nm. There are four main peaks observed in these spectra: peak a, a pre-edge peak around 529.9±0.2 eV, the main O—K edge peak b around 535.2±0.2 eV, a post edge peak c feature around 558.5±0.2 eV, and a post-edge shoulder peak d around 546.2±0.2 eV. Peak a is observed as a distinct peak in the lower oxygen content sample chemistries (samples 1, 2, and 3) in both the TEY and FY data. The presence of this peak in the FY data may suggest either non-bridging Si—O bonds in the bulk of the coating, or it may be attributed primarily to the surface region where post-processing oxidation is believed to occur which would greatly influence any measurement of low-oxygen content sample chemistries, particularly in the TEY data. The primary oxygen bonding in the higher oxygen content samples can be attributed to Si—O—Si bridges, as evidenced by the main peak b and post-edge resonance peak c.[125] The strong post-edge shoulder peak "d", which is prominent in the low oxygen content samples, may be attributed to the interaction of N—Si—O bonding and the distortion of the $SiO_2$ network in the high nitrogen content chemistries, which is prominent in the TEY spectra of these samples, again suggesting the presence of a post-process oxide forming.

XANES Nitrogen K-Edge

Figures 12A, 12B:
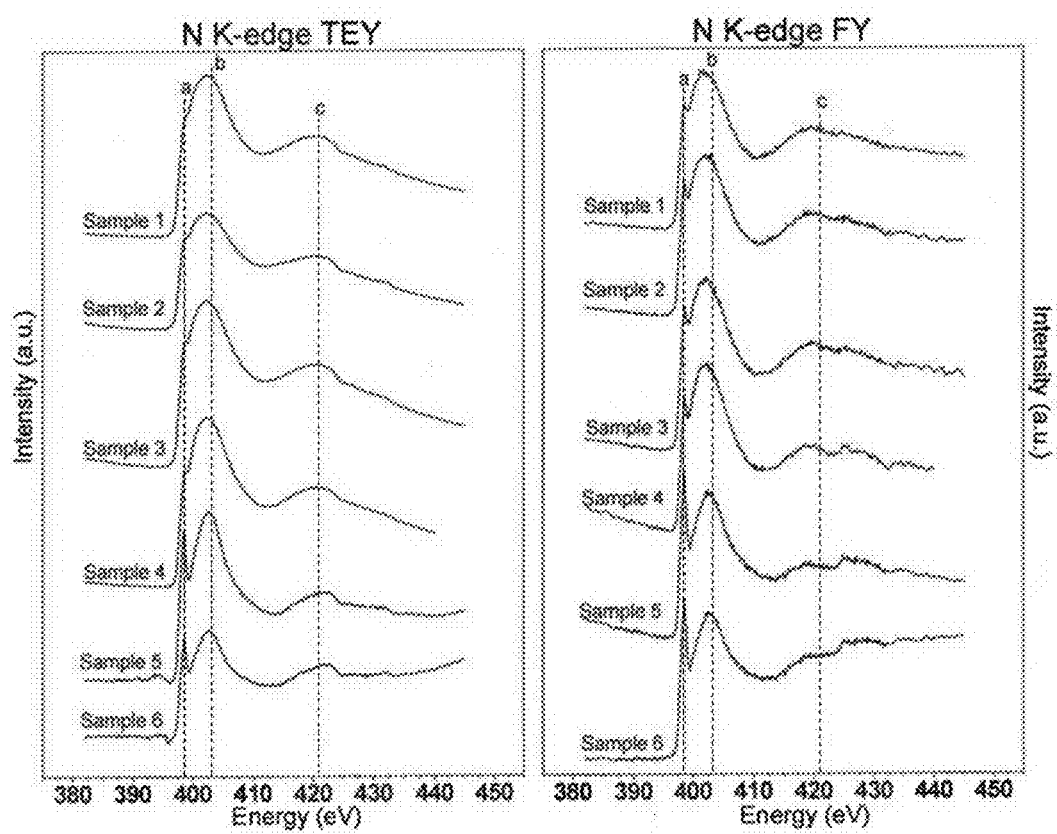
FIGS. 12A and 12B—Nitrogen K-edge XANES TEY and FY spectra of six SiONPx coating chemistries showing the presence of 2-fold coordinated nitrogen (peak a).

The Nitrogen K-edge can be used to investigate local nitrogen structure. All N—K edge spectra were acquired from 380-450 eV using the SGM beam line. FIGS. 12A and 12B show the N K-edge TEY and FY data for the six sample chemistries. The TEY data can be considered to be collected from the near-surface (~20 nm) while the FY data contains information from a deeper interaction area of about ~125 nm. There are three main peaks observed in these spectra: peak "a" around 398.6±0.2 eV, the main peak "b" around 402.6±0.2 eV, and a post edge peak "c" feature around 421.4±0.2 eV.

Peak was attributed to the presence of under-coordinated (i.e. two-fold coordinated) or hydrogen-bound nitrogen which indicates either the presence of N—H bonding or the substitution of a nitrogen atom for an oxygen atom into a Si—O—Si bridge; it is sometimes referred to as the resonance line (RL).[125, 126] While this peak is particularly prominent in the TEY spectra of the lowest-N containing samples 4 and 5, it can also be observed as a pre-edge shoulder in the other, higher-N content TEY spectra. The apparent increased intensity of the peak in the low-N sample 5 and 6 chemistries suggests that a proportionately larger amount of N in these samples is 2-fold coordinated, or, conversely, that the Si—O—Si bridge network remains relatively undisturbed by the limited amount of N incorporation into the coating. In the FY bulk data, this peak "a" is observed as a distinct feature in all chemistries. The main edge peak b is similar for all samples and the $Si_3N_4$ standard, suggesting that the bulk of the spectral contribution is due to Si—N bonding. The post edge peak c resonance, however, appears distorted in the lower-N content sample 4 FY data and the sample 5 and 6 TEY and FY data. The peaks observed between 425 eV-435 eV in these spectra may be due to a higher order spectral contribution from silica, which overwhelms the N signal in these relatively Si-rich and N-poor coatings.

XANES Phosphorous $L_{2,3}$-Edge

Figure 13:
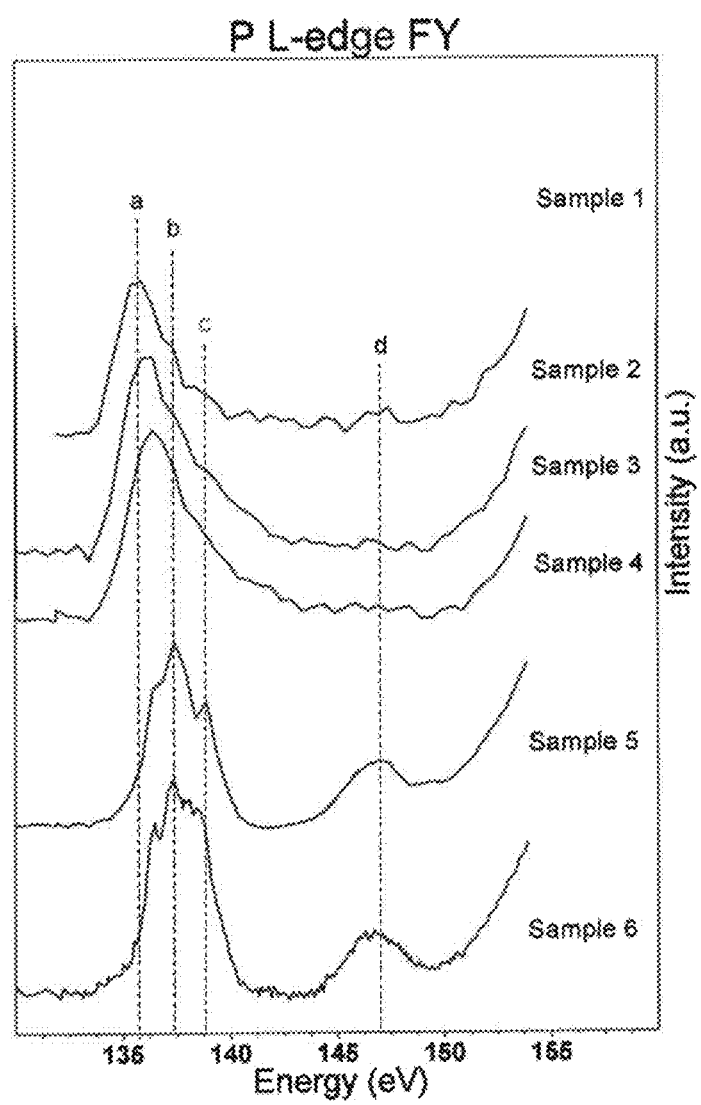
FIG. 13—Phosphorous $L_{2,3}$-edge XANES FY spectra of five SiONPx coating chemistries peaks (a) and (b) show the presence of phosphorous while peaks (c) and (d) suggest phosphate-like P—O bonding.

Though the other element edges give little evidence of phosphorous content (particularly in the form of P—O bonding) in the film due to the relatively low atomic content, the tunability of this XANES technique allows for the direct probing of the phosphorous $L_{2,3}$-edge to investigate local phosphorous structure. All P $L_{2,3}$-edge spectra were acquired from 130-155 eV using the PGM-VLS beam line. FIG. 13 shows the P $L_{2,3}$-edge FY data for six sample chemistries. The P-L edge FY data contains information from an interaction depth of about ~75 nm. There are four main peaks observed in these spectra: peak a, around 135.7±0.2 eV, peak b around 137.4±0.2 eV, peak c around 138.8±0.2 eV and a post edge peak d feature around 147.0±0.2 eV.

The transitions in L edge spectra follow distinct patterns, and the less well-studied P-L edge spectral features have been compared to the better understood Si-L edge spectra.[104] Like in silica L-edge spectra, in the P $L_{2,3}$-edge peaks a and b are proposed to arise from the transition from 2p electrons (spin-orbit split into $2p_{3/2}$ and $2p_{1/2}$ levels) to the lowest unoccupied 3s-like antibonding state.[135] Peak c has been attributed to a transition to a 3p-like antibonding state in the presence of oxygen, and peak d is considered to arise from 2p to 3d transitions.[136] Since the exact location and intensity of these peaks is extremely sensitive to local chemical structure, the P $L_{2,3}$-edge allows for the investigation of P-substitution into a $Si_3N_4$ or $SiO_2$-like coating.

From FIG. 13, two distinct P chemistries are observed. Sample 1 spectra could not be obtained due to issues with contamination, though other data (P K-edge) suggests that it would be similar in nature to samples 2-4. Samples 2, 3, and 4 have a broad peak near the peak a position which has a post edge shoulder at peak b. Though this peak appears to shift to slightly higher energy with increasing oxygen content, second derivative peak fitting indicates that the a and b peak positions do not change and instead the relative contribution of the a:b peaks changes. Notably absent are any spectral contributions from peak c or peak d—both of which are only allowed transitions when P is bound to a more electronegative atom like oxygen. The absence of these peaks would seem to indicate that the majority of the phosphorous in these coatings in not bound to oxygen, and may instead be bound primarily to other phosphorous atoms in an amorphous tetra-phosphorous or hydrated-phosphorous state. This lack of P—O phosphate bonding is somewhat unexpected due to the presence of oxygen in these coatings and the relative stability of the phosphate ion to that of tetra- or hydrated-phosphorous under sample fabrication conditions. In the highest oxygen content samples 5 and 6, however, all four peaks are observed: peaks a and b as one broad peak, peak c as a post-edge shoulder, and peak d as a distinct post-edge feature. In these samples, spectral features indicate that phosphorous is present in the form of phosphate ions.

XANES Phosphorous K-Edge

Figures 14A, 14B:
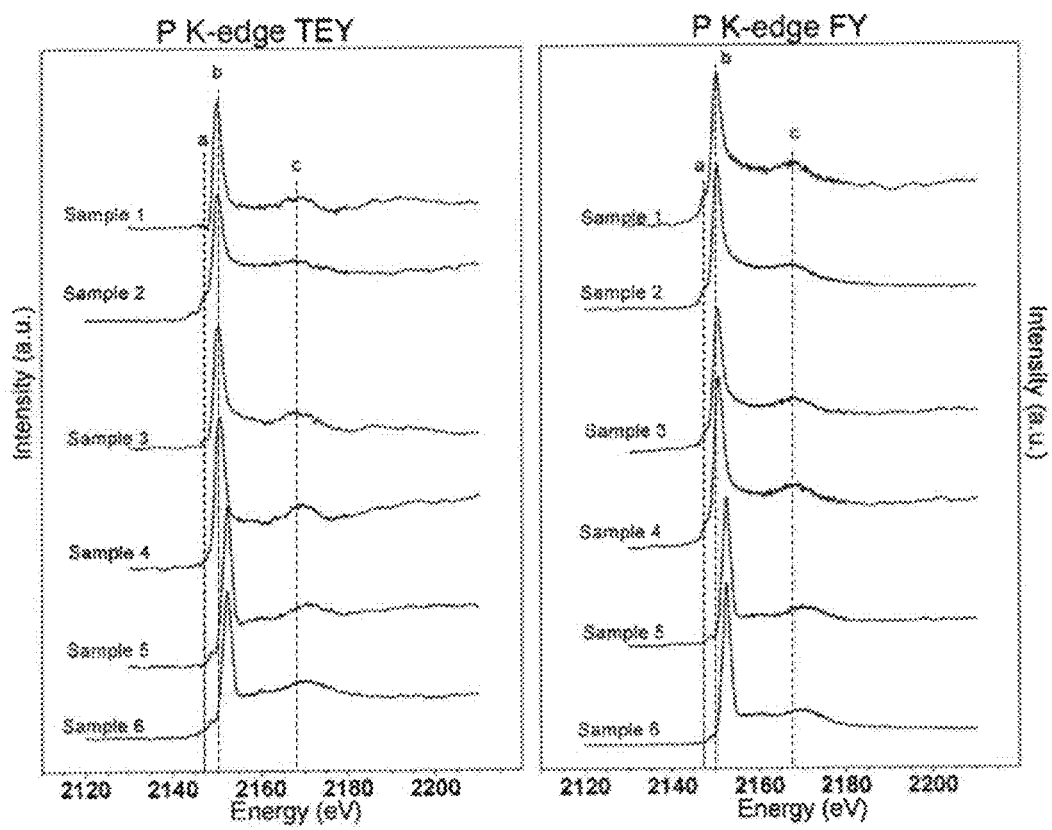
FIGS. 14A and 14B—Phosphorous K-edge XANES TEY and FY spectra of six SiONPx coating chemistries pre-edge peak (a) pre-edge data may indicate P—H bonding (b) main line energy shifts indicate changes Si—P and P—O type bonding while post edge resonance (c) is seen in all phosphorous bonding.

The Phosphorous K-edge can also be used to investigate local phosphorous structure. All P—K edge spectra were acquired from 2120-2240 eV using the SXRMB beam line. FIGS. 14A and 14B show the P K-edge TEY and FY data for six sample chemistries. Due to the higher energy of the probing beam, both TEY and FY data can be considered to be collected from the bulk of the coatings. The contribution of the substrate, which is 99.9% Si, to the phosphorous spectra is negligible, and therefore both sets of data are presented as representative of the coating. There are three main peaks observed in these spectra: a pre-edge peak a, around 2147.4±0.4 eV, the main peak b around 2150.2±0.3 eV, and a post edge peak c feature around 2168.1±0.4 eV.

The Phosphorous K-edge spectra indicate 2 main phosphate chemistries: one common to samples 1, 2, 3, and 4 and a different phosphorous chemistry in the high-oxygen content samples 5 and 6. The similarity of sample 1 to samples 2, 3, and 4 supports the idea that the P $L_{2,3}$-edge features observed for sample 1 in FIG. 13 are due to contamination, rather than the sample itself. Since the K-edge data is less sensitive to surface contamination, the P—K spectra can be considered more representative of the sample coating chemistry absent of surface contamination effects. In the low oxygen content samples, peak a, a pre-edge resonance peak, is observed in both the TEY and FY data, though it is more distinct in the FY data, which is most likely a function of detector sensitivity. Peak b, the main line peak, is down-shifted over 2 eV from that of structures containing phosphates, where the main line peak is observed around 2152.4±0.4.[141, 142] This shift would seem to indicate that there is little to no P—O phosphate bonding in these chemistries, in agreement with the P L-edge data. For samples 5 and 6, however, the main line peak b is observed at 2152.5±0.4, in good agreement with previous measurements of phosphosilicate glasses, where phosphorous is predominantly observed in the form of the phosphate ion.[142]

XANES Si L-edge, Si K-edge, O K-edge, N K-edge, P L-edge, and P K-edge spectra were acquired for six coating chemistries: two high-nitrogen content samples, two intermediate oxygen/nitrogen content samples and two high-oxygen content samples. These samples were compared to each other and to silicon oxide and silicon nitride standards to investigate the chemical structure of the SiONPx coatings formed. Two distinct SiONPx chemical structures emerge from an investigation into these XANES spectra.

The higher nitrogen content sample coatings, Sample 1, Sample 2, Sample 3, and Sample 4, resemble one another with a few key differences. The Si L-edge a:b peak ratio remains close to that of $Si_3N_4$ for these samples which suggests that Si—N bonding environment is similar to the nitride standard, however, peak e, which is attributed to Si—N bonding, shifts to higher energy with decreasing nitrogen content. This energy shift suggests that the Si—N bond is increasingly distorted as oxygen is incorporated into the system. This distortion—or high energy bonding structure—may contribute to increased instability of this bond pair in the physiological environment which would result in a relatively rapid reaction in vitro or in vivo. The broad main peak a in the Si—K edge spectra for these samples also suggests that Si—O and Si—N bonding both exist in forms similar to the silica Si—O bonding and the nitride Si—N bonding structures simultaneously since the broad peak overlaps with both of the standards. This spectral feature likely indicates a mixture of both distorted silicon nitride-type and distorted silicon oxide-type bonding structures in these coatings. The presence of the peak a pre-edge in the O K-edge spectra shows evidence of silanol bonding in these coatings, which may allow for bioactive remodeling of these coatings in a physiological environment similar to the process through which known bioactive glass formulations form mineral in vitro and in vivo. The sharp resonance line peak a in the N K-edge indicates the presence of undercoordinated or hydrogen bound nitrogen in these samples, which should prove to more readily react with the physiological environment than 3-fold coordinated nitrogen found in pure silicon nitride. Both the P L-edge and P K-edge spectra for these sample chemistries do not show any evidence of phosphate type P—O bonding, and the P in these samples therefore believed to be in a relatively unstable form, which may contribute to rapid dissolution in an in vitro or in vivo environment.

The highest oxygen content sample coatings, Sample 5 and Sample 6, on the other hand, seem to have formed coatings with a different chemical structure from that of the low oxygen coatings. The Si L-edge a:b peak ratio of these chemistries remains close to that of SiO2 which suggests that Si—O bonding environment is similar to that of silica. The narrow main peak a in the Si K-edge spectra for these samples also suggests that silica-like Si—O bonding dominates the structure. The absence of the peak a pre-edge in these O K-edge spectra indicates that there is little evidence of silanol bonding in these coatings. The strong presence of the sharp resonance peak a in the N K-edge data suggests that much of the nitrogen in these coatings considered 'undercoordinated'—and most likely substituted into the place of a bridging oxygen atom, which would occur in systems where the silica tetrahedra is the basic structural unit. P L-edge and P K-edge data also indicate that phosphorous is found predominately in the form of a phosphate-like bonding structure in these coatings.

Since the RMM was found to model the high nitrogen content samples while the RBM was found to better model the high oxygen content samples, Table 3 can be revised to reflect the actual coating chemistries observed from the XANES edges, with one exception: in the high nitrogen content samples, the P-incorporation does not take the form of phosphorous pentoxide ($P_2O_5$) as originally assumed by the model since the P $L_{2,3}$ edge and P K-edge show no evidence of P—O bonding in these chemistries. Therefore the P-incorporation into these coatings will be approximated as elemental P, instead of $P_2O_5$. Table 5 summarizes the coating chemical structures found in this study as modeled by the random mixing model or random bonding model.

TABLE 5

Modified RMM validated for high-nitrogen type chemistries and RBM validated for high oxygen content chemistries

| Sample | Modified RMM (%) | | | | RBM ($Si_zO_xN_yP_w$) | | | |
|---|---|---|---|---|---|---|---|---|
| | $SiO_2$ | a-Si | $Si_3N_4$ | P | z | x | y | w |
| 1 | 3.2 | 37.7 | 58.9 | 0.24 | | | | |
| 2 | 6.3 | 39.6 | 53.8 | 0.25 | | | | |
| 3 | 11.0 | 35.4 | 53.4 | 0.28 | | | | |
| 4 | 21.27 | 31.5 | 46.9 | 0.27 | | | | |
| 5 | | | | | 2.28 | 1.54 | 0.16 | 0.015 |
| 6 | | | | | 2.27 | 1.58 | 0.13 | 0.018 |

Example 6—Fabrication and Evaluation of SiONPx Coatings for Degradation Study

A PECVD process was used to form a coating using a silicon wafer with a silica sublayer as a substrate. Briefly, <1 0 0> p-type test grade Si wafers (Nova Electronic Materials, Flower Mound, Tex.) were obtained and a TRION ORION II PECVD/LPCVD system was used to coat the wafers with 100 nm of $SiO_2$ and 100 nm of an Si—O—N—P amorphous coating via a PECVD (plasma enhanced chemical vapor deposition) process. All coatings were fabricated at a substrate temperature of 400° C., chamber pressure of 900 mTorr, an ICP power of 75 W with a 13.56 MHz excitation frequency applied. Source gases included a silane ($SiH_4$) and phosphine ($PH_3$) mixture diluted in argon (Ar) (15%/2%/83%), nitrous oxide ($N_2O$), nitrogen ($N_2$), and ammonia ($NH_4$). The silane flow rate was kept low at 24 sccm (15% $SiH_4$) to prevent undesirable gas-phase reactions. The nitrogen and ammonia flow rates were kept high at 225 sccm and 50 sccm, respectively, to try and increase the nitrogen (and N—H as well as Si—H) content of the films. Six different coating chemistries were prepared by varying the nitrous oxide flow rate as seen in Table 6. For further characterization and experimentation, wafers were then cut into 12 mm×12 mm sample sections using a Disco DAD3220 Automatic Dicing Saw.

TABLE 6

Gas flow rates for silicon oxynitride layer deposition

| | Gas Flow Rates (sccm) | | | |
|---|---|---|---|---|
| Sample | 15% $SiH_4$/2% $PH_3$/83% Ar | $N_2O$ | $N_2$ | $NH_3$ |
| 1 | 24 | 0 | 225 | 50 |
| 2 | 24 | 3 | 225 | 50 |
| 3 | 24 | 5 | 225 | 50 |
| 4 | 24 | 16 | 225 | 50 |
| 5 | 24 | 155 | 225 | 50 |
| 6 | 24 | 160 | 225 | 50 |

The amorphous nature of the coatings was confirmed by XRD spectra through the use of a Bruker D8 Advance diffractometer to collect Bragg-Brentano scans using Cu kα radiation ($\lambda$=1.5418 Å) at room temperature. The atomic compositions of the coating chemistries were then determined by EDS measurement.

The refractive indices and the thickness of the wafer coatings were measured using ellipsometry at a wavelength of 632.8 nm (Gaertner LS300), and results were confirmed through the use of a reflectometer (Ocean Optics NC-UV-VIS TF Reflectometer) and a scanning electron microscope (Hitachi S-3000N VP SEM). The thickness for all coatings was found to be 100 nm±2 nm with an in-wafer non-uniformity for all chemistries of 2.5-3%.

Additionally, EDS measurements were taken of the initial coating chemistry composition. Table 7 lists the sample chemistries in terms of atomic %. The low-nitrous oxide flow samples (Sample 1 and Sample 2) have less oxygen while the high-nitrous oxide flow samples (Sample 5 and Sample 6) are relatively oxygen rich and nitrogen poor. The intermediate flow rate samples (Sample 3 and Sample 4) have intermediate oxygen and nitrogen content.

TABLE 7

Atomic composition of SiONPx coatings at t = 0 as determined by EDS measurement

| | EDS Compositional data (at %) | | | |
|---|---|---|---|---|
| Sample | Si | O | N | P |
| 1 | 64.0 | 2.1 | 33.7 | 0.24 |
| 2 | 64.8 | 4.2 | 30.8 | 0.25 |
| 3 | 61.8 | 7.3 | 30.5 | 0.28 |
| 4 | 58.7 | 14.2 | 26.8 | 0.27 |

TABLE 7-continued

Atomic composition of SiONPx coatings at t = 0
as determined by EDS measurement

| Sample | EDS Compositional data (at %) | | | |
|---|---|---|---|---|
| | Si | O | N | P |
| 5 | 57.1 | 38.6 | 4.0 | 0.38 |
| 6 | 56.74 | 39.6 | 3.26 | 0.45 |

Six distinct SiONPx chemistries were fabricated via a repeatable PECVD process designed to create potentially bioactive phosphorous-incorporated silicon oxynitride coatings. These coatings ranged from oxygen-poor silicon oxynitride (for coatings produced at low nitrous oxide flow rates between 0-16 sccm) to nitrogen-poor silicon oxinitride (for coatings produced at high nitrous oxide flow rates 155 and 160 sccm).

Example 7—ICP-OES

ICP-OES analysis was performed at the Shimadzu Center for Advanced Analytical Chemistry using the Shimadzu ICPE-9000 ICP-OES system. 12 mm×12 mm wafer sections were placed in 4 mL of α-MEM at 37° C. and 5% $CO_2$ for 0, 0.5, 1, 2, 4, 8, 12, 24, 96, and 192 hours. After the set immersion time, 25×, 50× and 100× dilutions were used to investigate salt content in the supernatant fluid. Aluminum was used as an internal standard, and calcium, phosphorous, and silica concentration measurements were taken from the α-MEM dissolution media in order to evaluate the surface degradation kinetics of the coatings and the precipitation of calcium phosphates out of solution and onto the wafer surface. Single-element high purity ICP Ca, Al, Si, and P standards (1000 μg/L) were purchased from Ultra Scientific.

Figure 15:
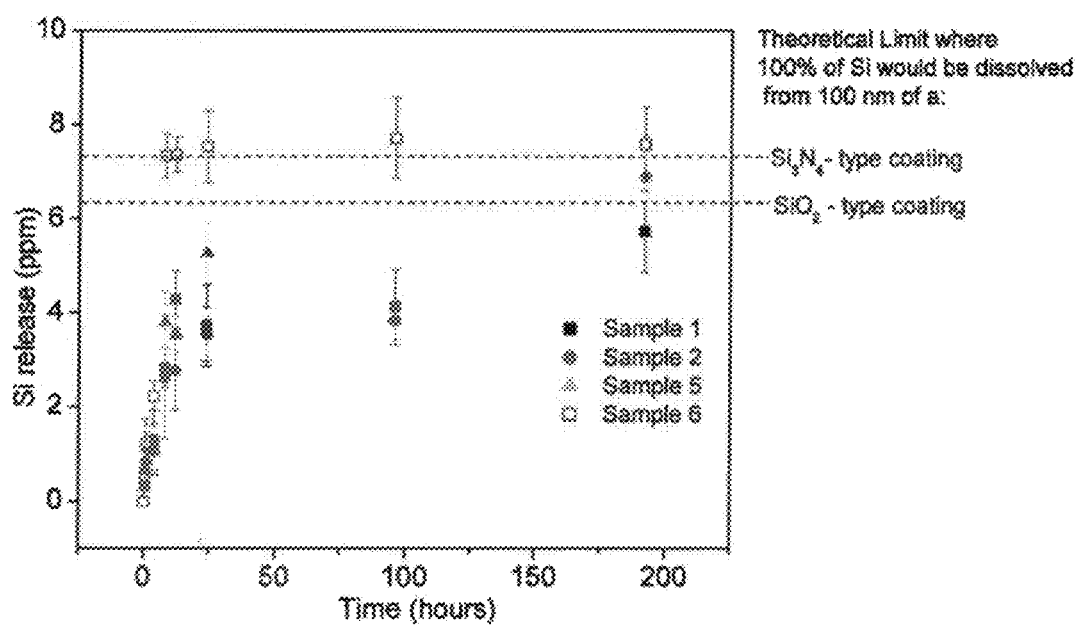
FIG. 15—Silicon release from four SiONPx sample chemistries immersed in αMEM as determined by ICP-OES analysis.

Inductively coupled plasma optical emission spectra were used to evaluate the release of Si from 12 mm×12 mm sample sections immersed in 4 mL of αMEM and incubated for 0, 0.5, 1, 4, 8, 12, 24, 96, and 192 hours. Calcium and phosphorous concentrations were also investigated to determine if any calcium phosphates precipitated out of the αMEM solution and onto the sample surface. FIG. 15 shows the silica release into the αMEM solution for sample 1, 2, 5 and 6 chemistries.

Initially, there is little silica in αMEM solution, however, all samples rapidly (<30 mins) begin to release silica into solution. Sample 6 appears to undergo the most rapid release and completely releases all silica after 8 hours in solution. Sample 5 appears to completely releases all silica after 96 hours in solution while samples 1 and 2 only appear to mostly release their silica after 192 hours in solution. The higher oxygen-content samples appear to have more rapid release rates than the low oxygen content samples. It should be noted that the higher oxygen content samples also contain more phosphorous, which is known in bioactive glass formulations to help control dissolution rate.[143]

It is instructive to look at silica release in tends of the percentage of the thickness of the coating dissolved; however, in order to estimate this quantity some simplifying assumptions must be made. First of all, the coatings are assumed to be chemically and structurally uniform in the direction normal to the surface. Secondly, since the exact densities of the coatings are unknown, a reasonable approximation would be to use the density of similar low-temperature fabricated PECVD coatings. According MIT's material property database, low-temperature PECVD deposited silica has a density of about 2.3, $g/cm^3$ [133] while similarly fabricated nitride has a density of about 2.5 $g/cm^3$.[133] Since these coatings have a known composition that is intermediate to these two extremes, these values can be used to calculate the total amount of silica that is able to go into solution and a % of coating thickness lost as a function of time can be determined. Table 8 lists coating thickness remaining for four of the sample chemistries as a function of time in dissolution calculated according to this method.

TABLE 8

Sample coating thickness remaining after immersion in αMEM determined by Si release

| Time (hours) | Thickness Remaining (nm) | | | |
|---|---|---|---|---|
| | Sample 1 | Sample 2 | Sample 5 | Sample 6 |
| 0 | 100.0 | 100.0 | 100.0 | 100.0 |
| 0.5 | 95.0 | 93.4 | 95.8 | 92.1 |
| 1 | 83.4 | 88.1 | 82.6 | 82.4 |
| 4 | 81.7 | 84.4 | 85.1 | 68.3 |
| 8 | 59.7 | 62.6 | 45.8 | −4.9 |
| 12 | 38.8 | 60.4 | 49.5 | −5.2 |
| 24 | 46.8 | 49.4 | 24.6 | −7.6 |
| 96 | 41.1 | 45.3 | −10.2 | −10.2 |
| 192 | 18.0 | 1.4 | −10.1 | −8.3 |

Negative values indicate that more silica is found in solution than is found in the original SiONPx coating; this may be due to a limited amount of silica release from the exposed silica layer underneath the coating itself but is it likely due to the error in the sample measurement. This treatment of the data shows that the highest nitrogen content sample 1 is most likely the only coating that has not completely dissolved after 8 days in solution.

Figure 16:
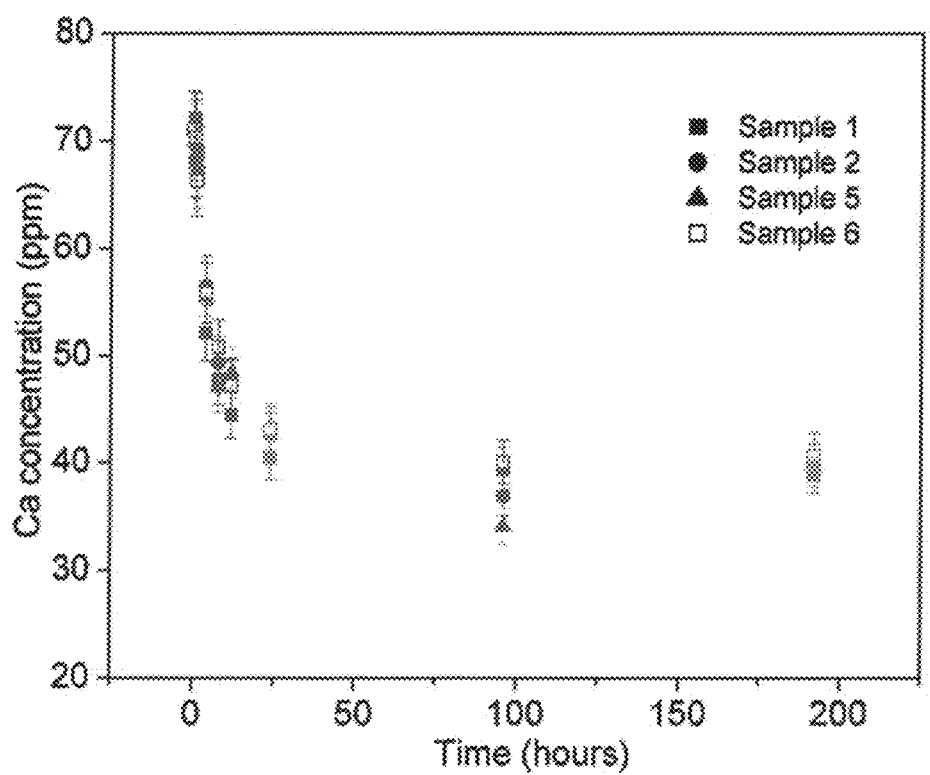
FIG. 16—Ca loss from αMEM for four SiONPx sample chemistries immersed in solution as determined by ICP-OES analysis.
Figure 17:
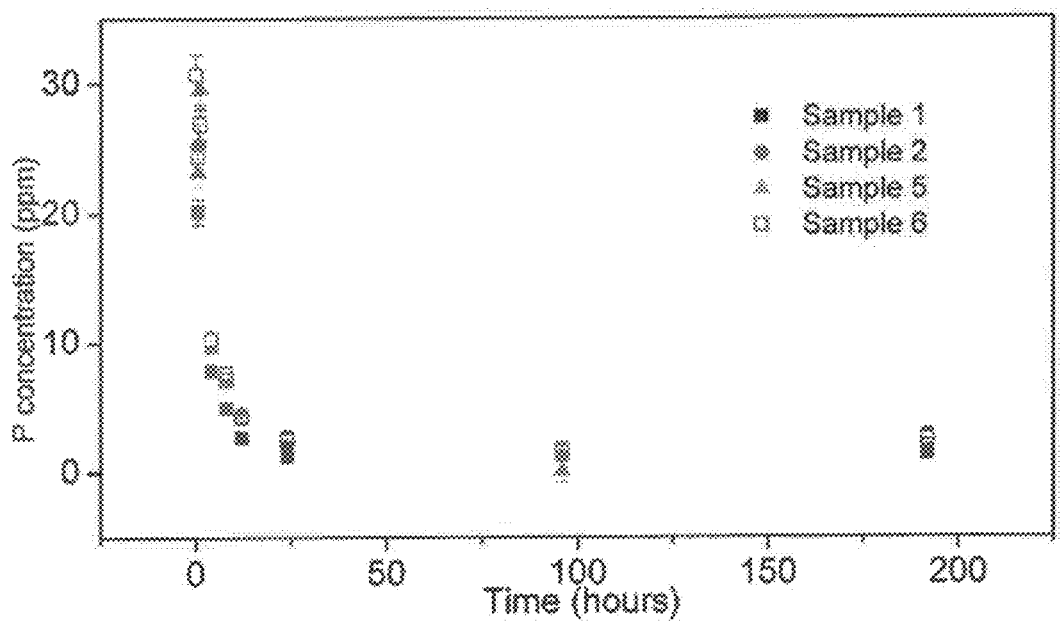
FIG. 17—P loss from αMEM for four SiONPx sample chemistries immersed in solution as determined by ICP-OES analysis.

The loss of calcium and phosphorous from the αMEM soaking solution were also determined by ICP-OES analysis. The calcium results from this analysis can be seen in FIG. 16. The phosphorous concentration in the αMEM solution over a period of 8 days can be seen in FIG. 17.

According to manufacturer specifications, αMEM contains 72.2 ppm Ca and 31.3 ppm P. The αMEM used in this experiment was found to have 71.2±0.8 ppm Ca and 31.0±1.0 ppm P, in relatively good agreement with the manufacturer's specifications. Looking at both the calcium and phosphorous profiles together, it would appear that both follow approximately the same kinetic trend for all sample chemistries, suggesting that both elements are precipitating out of solution simultaneously independent of sample chemistry. After about 24 hours of immersion, the Ca and P content in solution appear to reach a steady state for all samples investigated.

Though direct observation of the products of a precipitation reaction using ICP-OES spectra is difficult, the calcium and phosphorous data can be combined to assess the possibility of a given chemistry precipitating out of solution. Pure apatite, the major mineral component of bone, has a calcium to phosphorous (molar) ratio of 1.67:1. In bioactive glass systems, it is well understood that the initial apatite formation that occurs on the glass surface is not in the form of a stoichiometric apatite but rather in the form of a poorly crystalline carbonate-substituted apatite where the Ca:P ratio can vary from 1.6:1 to 1.5:1.[134] Therefore if the predominant calcium and phosphate species formed combine to form an apatite-like structure, the cumulative ratio of the loss of Ca ppm to P ppm from solution should be between 1.9:1 and 2.1:1. Table shows the Ca:P ppm loss ratios calculated from the calcium and phosphorous data. In all samples for all time points, more calcium is lost from solution that could be bound in an apatite-like precipitate, suggesting that if there is formation of an apatite-like precipitate on the sample surfaces, there is also the formation of other calcium species, though all samples appear to show similar Ca:P ratios after 4 days in solution.

TABLE 9

Cumulative Ca:P loss ratio from αMEM as a function of immersion time

| Time | Ca:P ppm ratio | | | |
|---|---|---|---|---|
| (hours) | Sample 1 | Sample 2 | Sample 5 | Sample 6 |
| 0.5 | −0.1 | 0.5 | 0.2 | 0.1 |
| 1 | 0.6 | 1.0 | 1.8 | 1.2 |
| 4 | 0.8 | 0.7 | 0.7 | 0.7 |
| 8 | 0.9 | 0.9 | 1.0 | 0.9 |
| 12 | 0.9 | 0.9 | 0.9 | 0.9 |
| 24 | 1.0 | 1.0 | 1.0 | 1.0 |
| 96 | 1.1 | 1.2 | 1.2 | 1.1 |
| 192 | 1.1 | 1.1 | 1.1 | 1.1 |

ICP-OES measurements showed that the Si release from the surface may be a function of the nature of the sample chemistry, and that the high oxygen content samples completely dissolve more rapidly while the high nitrogen content samples dissolve less-readily. Calcium and phosphorous concentration measurements suggest that these species precipitate out of solution in a manner independent of sample chemistry.

Example 8—SEM Imaging

Surface topology, initial film composition, initial film thickness, and surface microstructure of coatings after 6 hours and 8 days immersion in αMEM at 37° C. in a humidified atmosphere with 5% $CO_2$ were investigated using scanning electron microscopy (Hitachi S-3000N Variable Pressure SEM) equipped with an energy dispersive X-ray spectrometry system (EDAX). SEM images were taken with an acceleration voltage of 20 keV and scans for EDX mapping and compositional studies were taken at 12 keV to prevent interference from sub-coating layers. EDAX software was used to quantify spectral mapping data from 50 μm×50 μm areas.

SEM imaging was used to investigate the coating conformity as well any changes in the microstructure of the surface due to degradation in αMEM. A look at the surface on the micro-scale is particularly instructive since the microstructure clearly shows whether there are indications of the formation of calcium phosphate microcrystals, which form on the surface of bioactive glasses after immersion in a simulated body fluid.[88]

Figure 18:
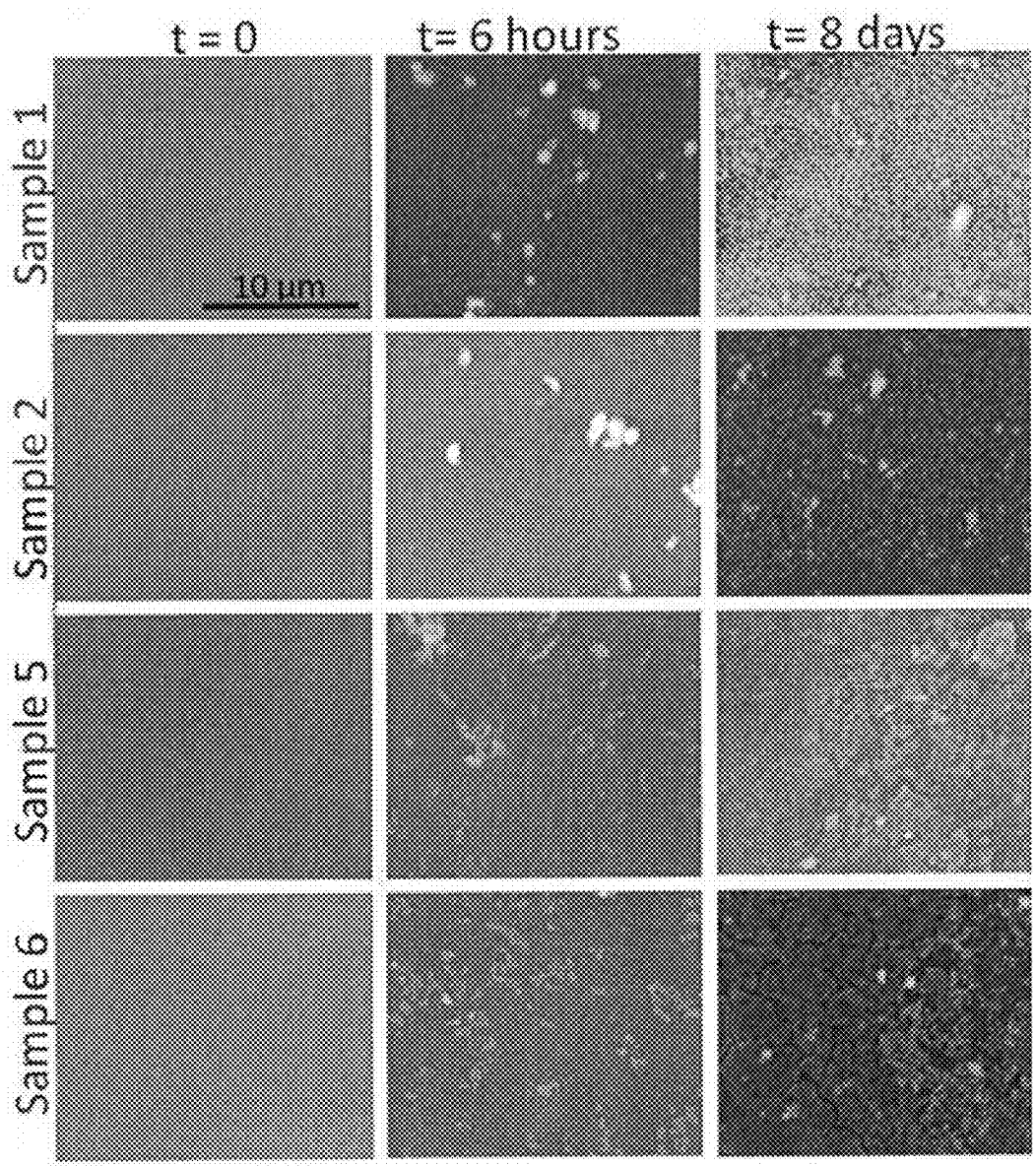
FIG. 18—Microcrystal formation is observed on four SiONPx chemistry surface after immersion in αMEM. All images taken at 5kx, WD=15.0 mm, 20 kV, in BSE-COMPO mode.
Figure 19A:
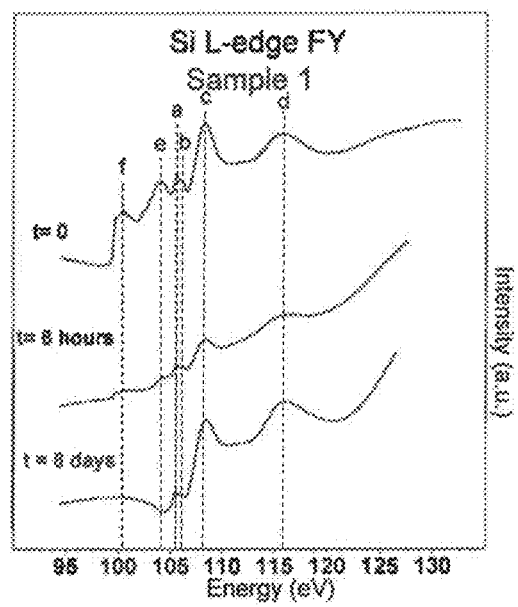
FIG. 19A—Silicon L-edge XANES FY spectra of Sample 1 and FIG. 19B of Sample 2 high-nitrogen content SiONPx coating chemistries at t=0, 6 hours, and 8 days (a) and (b) indicate silica tetrahedral structure (c) and (d) indicate $Si^{4+}$ (e) indicates Si—N bonding and (f) indicates the presence of Si—Si bonding.
Figure 19B:
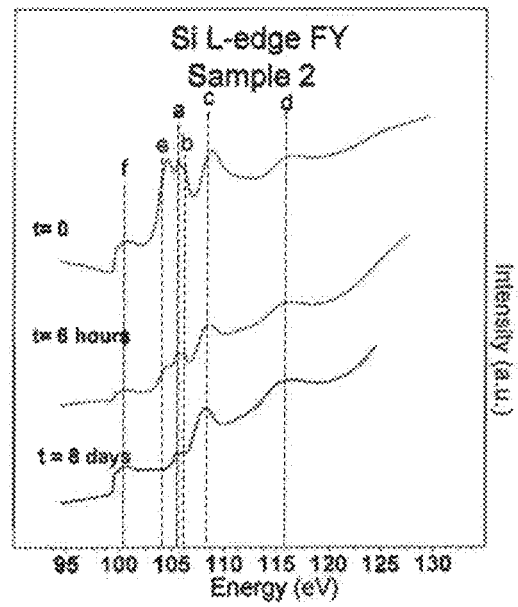
Figure 20A:
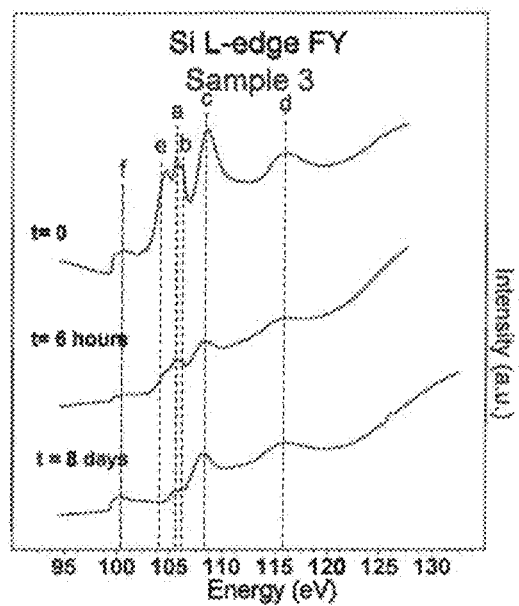
FIG. 20A—Silicon L-edge XANES FY spectra of Sample 3 and FIG. 20B of Sample 4 intermediate nitrogen and oxygen content SiONPx coating chemistries at t=0, 6 hours, and 8 days (a) and (b) indicate silica tetrahedral structure (c) and (d) indicate $Si^{4+}$ (e) indicates Si—N bonding and (f) indicates the presence of Si—Si bonding.
Figure 20B:
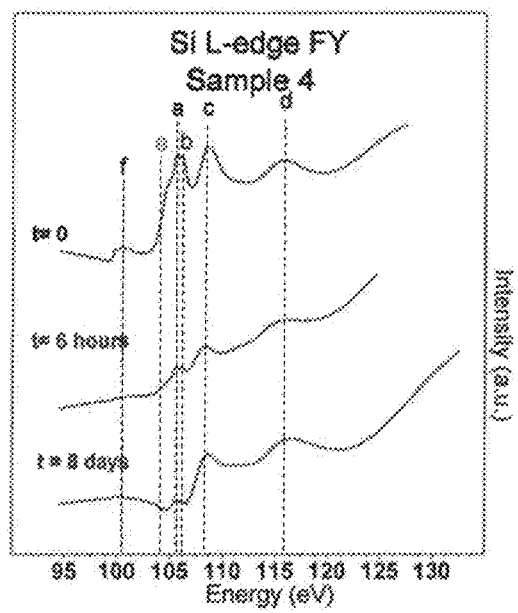

FIG. 18 shows top-down backscattered electron micrographs (in COMPO mode) of the surface of four sample chemistries at time 0, 6 hours, and 8 days. For all chemistries, precipitates form on the surface within six hours of immersion. The higher nitrogen content samples 1 and 2 form relatively large precipitates, on the order of ~1 μm while the surface shows evidence of pitting, perhaps due to the dissolution of the coating. The higher oxygen content sample surfaces 5 and 6 form clusters of smaller precipitates on the order of ~0.1 μm after 6 hours immersion. After 8 days in solution, all surfaces are covered with solution precipitates. In the lower nitrogen content samples they remain discontinuous while in the higher oxygen content samples the surface is covered with a more continuous network. In fact, highest oxygen content sample 6 surface shows evidence of cracking, which most likely occurred during the drying process for SEM imaging preparation. Though crystalline silica and silica nitride are both known not to be bioactive, both the amorphous silica-like samples 5 and 6 as well as the more amorphous nitride-like samples 1 and 2 show evidence of microcrystal formation.[133] This suggests that the more disordered, phosphorous incorporated samples are capable of forming a silica gel layer and precipitating calcium phosphates on the surfaces.

SEM images show evidence of micro-scale precipitate structures on all samples after 6 hours. After 8 days in solution, these microstructures appear to coat the entire sample surface.

Example 9—XANES Characterization

Method: XANES spectroscopy was carried out on the six sample chemistries at three time points: after processing (t=0), after 6 hours of immersion in αMEM and after 8 days of immersion in αMEM. The acquired XANES sample spectra are compared with each other by looking at silica (Si), oxygen (O), nitrogen (N), calcium (Ca), and phosphorous (P) atoms. The Si-, Ca-, and P-$L_{2,3}$ edges and Si—, O—, and N—K edges were used to characterize the chemical nature and structural environment of the amorphous coatings. XANES spectra were obtained at the Canadian Light Source (CLS, Saskatoon, Canada) using the Variable Line Spacing Plane Grating Monochromator (VLS-PGM, 11ID-2) and the High Resolution Spherical Grating Monochromator (SGM, 11ID-1) beam lines.

Sample sections of 12 mm×12 mm were attached to the sample stage with carbon tape and examined under vacuum. The sample was aligned so that the beam was normal to the sample surface. For the Si-$L_{2,3}$ and P-$L_{2,3}$ edges acquired on the VLS-PGM beam line, the total fluorescence yield (FY) signal was recorded. For the Si—K, Ca-$L_{2,3}$ O—K and N—K edges acquired on the SGM beam line, total electron yield (TEY) and partial fluorescence yield (PFY) data was recorded. All sample edges were acquired with a 1 second dwell time and a step size of 0.5/0.1/0.25 eV for the pre-edge/edge/post-edge spectral features. At least two spectra were acquired per sample per edge. Spectra were energy shifted using reference compounds collected in the same session with well-known peak positions, $Si_3N_4$ nanopowder (Nanostructed & Amorphous Materials Inc, Houston, Tex., USA) and $SiO_2$ (>99.5%, Sigma-Aldrich, St. Louis, Mo., USA). Linear background subtraction was performed using the spectral pre-edge for peak area calculations; however, spectra without background subtraction are presented here for clarity.

Silica $L_{2,3}$-Edge

The Silica Si-$L_{2,3}$ edge can be used to investigate the changes in silica chemical structure over time. Silica Si-$L_{2,3}$ spectra were acquired from 95-130 eV using the VLS-PGM beamline. FIGS. 19A and 19B, FIGS. 20A and 20B and FIGS. 21A and 21B show the FY data for the six SiONPx sample chemistries at time t=0, 6 hours, and 8 days. This data can be considered to be collected from the near-surface ~70 nm.[120] Six peaks of interest have been identified and labeled a-f. Peaks a and b at 105.5±0.1 eV and 106.1±0.1 eV, respectively, arise due to the transition of 2p electrons to unoccupied 3d orbitals that have been split by ~0.6 eV by spin-orbital splitting and do not observe shifts in energy due to the chemical bonding environment of a silica atom.[119, 121]

The highest intensity peak c that is found in all samples is the main Si $L_{2,3}$-edge peak, and its position can be used to distinguish between fourfold ($^{[4]}$Si) and sixfold ($^{[6]}$Si) coordinated silica in silicate glasses.[103, 121] For $^{[4]}$Si, the main peak is centered at 107.9±0.2 eV while in $^{[6]}$Si an additional main edge peak is observed at 106.7±0.2 eV.[123] In the Si-L edge figures, the peak c line is centered at 108.0±0.2 eV for all samples at all time points indicating that $^{[4]}$Si is found in all samples both before and during immersion. The decrease in peak c intensity is likely due to the formation of the microcrystal structures on all of the sample surfaces after immersion. Peak e is characteristic of Si—N resonance bonding[124], and is found centered at 103.2±0.2 eV for a $Si_3N_4$ standard. This peak is observed a time zero to shift to higher energies in high-N content Samples 1 (104.0±0.2 eV) and 2 (104.7±0.2 eV) which indicates a distortion of the Si—N bond in a nitride matrix.[124] This peak is not observed to shift after 6 hours of dissolution in Samples 1, 2, 3, and 4 though it is reduced in intensity relative to the main Si L-edge peak. After 8 hours, the peak disappears entirely, suggesting that no more nitrogen is bound in the upper levels of the sample surface to silica, though it may be present bound to another elemental species or deeper in the surface. Peak f at 99.7±0.2 eV is found initially in all samples, though the intensity of the main edge peak makes it difficult to ascertain in Samples 5 and 6. This peak has previously been observed in other SiONx coatings with excess Si and is attributed to Si—Si bonding in silica nanoclusters (Si-nc) found within the coating.[124] This peak is found to increase in intensity after 8 days in samples 2, 3, 5 and 6 suggesting either that the precipitate network that forms on these coatings is discontinuous or that it includes precipitating species with Si—Si bonding.

Silica K-Edge

Figures 22A, 22B:
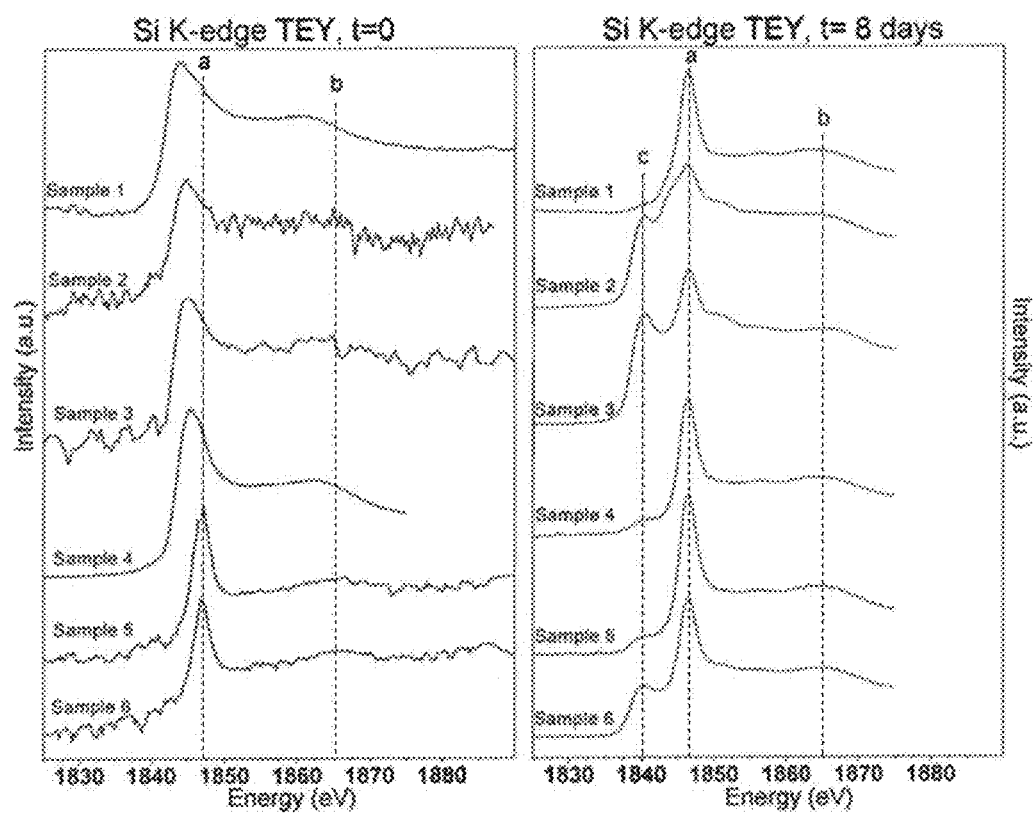
FIG. 22A—Silicon K-edge XANES TEY spectra of six SiONPx coating chemistries at t=0 and FIG. 22B at t=8 days (a) main line peak broad spectral contributions are attributed to Si—Si, Si—O, and Si—N bonding pre-edge (b) is likely due to crystalline Si—Si bonding from substrate.
Figure 23A:
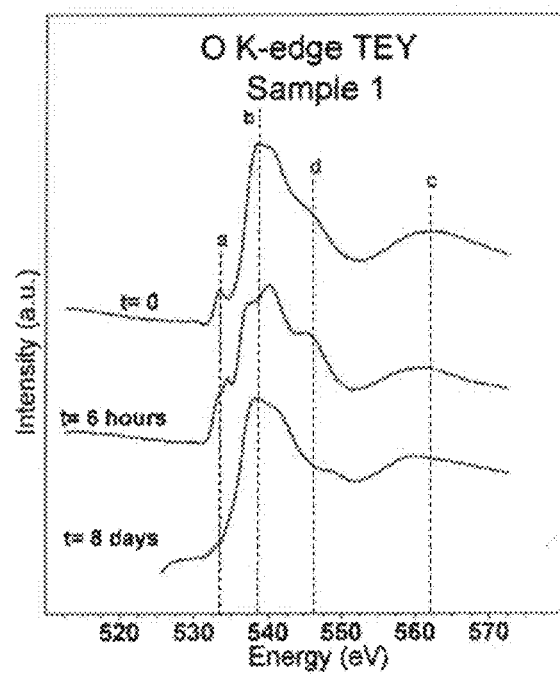
FIGS. 23A and 23B—Oxygen K-edge XANES TEY and FY spectra of Sample 1 and FIGS. 23C and 23D of Sample 2 low-oxygen SiONPx coating chemistries weak pre-edge (a) shows evidence of Si—OH type bonding while a strong pre-edge (a) may indicate carbonate bonding, post edge features (b), (c) show evidence of Si—O bonding while (d) shows evidence of phosphate bonding.
Figure 23B:
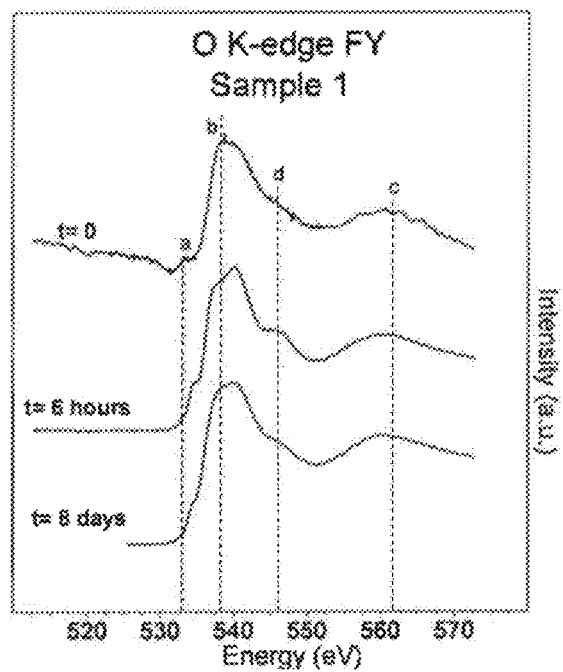
Figure 23C:
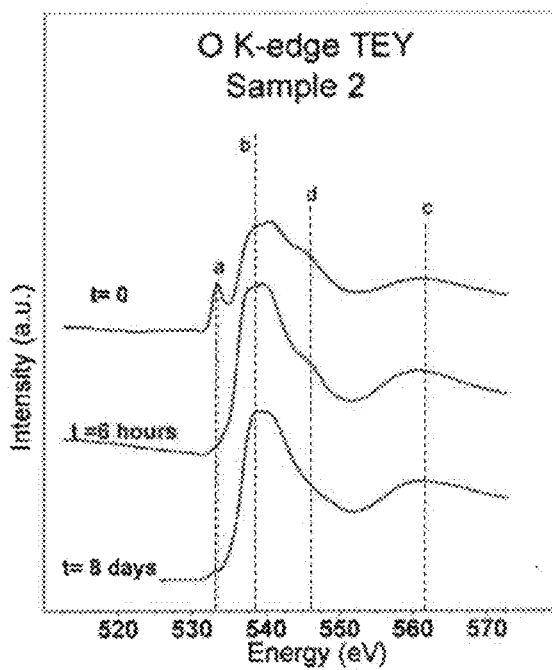
Figure 23D:
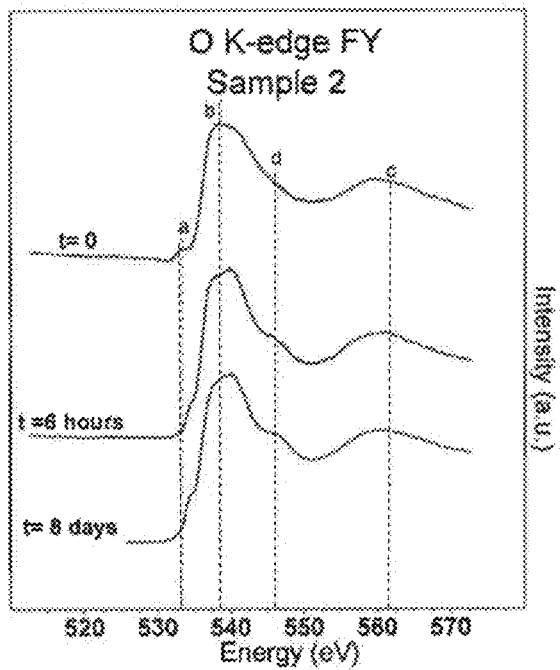
Figure 24A:
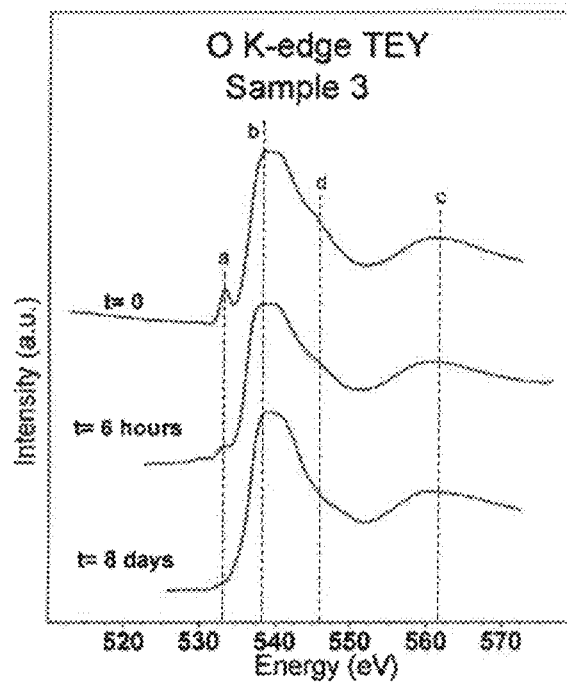
FIGS. 24A and 24B—Oxygen K-edge XANES TEY and FY spectra of Sample 3 and FIGS. 24C and 24D of Sample 4 intermediate nitrogen and oxygen SiONPx coating chemistries weak pre-edge (a) shows evidence of Si—OH type bonding, post edge features (b), (c) show evidence of Si—O bonding while (d) shows evidence of phosphate bonding.
Figure 24B:
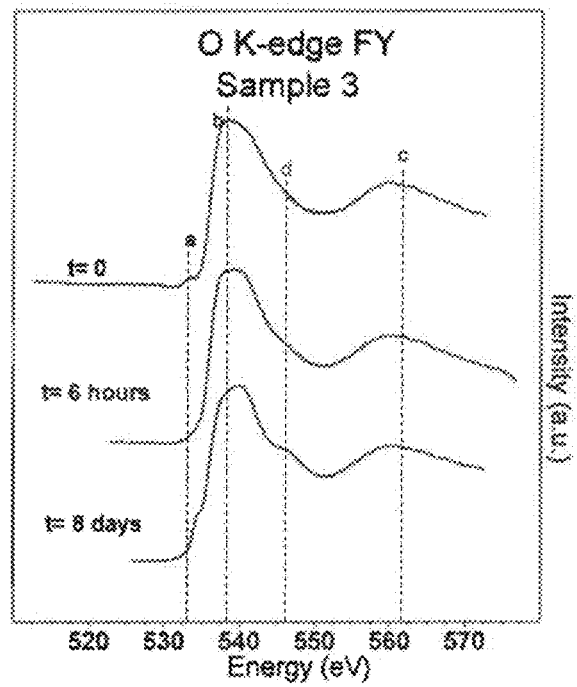
Figure 24C:
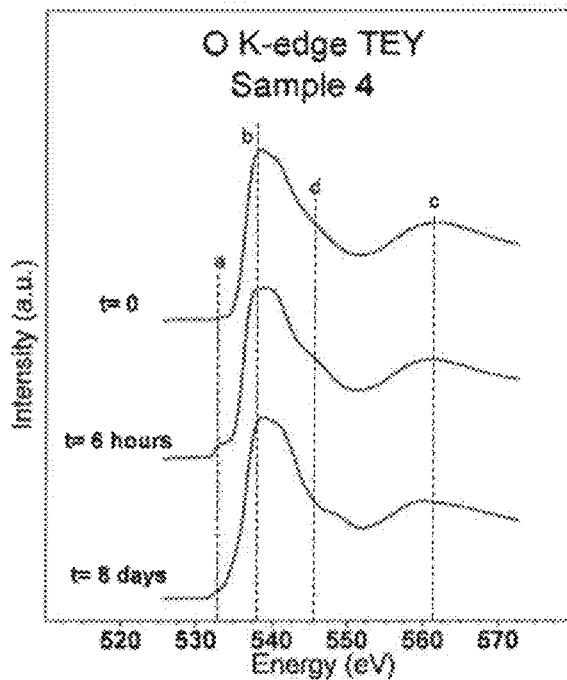
Figure 24D:
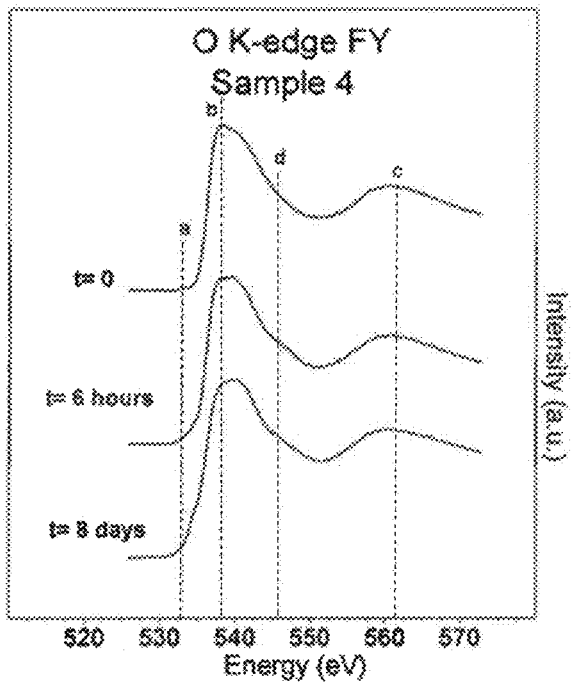
Figure 25A:
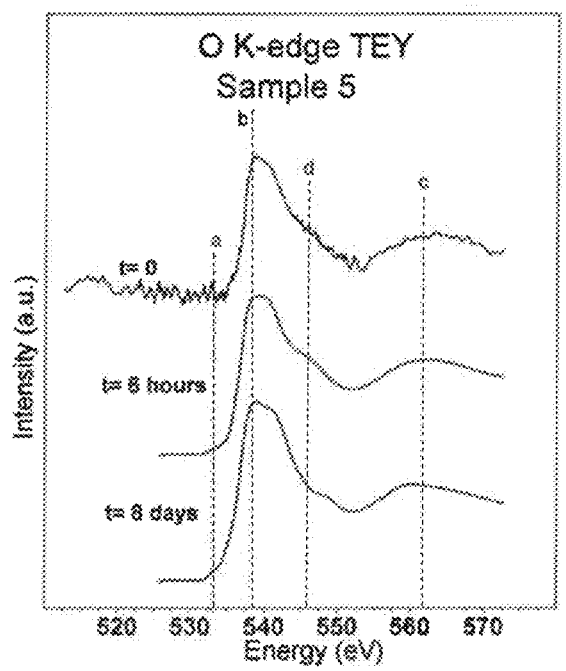
FIGS. 25A and 25B—Oxygen K-edge XANES TEY and FY spectra of Sample 5 and FIGS. 25C and 25D of Sample 6 high-nitrogen SiONPx coating chemistries weak pre-edge (a) shows evidence of Si—OH type bonding, post edge features (b), (c) show evidence of Si—O bonding while (d) shows evidence of phosphate bonding.
Figure 25B:
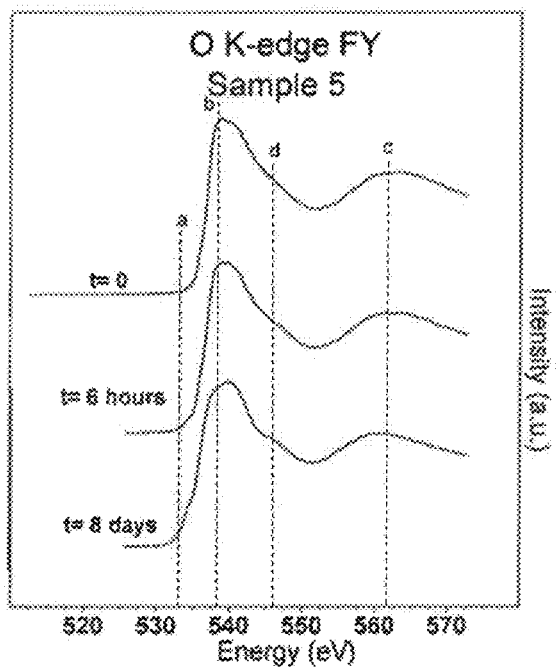
Figure 25C:
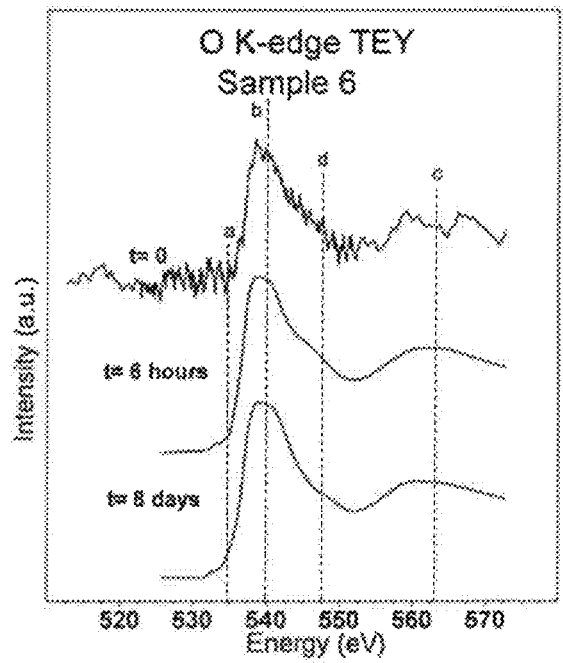
Figure 25D:
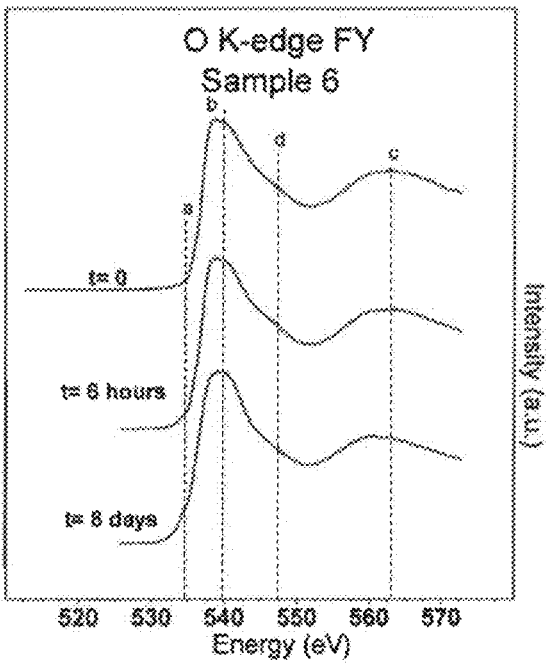

The Silica Si—K edge can also be used to investigate chemical changes and structural changes in the silica chemical environment over time.[119] Silica Si—K edge spectra were acquired from 1820-1890 eV using the SGM beam line. FIGS. 22A and 22B show the Si K-edge TEY data for six sample chemistries at time 0 and 8 days. The 6 hour data was collected for these chemistries; however, a detector malfunction made it unusable. This data can be considered to be collected from the near-surface ~70 nm.[120]

There are three main peaks of interest in these spectra: peak a, the main Si K-edge peak around 1847±0.3 eV, a post edge peak b feature common to all spectra around 1864.8±0.2 eV, and peak c around 1840.8±0.3 eV. The broad main peak a can be thought of as the sum total contribution of Si—Si bonding (~1841 eV), Si—N bonding (~1844.5 eV) and Si—O bonding (1847 eV) resonances, while a separation of this peak into multiple distinct peaks (peak a and peak c) can be seen in systems where Si—O, Si—N, and Si—Si bonding exist in distinct domains, rather than as an amorphous continuum of energies centered at 1847 eV.[124] The high-N content samples 1, 2, 3, and 4 initially show evidence of all three bonding forms with a leading edge around 1841 eV and a broad absorption peak encompassing both Si—N and Si—O resonant energies. The higher oxygen content samples 5 and 6 appear initially to consist primarily of Si—O bonds. After 8 days of dissolution, however, the local chemical environment of the Si near the sample surfaces seems to change for all sample chemistries. Sample 1 appears to contain primarily silica-like Si—O bonding, with little evidence of Si—N bonding. Samples 2 and 3 show evidence of distinct Si—Si bonding (peak c), Si—O bonding (peak a), and Si—N bonding (post-edge shoulder on peak a, not labeled). Samples 4 and 5, like sample 1, show primarily Si—O bonding, however, a spectral contribution from Si—Si bonding is also observed. Sample 6, the highest oxygen content sample initially, shows strong contributions from both Si—Si and Si—O bonding. In all cases the peak a intensity shifts towards the Si—O bonding resonance energy. This may be due to the exposure of silica sub layer or it may be due to the presence of Si—O bonding in the microstructures formed on the sample surfaces.

Oxygen K-Edge

Figure 26:
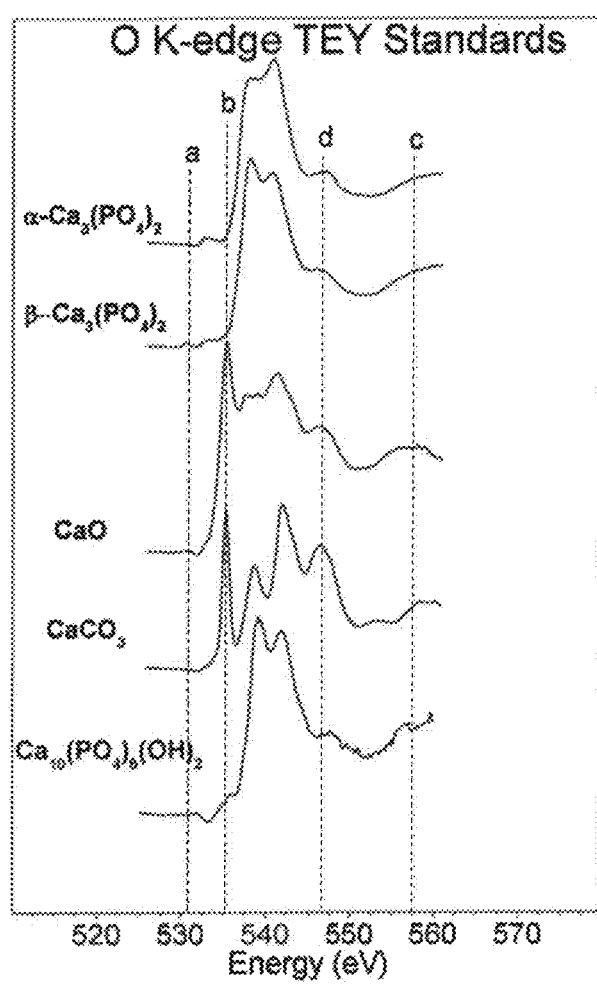
FIG. 26—Oxygen K-edge XANES TEY spectra of calcium phosphate standards.
Figure 27A:
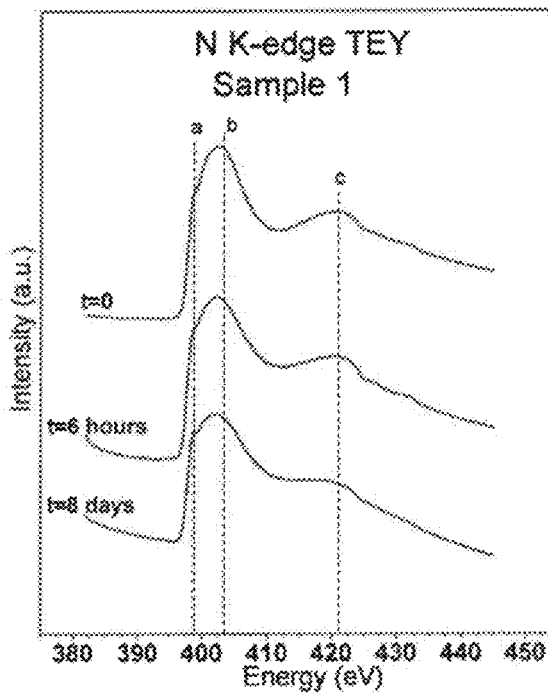
FIGS. 27A and 27B—Nitrogen K-edge XANES TEY and FY spectra of Sample 1 and FIGS. 27C and 27D of Sample 2 low-oxygen SiONPx coating chemistries (a) showing the presence of 2-fold coordinated nitrogen.
Figure 27B:
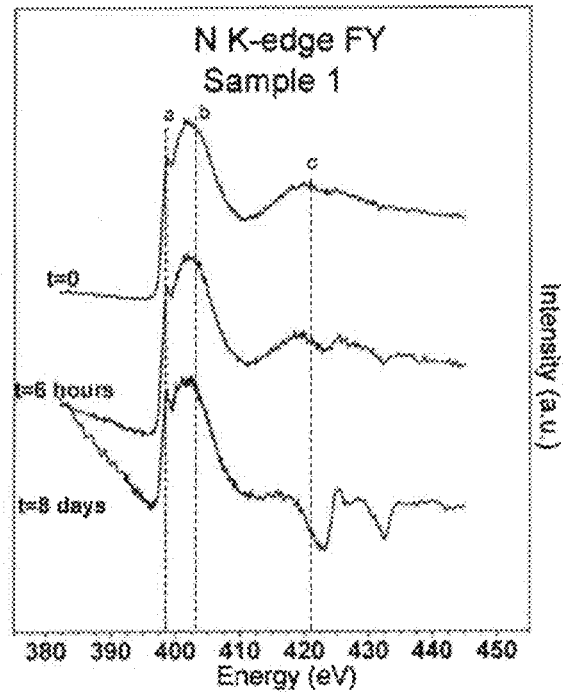
Figure 27C:
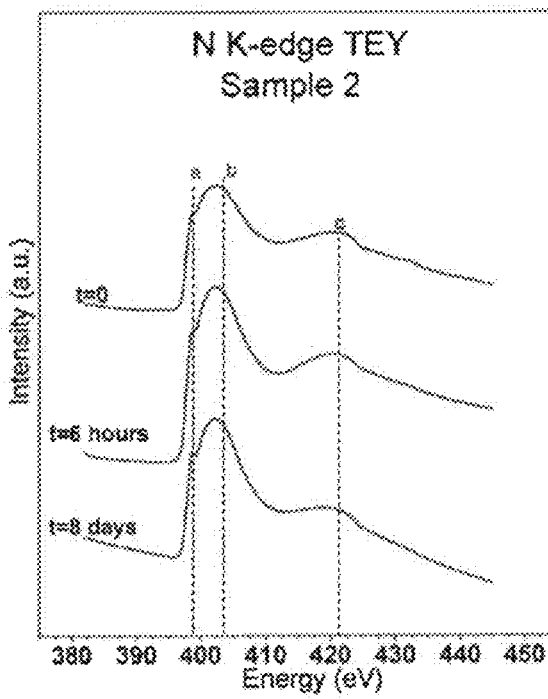
Figure 27D:
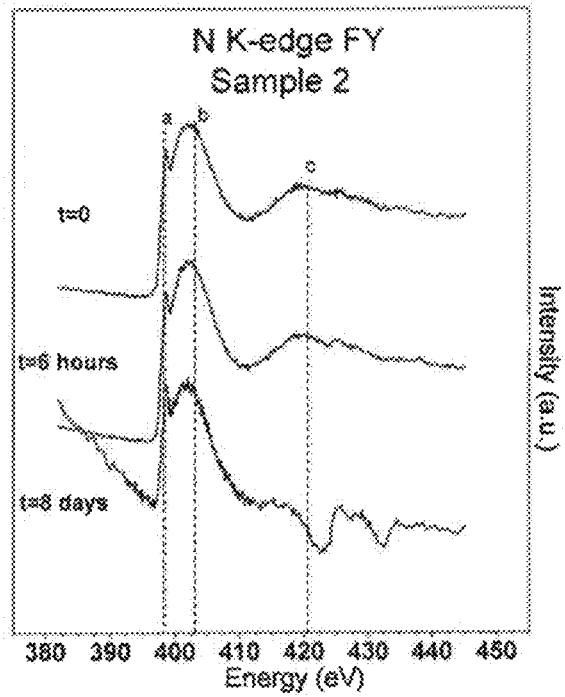
Figure 29A:
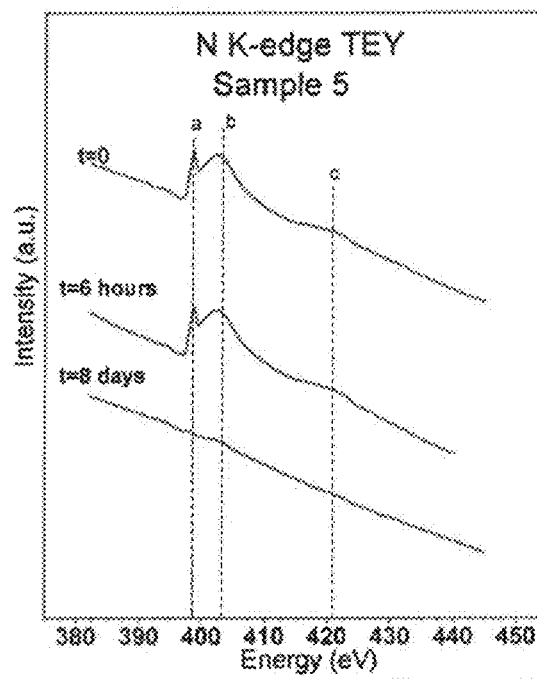
FIGS. 29A and 29B—Nitrogen K-edge XANES TEY and FY spectra of Sample 5 and FIGS. 29C and 29D of Sample 6 high-nitrogen SiONPx coating chemistries showing (a) the presence of 2-fold coordinated nitrogen.
Figure 29B:
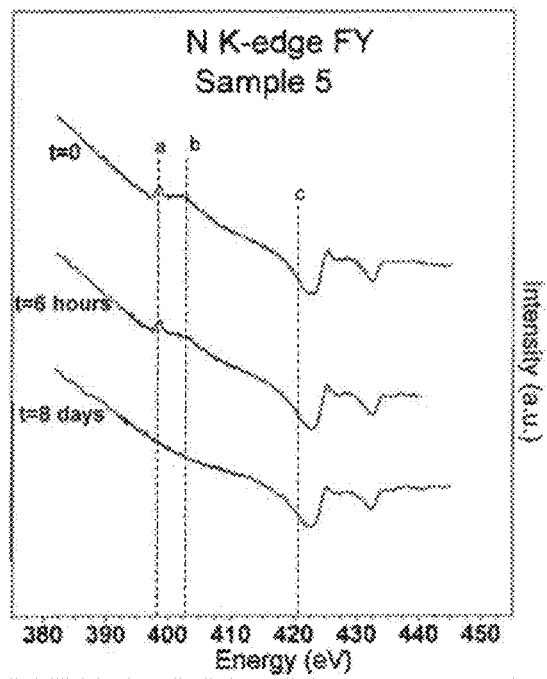
Figure 29C:
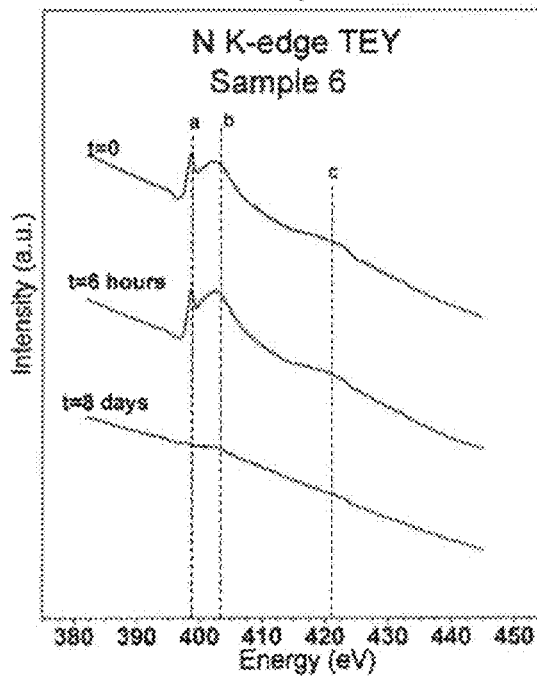
Figure 29D:
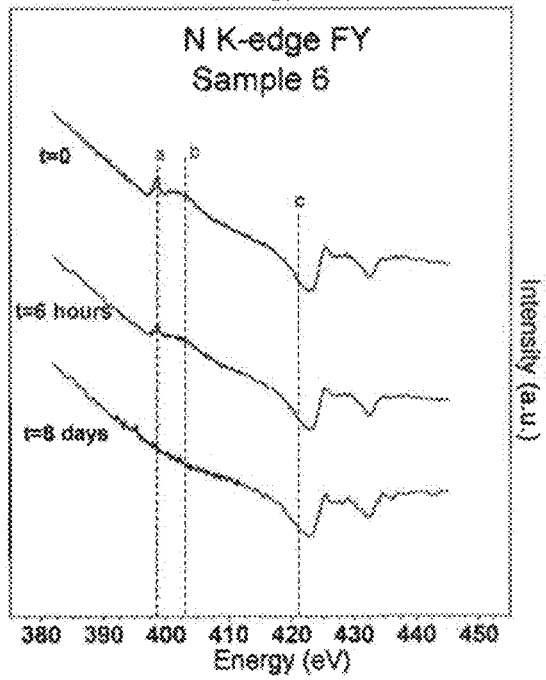
Figure 30A:
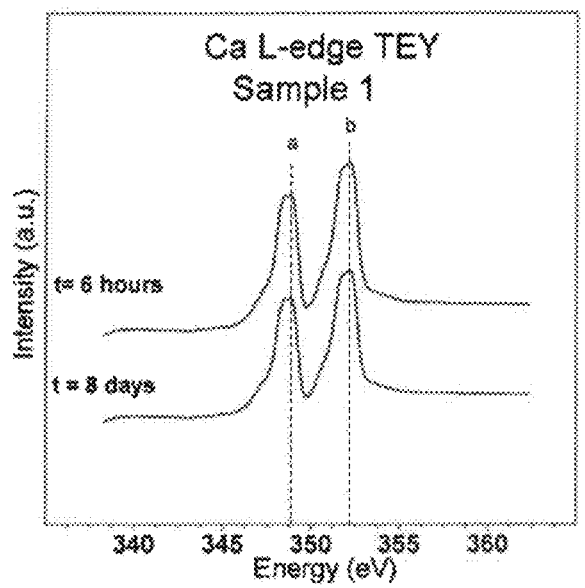
FIGS. 30A and 30B—Ca $L_{2,3}$-edge XANES TEY and FY spectra of Sample 1 and FIGS. 30C and 30D of Sample 2 low-oxygen SiONPx coating chemistries peaks (a) and (b) are the Ca L2 and L3 edges, respectively and indicate the presence of calcium on the surface.
Figure 30B:
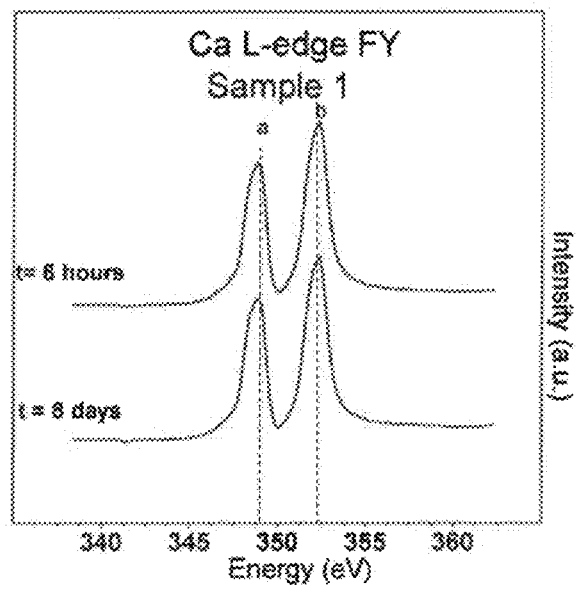
Figure 30C:
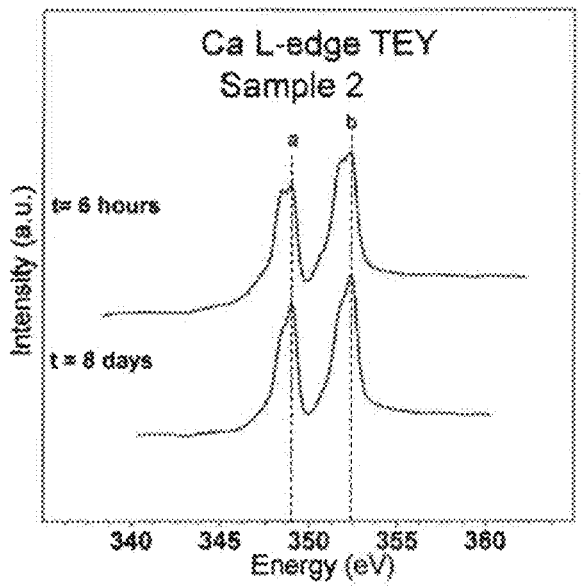
Figure 30D:
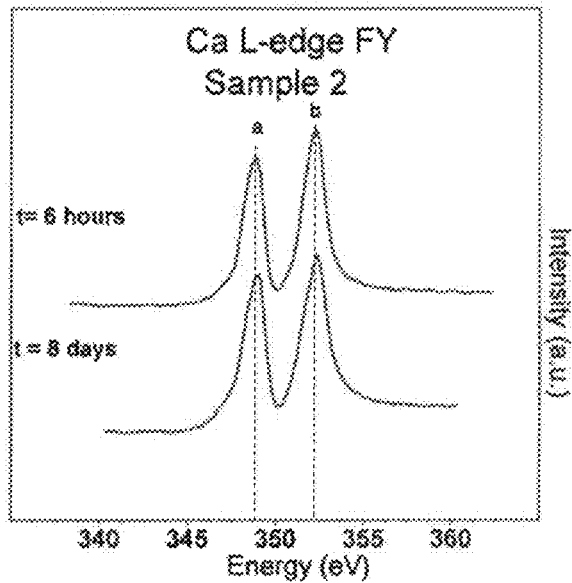
Figure 31A:
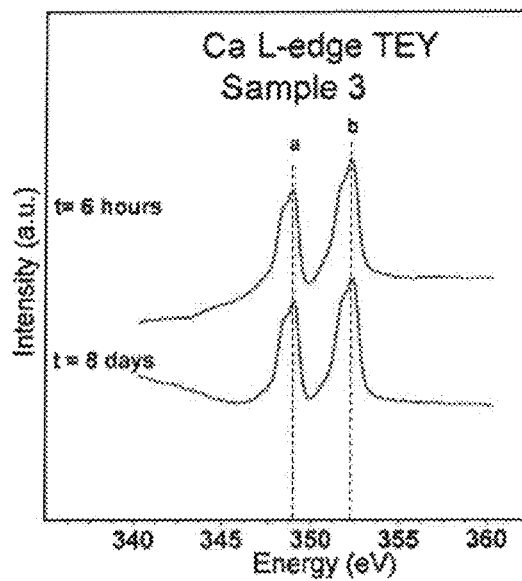
FIGS. 31A and 31B—Ca $L_{2,3}$-edge XANES TEY and FY spectra of Sample 3 and FIGS. 31C and 31D of Sample 4 intermediate nitrogen and oxygen SiONPx coating chemistries peaks (a) and (b) are the Ca L2 and L3 edges, respectively and indicate the presence of calcium on the surface.
Figure 31B:
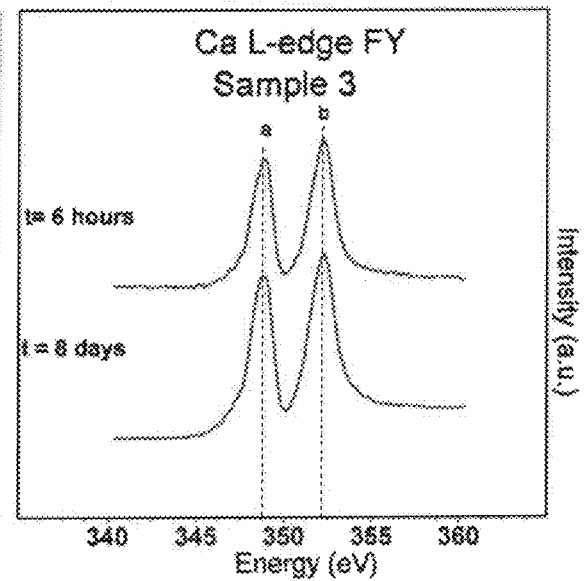
Figure 31C:
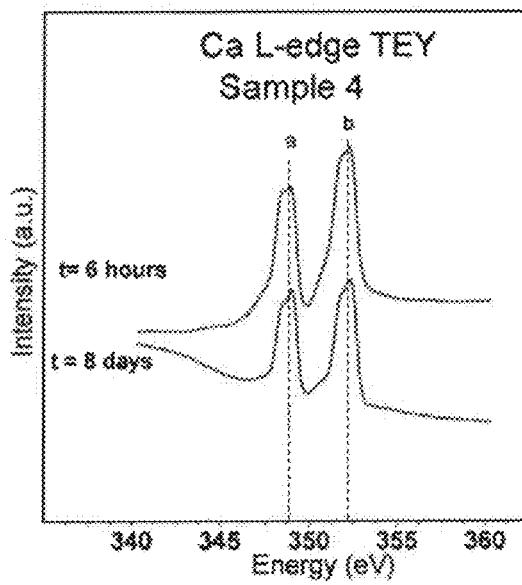
Figure 31D:
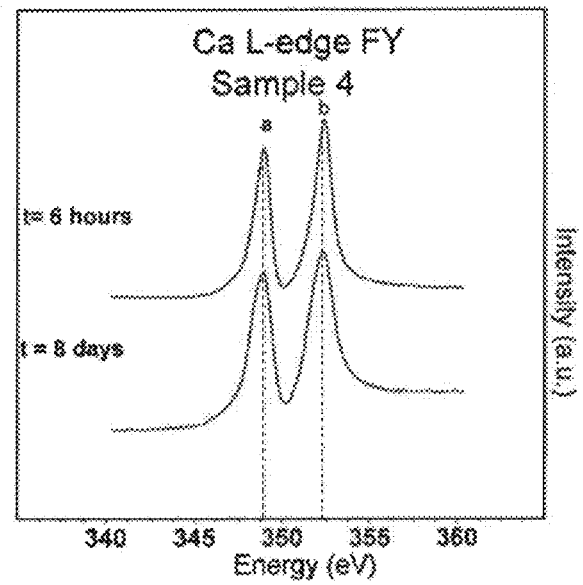
Figure 32A:
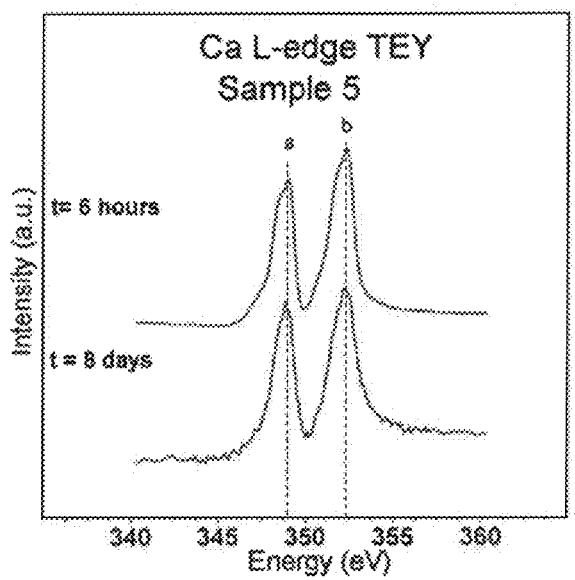
FIGS. 32A and 32B—Ca $L_{2,3}$-edge XANES TEY and FY spectra of Sample 5 and FIGS. 32C and 32D of Sample 6 high-nitrogen SiONPx coating chemistries peaks (a) and (b) are the Ca L2 and L3 edges, respectively and indicate the presence of calcium on the surface.
Figure 32B:
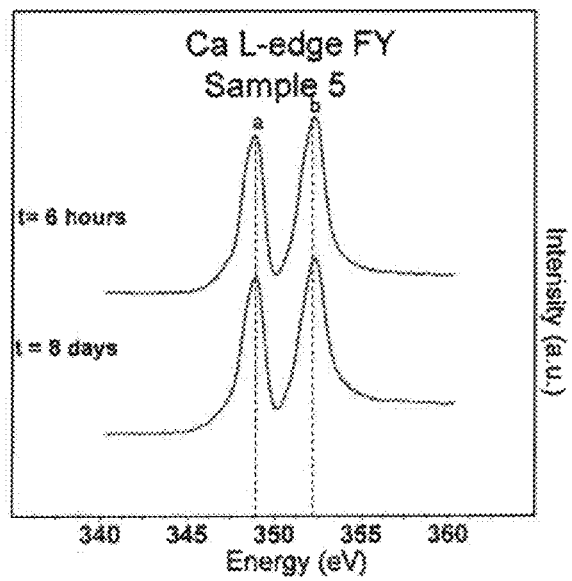
Figure 32C:
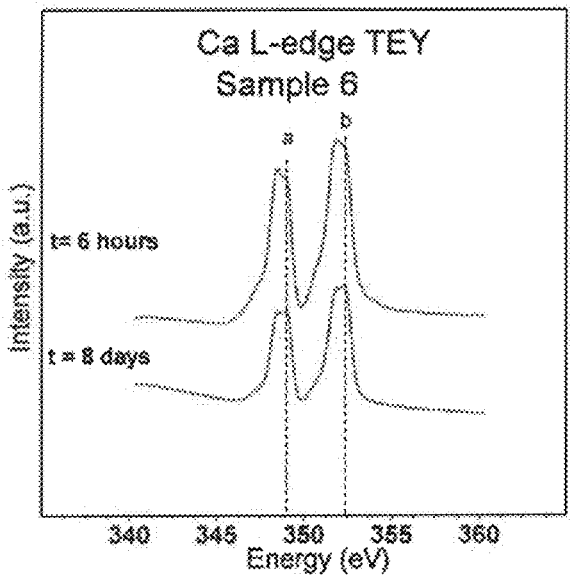
Figure 32D:
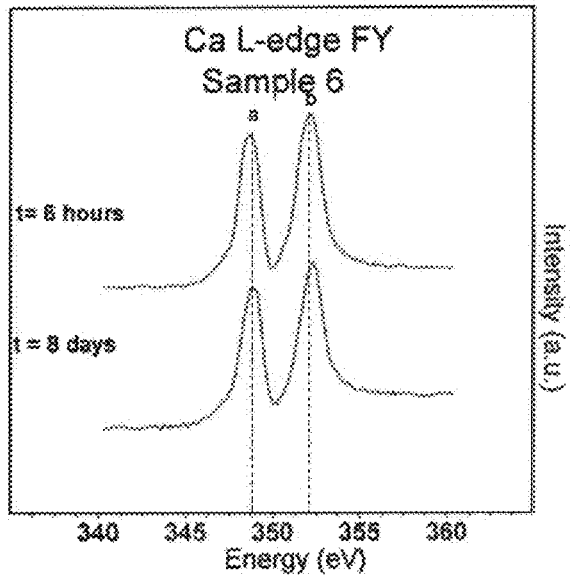

The Oxygen K-edge can be used to investigate changes in local oxygen structure over time. All O—K edge spectra were acquired from 525-585 eV using the SGM beam line. FIGS. 23A-23D, FIGS. 24A-24D and FIGS. 25A-25D show the O K-edge TEY and FY data for the six SiONPx sample chemistries at time 0, 6 hours, and 8 days. Since one of the goals of these coatings is the formation of a calcium phosphate or apatite-like structure on the surface as a measure of bioactivity, FIG. 26 shows O—K edge TEY and FY data of some calcium standards for comparison including alpha-tricalcium phosphate, beta-tricalcium phosphate, calcium oxide, calcium carbonate and hydroxyapatite. The TEY data for this edge can be considered to be collected from the near-surface (~25 nm) while the FY data contains information from a deeper interaction area of about ~150 nm. There are four main peaks observed in these spectra: peak a, a pre-edge peak around 529.9±0.2 eV, the main O—K edge peak b around 535.2±10.2 eV, a post edge peak c feature around 558.5±0.2 eV, and a post-edge peak d shoulder around 546.4±0.2 eV. Peak a, which is observed as a distinct peak in the low-oxygen content sample 1, 2, and 3 chemistries in the TEY data at time 0 may suggest the presence of silanol (Si—OH) bonding at the near surface while the absence of this peak in the FY data suggests that the primary oxygen bonding in the bulk of the coatings for all samples at time 0 can be attributed to Si—O—Si bridges, as evidenced by the main peak b and post-edge resonance peak c.[125]

For the high oxygen content samples 3, 4, 5, and 6, little change is observed from the initial t=0 spectra to the t=8 days spectra. This lack of spectra evolution may be due to the abundance of oxygen in these samples, which overwhelms the spectral contribution from any new oxygen species that form on the surface. The low-oxygen content samples, by contrast, show evidence of both a pre-edge at a higher energy than peak "a" and a post edge shoulder, peak "d", in their fluorescence yield data after 8 days of immersion. These pre- and post-edge features may indicate the presence of oxygen that is not bound to silica. A quick review of the standards in FIG. 26 reveals that these spectral features may be due to a combination of phosphate and carbonate species, which might suggest the formation of a carbonated apatite-like structure on these surfaces.

Nitrogen K-Edge

The Nitrogen K-edge can be used to investigate local nitrogen structure over time. All N—K edge spectra were acquired from 380-450 eV using the SGM beam line. FIGS. 27A-27D, FIGS. 28A-28D and FIGS. 29A-29D show the N K-edge TEY and FY data for the six SiONPx sample chemistries. The TEY data can be considered to be collected from the near-surface (~20 nm) while the FY data contains information from a deeper interaction area of about ~125 nm. There are three main peaks observed in these spectra: peak a, around 398.6±0.2 eV, the main peak b around 402.6±0.2 eV, and a post edge peak c feature around 421.4±0.2 eV.

Peak a has been attributed to the presence of under coordinated (i.e. two-fold coordinated) or hydrogen-bound nitrogen which indicates either the presence of N—H bonding or the substitution of a nitrogen atom for an oxygen atom into a Si—O—Si bridge.[125, 126] This resonance peak is observed in all spectra at time zero. All high nitrogen chemistries show little change in spectral features in even after 8 days of immersion. This suggests that most of the Si—N bonds in these coatings are relatively unreactive with the salts in the αMEM solution. The absence of nitrogen in samples 5 and 6 after 8 days immersion is likely due to a combination of two factors: the relative scarcity of nitrogen in these systems as well as interference from the microstructural layer that forms which may mask any nitrogen still left in the coating. The peaks observed between 425 eV-435 eV in these spectra may be due to a higher order spectral contribution from silica, which overwhelms the nitrogen signal in these relatively Si-rich and N-poor coatings.

Calcium $L_{2,3}$-Edge

The calcium $L_{2,3}$-edge can be used to investigate the local structure of any calcium deposits on the surface. Calcium, though not originally present in the coatings, may precipitate from the αMEM saturated solution, particularly in the form of calcium phosphates. Though the O—K edge data showed little evidence of calcium phosphates, carbonates or oxides on the surface for most sample chemistries, it is possible that the oxygen signal from these bonds was overwhelmed by Si—O-type bonding. Ca $L_{2,3}$-edge data should not suffer from this complication.

All Ca $L_{2,3}$-edge spectra were acquired from 340-360 eV using the SGM beam line. FIGS. 30A-30D, FIGS. 31A-31D and FIGS. 32A-32D show the Ca $L_{2,3}$-edge TEY and FY data for the six SiONPx sample chemistries at time 6 hours and 8 days. FIG. 33 shows Ca $L_{2,3}$-edge TEY data of some calcium standards for comparison including alpha-tricalcium phosphate, beta-tricalcium phosphate, calcium oxide, calcium carbonate and hydroxyapatite. The TEY data can be considered to be collected from the near-surface (~15 nm) while the FY data contains information from a deeper interaction area of about ~110 nm.

There are two main peaks observed in these spectra: peak a, around 351.0±0.2 eV and peak b around 353.2±0.2 eV. As with the P and Si $L_{2,3}$-edges, these peaks arise from the transition of 2p electrons to unoccupied 3d orbitals that have been split by spin-orbital splitting and do not observe shifts in energy due to the chemical bonding environment of a silica atom. As such, these peaks are not particularly useful to identify a specific calcium chemistry. They are quite strong, however, and allow for the detection of trace amounts of calcium in a sample that might otherwise be undetectable. For all sample chemistries, calcium is detected after 6 hours in both the fluorescence yield and the total electron yield data. In the TEY spectra after 6 hours, pre-edge peaks start to become distinct, which may indicate the presence of calcium in the form of calcium phosphate, though a comparison with the standards shows that the pre-edge features of various calcium phosphates overlap, making it difficult to differentiate between specific mineral structures.

Phosphorous $L_{2,3}$-Edge

The phosphorous $L_{2,3}$-edge can be used to investigate the local structure of phosphorous deposits on the surface. Phosphorous, though not originally present in the coatings, may precipitate from the αMEM saturated solution, particularly in the form of phosphate. Though the O—K edge data showed little evidence of calcium phosphates on most of the sample surfaces, it is possible that the oxygen signal from these bonds was overwhelmed by Si—O-type bonding. The P $L_{2,3}$-edge data should provide better insight into any phosphate precipitation on the surface. All P $L_{2,3}$-edge spectra were acquired from 130-155 eV using the PGM-VLS beam line. FIGS. 34A-34B, FIGS. 35A-35B and FIGS. 36A-36B show the P $L_{2,3}$-edge FY data for the six SiONPx sample chemistries at time 0, 6, 12, and 18 hours. FIG. 37 shows P $L_{2,3}$-edge FY data of some calcium phosphate standards for comparison including alpha-tricalcium phosphate, beta-tricalcium phosphate, dicalcium phosphate, anhydrous dicalcium phosphate, and hydroxyapatite. The FY data contains information from an interaction depth of about ~75 nm. There are five main peaks observed in these spectra: peak a, around 135.7±0.2 eV, peak b around 137.4±0.2 eV, peak c around 138.8±0.2 eV, a post edge peak d feature around 147.0±0.2 eV, and a pre-edge peak e feature around 136.1±0.2 eV.

The transitions in L edge spectra follow distinct patterns, and the P $L_{2,3}$-edge peaks a and b are proposed to arise from the transition from 2p electrons (spin-orbit split into $2p_{3/2}$ and $2p_{1/2}$ levels) to the lowest unoccupied 3s-like antibonding state.[135] Peak c has been attributed to a transition to a 3p-like antibonding state in the presence of oxygen, and peak d is considered to arise from 2p to 3d transitions.[136] Since some of these peaks arise from transitions observed only in P—O bonding (peak c and peak d), while others are generally observed in the absence of P—O bonding (peak a and peak b), the P L-edge is useful in determining the loss or reaction of phosphorous from the coating surface.

Peak a, around 135.7±0.2 eV, and peak b around 137.4±0.2 eV are only observed in the t=0 spectra of samples 2, 3, 4, 5, and 6 as a broad peak centered near 136.0 eV. These peaks are quickly lost, however, after the samples have been exposed to the αMEM solution. After 6 hours, all spectra show evidence of calcium phosphate formation. The presence of the pre-edge peak e as well as the peak c and peak d spectral contributions are common to several forms of calcium phosphate. The strong post-c-peak shoulder, however, indicates that the majority of the phosphorous present is in the form of either beta-tricalcium phosphate or hydroxyapatite.

XANES Si L-edge, Si K-edge, O K-edge, N K-edge, Ca L-edge, and P L-edge spectra were acquired for αMEM immersion of six SiONPx coating chemistries: two high-nitrogen content samples, two intermediate nitrogen/oxygen content samples, and two high-oxygen content samples at three time points: t=0, 6 hours, and 8 days. Changes in the spectral features of these coatings as a function of time immersed in αMEM solution were noted. The evolution of the Si L-edge spectra suggests that after 8 hours, the majority of the silica in the samples at the near surface is the form of silica, specifically in a looser, gel-like network. The Si—K edge spectra suggest the presence of Si—Si bonding after 8 days immersion for some of the high nitrogen content samples which is likely due to the underlying Si wafer crystalline Si—Si bonding, indicating that the coatings have almost entirely or entirely dissolved. The development of pre-edge and post-edge shoulder peaks in the O K-edge spectra suggests the incorporation of carbonate or phosphate species into the surfaces after 6 hours and 8 days. The Ca L-edge spectra suggest that calcium forms on the surface after 6 hours in solution and the calcium precipitate structure becomes better ordered over the course of 8 days immersion in solution. The P L-edge spectra show the migration of phosphate to the sample surfaces over the course of 18 hours into the form of a calcium phosphate species. A comparison with the P L-edge of various calcium phosphate standards suggests that the dominant phosphorous compound on the surface is either beta-tricalcium phosphate or hydroxyapatite. The formation of this calcium phosphate mineral on the surface suggests that these coating chemistries would be bioactive in vivo, though further study is needed to determine whether this would result in a strong bone-coating interface.

Example 10—In Vivo Orthopedic Implant of Si—O—N—P Coated Product into Tibia Bone Diaphyseal tibial fractures are one of the most common fractures related with high energy trauma, it is referred 492,000 tibial fractures in US per year. This fracture usually is related with, loss of bone fragments, relevant soft tissue injury and vascular damage whom eventually leads to a deficient consolidation (delayed unions or non-unions). The field of biomechanics and hardware usage to treat these fractures has evolved considerably. However, this progress has not been followed by biological research, such as uses of biomaterials and growth factors that could be used to enhance the healing process and prevent complications. Nowadays, intramedullary rods are the gold standard on treatment of most tibial shaft fractures. Bioengineering research have been trying to prevent or minimize the problems with this fractures consolidation adding some materials such as Hydroxyapatite (HA) and PLLA for coating or as a back bone, respectively, of some of these rods/nails. Nevertheless, nothing has been used yet on routine clinical practice.

Rats have been used on tibial fracture animal model due to their size, favorable immunologic condition and price. The guillotine method seems to be the most common for creating fractures. Therefore, we use a guillotine modified method to provoke a high energy tibial fracture in Sprague Dawley adult rats. While other investigators have used the femur, the tibia is used in the present studies because the tibia is considered to have more scientific meaning due to its superficial location, the procedure is easier to control, and this bone is the primary site of complications related to bone.

The effect of PECVD SiONP coated orthopaedic rods on enhancement of bone healing process of this specific fracture was evaluated. Inducing new vascularization and accordingly new bone formation will enhance the healing process.

Three animals were used to evaluate and identify the main vascular nutrition of knee and tibia of these animals. This creates a feasible way to mimic a real situation by blocking the specific artery related with created fracture site. Other studies have used ischemic models, for example chemical induced, or even made ligature of main arteries such as femoral. However, none of those represent a real situation. In this study, a ligature of a vessel closer to the fracture site was made, which better represents a real situation of high energy tibial fracture with vascular deprivation.

Protocol: The protocol for fracture animal model with fracture stabilization and drug delivery treatment comprises the following steps:

1. The entire procedure was performed using aseptic technique.
2. The animal was deeply anesthetized by inhalation of isoflurane 4-5% for induction and 1-2% for maintenance.
3. Trichotomy of hind limbs area and cleaning with iodine with wipes of 70% alcohol based solution was done.
4. Animal hind limb was placed in a triangular support that kept the leg flexed to 90 degrees (see FIG. 38A).
5. An incision was made in the trans patellar tendon.
6. A initial whole was made using a 1.5 mm drill bit immediately anterior to the tibial plateau.
7. A 1 mm Kisrchner wire (rod) either coated with biosilica or naked, depend on the studied group, was place intramedullary up to distal third of tibia diaphysis (see FIG. 38B).
8. The surgical knee wound was closed with suture, nylon 6.0 and externally taped.
9. The animal was placed on fracture apparatus and the fracture was created (See FIG. 39 and FIG. 40).
10. While the animal recovered, the analgesics were maintained for 48 h.

This study will be completed with the implantation of the treated devices into a rat model. It is expected that PECVD SiONP rods will result in the enhancement of the bone healing process of this specific tibial fracture and that therefore, enhanced healing and vascularization would be expected with other types of fractures, for example, calvarial fractures. It is also expected that new vascularization will be induced at these plasma coated biosilica rods and that new bone formation will enhance the healing process.

Example 11—Three-Dimensional Surface Coating Deposition

Also envisioned, as another aspect of the invention, is depositing the SiONPx coating as described herein as a three-dimensional substrate. Structurally unstable fracture sites require permanent or semi-permanent bone implants that are typically made of titanium (Ti) or other inert metals. The material properties of these fixative devices play significant role in bone healing. A material that that reacts favorably and adheres well to the in-vivo bone environment is critical for rapid bone healing. Here, we demonstrate the use of nanofabricated amorphous silica oxynitrophosphide (Si—O—N—P or SiONPx) as an overlay onto metal implants in load-bearing bone defect applications. The mechanical and chemical characterization of nanofabricated device to assess its adhesion to the underlying metal/metal oxide is also shown here. Osteoinductive behavior was observed when placed in a biological environment in-vitro and craniofacial defects in-vivo. The interaction of the elemental components at bone-SiONP/TiO2/Ti interface is discussed here.

Advantages of using the PEVD deposition techniques of the present invention is that all surface, such as a concave surfaces, socket, indented, curved, or other modified, not planar surfaces, would completely be coated with the present techniques. This provides for the fabrication of a device or other implement that has greater suitability for enhancing the assimilation of cellular assimilation and growth, such as the growth of bone osteoblast cells and vascularization types of cells, onto all sides and crevices of a device. This, in turn, facilitates a faster and more complete healing at a wound site.

Example 12—Rapid Bone Healing Using Nanofabricated Implant Surfaces with Si—O—N—P Overlays Developing a material that stimulates osteogenesis and adheres well to the in-vivo bone environment is critical for rapid bone healing. Bioactive glass coatings onto metal implants provide the missing osteoinductive properties but lack interfacial adhesion and face delamination. The present PECVD-based nanofabricated amorphous silica oxynitrophosphide (Si—O—N—P) overlays onto metal surfaces enhance osteogenesis and accelerate bone healing via rapid biomineralization.

The nanofabricated implant surfaces were patterned using photolithography and etching followed by PECVD deposition of Si—O—N—P overlays. Surface morphology and thin film characterization was conducted using ellipsometer, reflectometer, scanning electron microscope (SEM) and X-ray Absorbance Near Edge Structure (XANES) Spectroscopy. Cells' response to various surface chemistries was evaluated using MC3T3 cells and relative gene expression of several osteogenic markers (SOD1, Sp7, Smad1, Smad5, Runx2, OCN and Col1a1) were recorded using qPCR. Raman spectroscopy and optical microscopy were used to study the biomineralization. Critical sized calvarial defect model in rats was used to test the samples for in-vivo studies.

PECVD process gave highly controlled, reproducible and conformal films of Si—O—N—P overlay. The P to N ratio varies the dissolution rate, chemical structure and bioactivity of the surface. XANES data revealed early formation of HA on Si—O—N—P test samples within 6 hours of in-vitro immersion. Cell culture studies showed that surface structure and material chemistry of Si—O—N—P surfaces induced a favorable cells' response and enhanced osteogenic markers, which was evident by many-fold increased gene expressions leading to rapid biomineralization of Si—O—N—P surfaces. In-vivo testing showed that Si—O—N—P test samples with optimized surface morphology were integrated well to the surround bone while micro CT data revealed adequate filling of the bone-implant gaps with mineralized bone within 5 weeks.

Conclusion: Si—O—N—P surfaces induced a favorable cells' response and enhanced osteogenic markers, which was evident by many-fold increased gene expressions of SOD1 (FIG. 42A), Sp7 (FIG. 42B), Smad1 (FIG. 42C), Smad5 (FIG. 42D), Runx2 (FIG. 42E), OCN (FIG. 42F) and Col1a1 (FIG. 42G). The results shown at FIGS. 43A, 43B and 43C demonstrate that SiONP coated surfaces facilitated osteoinductive behavior by cells when placed in a biological environment in-vitro and craniofacial defects in-vivo. The interaction of the elemental components at bone-SiONP/$TiO_2$/Ti interface promoted cellular activity to enhance/achieve defect healing. (See FIG. 43A), while non-coated surfaces did not (FIG. 43B).

Silica oxynitrophosphide thin films integrate well with surrounding bone in critical-sized calvarial defects. While not intending to be limited to any particular or specific mechanism of action, it is proposed that HA is rapidly formed at the treated surface, while releasing ionic Si to enhance osteogenic differentiation during osteogenesis. The coatings are also expected to enhance vasculogenesis and angiogenesis by endothelial cells to enhance the formation of blood vessels in the newly formed bone.

Example 13—Osteoinductive Properties of SiONP Implants Stimulate Bone Healing Via Rapid Mineral Formation Structurally unstable fracture sites require permanent or semi-permanent bone implants that are typically made of titanium (Ti) or other inert metals. The material properties of these fixative devices play significant role in bone healing. A material that reacts favorably and adheres well to the in-vivo bone environment is critical for rapid bone healing. Here, the use of nanofabricated amorphous silica oxynitrophosphide (Si—O—N—P) as an overlay onto metal implants in load-bearing bone defect applications is demonstrated. The mechanical and chemical characterization of a nanofabricated device to assess its adhesion to the underlying metal/metal oxide is also demonstrated. The osteoinductive behavior of these surfaces when placed in biological environment in-vitro and craniofacial defects in-vivo is then demonstrated. The interaction of the elemental components at bone-SiONP/TiO2/Ti interface will be also presented.

Example 14—Key Differences Between the SiON and SiONP Chemistries, Methods and Structures/Films Created While not intending to be limited to any specific mode of action or theory, the SiON is primarily intended to be used for craniofacial applications, such as implants. The SiONP is primarily intended for both craniofacial and orthopedic applications, such as in medical implant materials.

SiON is a completely soluble material, while SiONP is a more slow dissolving material.

The SiON favors carbonated hydroxyapatite. In contrast, the SiONP forms standard hydroxyapatite.

The different characteristics of these materials will render one more suitable for use in a particular biological/defect correcting application.

Example 15—Stacked and Patterned Treated Surface Constructs

The present example provides a description of the utility of the present invention for providing a surface that may be fabricated to include multiple (more than two) treated surfaces, wherein at least one of the surfaces is treated to include a thin film of a P-containing composition, such as a layer of SiONPx.

Another construct could have a biomedical device material surface that has lithographically etched patterns with SiONPx or SiONx or SiOx coatings fabricated into a variety of "stacked" layers, where for example, one chemistry underlies another chemistry inside the etched features. The creation of such a construct would use a method of "etch-back" or "lift-off" method. These methods are used in semiconductor applications.

Example 16—Dissolution of SiONPx Coating on a Treated Surface

SiONPx coatings show a greater promise for potential application to bone. This is in part attributable to the dissolution rates of such coating as compared to SiONx coatings. The dissolution between these two types of coatings has been compared to that of bioglass in a five step mechanism as seen in FIGS. 46A and 46B (Stage 1-Stage 5).

For the nitrogen incorporated silica-like RBM SiONPx, much of the nitrogen in the coatings is under-coordinated (NK-edge) and it quickly associates with H+. The phosphate-like phosphorous is also presumed to quickly dissolve from the coating and a small plateau is seen in the ICP P data recording the loss of phosphorous in solution which is believed to arise from this initial P release. (Stage II) This process also consumes a limited amount of H+, and the local surface pH reaches a point where the Si—O—Si bonds rupture. ICP data shows that Stage III, where the silanol gel layer forms and silica starts being released from the coating, happens very rapidly—within 4 hours 30-40% of the Si in these coatings has been released. (Stage IV) The relatively open structure of the silica gel layer allows for migration of ions in solution, and ICP data shows a loss of Ca and P from solution within 4 hours while XANES Ca L-edge and P L-edge data shows the formation of a calcium phosphate on the surface by 6 hours. (Stage V) The Ca—PO4 mineral formed then becomes less soluble and more like a carbonated hydroxyapatite structure over the course of 18 hours, as seen in the P L-edge data. This process is assumed to reach a steady state since the amount of Ca and P lost from solution, as seen in the ICP curves.

The Ca—PO4 mineral formed then becomes more and more like a carbonated hydroxyapatite structure over the course of 18 hours, as seen in the P L-edge data. This process is assumed to reach a steady state since the amount of Ca and P lost from solution, as seen in the ICP curves, arrests after 24 hours. These coatings are therefore considered bioactive, since they form a carbonated apatite layer in vitro, and they show promise as potential coatings for load-bearing Ti-implant coatings in vivo. The treatment of these PECVD coating from the point of view of their bonding structure—RMM versus RBM—is a small departure from current literature. The atomic bonding structure of commercial Bioglass 45S5 has been investigated previously for solgel and melt-quench fabrication techniques. In terms of the RBM or RMM view of bonding, the structure of this commercial bioactive glass would be better modeled as a RBM network of silica tetrahedrons with Ca, Na, and P network modifiers. Though this is a somewhat simplified view of a relatively complex structure that is known to have local concentrations of network modifiers like Ca as well as is believed to include domains of orthophosphate that are somewhat isolated from the silica network. [151,155] Interestingly, in this type of glass structure P—O bonding is not observed until >50 mol % phosphate is used to fabricate glass. This suggests that the present work—particularly the SiONPx wafers, represents a departure from previous efforts in terms of structure, particularly with respect to phosphate coordination in RBM structure glasses as well as the more distinct domains in the RMM structure glasses. These distinct structures, which are hypothesized to undergo slightly different dissolution mechanisms, may implications for bioactivity in vivo, particularly with respect to tailoring Si release and surface nano-scale morphology during dissolution as whole domains may be lost in the RMM glass structures during dissolution while the RBM dissolution is hypothesized to be more uniform.

Prophetic Example 17—Craniofacial Repair and Applications

The present example provides a description of the use of the Si—O—N—P technologies in the repair of craniofacial defects.

The repair of craniofacial defects presents unique challenges, and has met with limited success with techniques currently available, primarily due to limitations associated with the use of Ti implants.

Current Ti implants used for healing bone do not promote covalent bonding to the surrounding bone upon or after implantation. They typically have longer than desired healing times (>9-12 months) and poor adhesion to bone when subjected to micro-mechanical movement.

Coatings such as hydroxyapatite or bioactive glasses do not form an ionic bond to the surface of Ti or other metal implants. HA and BG coatings also are fabricated at high temperature (>700 C), which can cause the BG to undergo glass transition and its bioactivity to be reduced. For HA and BG, after fabrication at high temperature, the coating and implant are quenched rapidly to preserve the fabricated structure. As the coating cools, it can suffer from delamination at the metal-glass or metal-HA interface due to thermal expansion mismatch. Another issue that occurs during cooling for HA is the issue regarding incongruent cooling and separation of multiple phases of calcium phosphate. These issues ultimately compromise the coating adhesion to the implant surface or lifetime of the coating material to maintain its structure.

The PECVD methodology overcomes these limitations by fabricating amorphous films at relatively low temperatures (<500 C), which greatly reduces thermal expansion mismatch issues. Further, these materials have simplified or complex chemistries and control over the fabrication thickness or localization of atimic insertion into the base amorphous silica matrix is well-controlled through the control over the chemical potential for each atom's insertion into the material structure. Control is provided via radio frequency power, temperature, pressure, gas flowrate, and gas phase reagent stoichiometry. The gas phase is considered ideal since the P is sufficiently low that inter-molecular predicted via root mean square of the gas phase molecular velocity and each gas phase molecule's partial pressure (Dalton's Law).

Example 18—Nanofabricated and Bioactive Amorphus Silica Oxynitrophosphide

In FIGS. 47A-47D, 48A-48D and 49A-49B; data is presented that demonstrates SiONP surfaces provide sustained ionic silica and P release in physiological conditions. It was previously unrecognized that a surface prepared according to the present chemistries would provide release of ionic silica and P in a physiological environment. It had not previously been observed or reported that ionic Si or P would be released from a surface.

In the present studies, release of ionic Si and P from a treated surface enhances antioxidant activity and elevated levels of phosphate upregulate several genes during osteoblast differentiation and cause rapid mineral deposition, resulting in rapid bone and capillary tube formation. Thus, SiONP-modified devices will promote antioxidant expression, reduce ROS, induce mineral deposition and stimulate bone and vascular tissue formation.

PECVD-based amorphous silica oxynitrophosphide (SiONP) films were overlaid onto patterned surfaces and test samples were studied for their osteogenic and angiogenic behaviors. Film degradation rate, in vitro gene expression and in vivo bone regeneration capabilities for varying N to P ratio were studied for various film chemistries.

The first part of this study aimed to fabricate SiONP coated test samples using PECVD process. PECVD-based amorphous silica oxynitrophosphide (SiONP) overlays with varying levels of O/N/P ratios were thoroughly characterized (EDS, Raman, XANES analysis). In the second part of this study, SiONP coated samples were investigated for cell-surface interactions and their osteogenic and angiogenic behavior in-vitro using osteoprogenitor cells (MC3T3) and Human umbilical vein endothelial cells (HUVEC) respectively. The third and the most important part of this study contained in-vivo evaluation of these biomaterials for their bone-regeneration capability in a rat critical size calvarial defect model using control samples (SiOx, SiNx, substrate only, empty defect).

Fabrication of SiONP Coated Samples and its Effect on Osteogenesis and Angiogenesis Preparation of Nanofabricated SiONP samples. The samples with amorphous silica based overlays were prepared using conventional photolithography followed by plasma enhanced chemical vapor deposition (PECVD) process. The fabrication process started with a single-side polished, p-type (100) orientation test grade silica wafer (Nova Electronic Materials, Flower Mound, Tex.). After standard RCA cleaning of the wafer, positive photoresist (Shipley S1813) was spin-coated at 4000 rpm for 30 sec to obtain a uniformly thick layer of photoresist (~1.35 µm). Microposit HMDS primer was used as an adhesion promoter between the photoresist and the substrate surface. The primer was spin coated at 3000 rpm for 30 sec and baked on hot plate at 150° C. for 90 seconds before spinning the photoresist. The wafer with primer and the photoresist was then exposed to UV using EVG Aligner (I-line 365) at a dose of 139 mJ/cm$^2$ in constant intensity mode and developed for 43 sec in MF-319 developer followed by hard bake (115° C., 60 sec) to obtain the micro-grating pattern on the surface of the wafer.

After photolithography, the exposed Si surface was etched (200 nm etch depth) using deep reactive ion etching (DRIE) process in order to transfer the photoresist patterns into the underlying Si surface. TRION Deep Reactive Ion Etching System with $CF_4$ at 25 sccm gas flow rate, 25 mTorr pressure, 3000 W ICP power and 100 W RIE power etched Si at an etch rate of 862.5 Å/min. The photoresist was then removed completely by immersing the wafer in acetone and followed by piranha clean ($3H_2SO_4$: 1 $H_2O_2$) at 95° C. for 10 min. The wafer was rinsed in DI water and blow-dried under nitrogen.

The patterned wafer was used to deposit a uniform (non-uniformity <1%) 100 nm thick oxide layer via PECVD process using TRION ORION II PECVD/LPCVD system. The oxidized wafer was then coated with 100 nm of amorphous silica oxynitrophosphide (SiONP) overlay. All coatings were fabricated at a substrate temperature of 400° C., chamber pressure of 900 mTorr, and ICP power of 30 W with a 13.56 MHz excitation frequency applied. Source gases included silane ($SiH_4$) and phosphine ($PH_3$) diluted in argon (Ar) (15% $SiH_4$/2% $PH_3$/85% Ar), nitrous oxide ($N_2O$), nitrogen ($N_2$), and ammonia ($NH_3$). The silane flow rate was kept low at 24 sccm (15% $SiH_4$) to prevent undesirable gas-phase reactions, and the silane to phosphine ratio was kept constant due to source gas limitations. The nitrogen and ammonia flow rates were kept high at 225 sccm and 50 sccm, respectively. Six different types of coatings were prepared by varying the nitrous oxide flow rate as shown in Table 10.

The refractive indices and the thickness of the wafer coatings were measured using ellipsometry at a wavelength of 632.8 nm (LS300, Gaertner Scientific Corporation, Skokie, Ill., USA), and results were confirmed through the use of a reflectometer (Ocean Optics NC-UV-VIS TF Reflectometer) and a scanning electron microscope (SEM, S-3000N, Hitachi High-Tech, Tokyo, Japan). From the thickness measurements and plasma-on times, deposition rates were also determined. The wafer was cut into 12×12 mm$^2$ sections for post-process characterization and in-vitro testing.

SEM and EDS Evaluation: Surface morphology, film composition, and film thickness were investigated using scanning electron microscopy (Hitachi S-3000N Variable Pressure SEM) equipped with an energy dispersive X-ray spectrometry system (EDAX). SEM images were taken with an acceleration voltage of 20 keV and scans for EDX mapping and compositional studies were taken at 12 keV to prevent interference from sub-coating layers. EDAX software was used to quantify spectral mapping data from 50 µm×50 µm areas. Four regions of interest (ROIs) corresponding to Si, O, N, and P Kα lines were defined and compositional information was calculated using EDAX's proprietary ZAF method.

Surface Dissolution Studies Using Inductively Coupled Plasma Optical Emission Spectrometry (ICP-OES) Characterization: ICP-OES analysis was performed at the Shimadzu Center for Advanced Analytical Chemistry using the Shimadzu ICPE-9000 ICP-OES system. 12 mm×12 mm wafer sections were placed in 4 mL of α-MEM at 37° C. and 5% $CO_2$ for 0, 6, 12, 24, 48, 96, and 192 hours. After soaking, 25×, 50× and 100× dilutions were used to investigate silica content in the supernatant fluid. Aluminum was used as an internal standard, and the concentration measurements were taken from the α-MEM dissolution media in order to evaluate the surface degradation kinetics of the coatings. Single-element high purity ICP Al and Si standards (1000 µg/L) were purchased from Ultra Scientific.

In-Vitro Studies to Investigate Cell-Surface Interactions for SiONP Samples

Cell Culture Studies for Osteogenic Behavior of SiONP samples. Cells were seeded on the SiONP test samples and glass cover slips (control surfaces) seated on the 6-well plate (BD, Franklin Lakes, N.J., USA). Triplicate samples were seeded with cells at the number of 100,000/well and these cells were synchronized (α-MEM, 1% FBS, 1% streptomycin/penicillin) for an additional 48 hours. Medium was then exchanged for growth media (α-MEM, 10% FBS, 1% streptomycin/penicillin) with 50 ppm ascorbic acid-2-phosphate (AA2P, Sigma-Aldrich Corp., St. Louis, Mo., USA) to induce differentiation. Cells were cultured for 6, 24, 48, and 72 hours before they were lysed for relative gene expression analysis.

Cell Culture Studies for Angiogenic Behavior of SiONP samples: Matrigel® Matrix (Basement Membrane Phenol-red free), Endothelail cell Basal media (EBM), Endothelail cell growth media (EGM-2), Human umbilical vein endothelial cells (HUVECS) were purchased from Lonza Wakersville, Inc., while Glutaraldehaide 2% and Dulbecco's phosphate buffer solution from Sigma Life Science.

Initially, the cells were culture in 75 cm2 flaks with vent cap and allowed to grow for one passage. After that they were detached and used for the following experiment. The 12 well plate, 100 µl pipette tips and iced histology plate were placed on −20 degrees Celsius overnight. The Matrigel 1 ml aliquots tubes were stored at −20 degrees Celsius and then were placed on ice over night at 4 degrees Celsius.

The present study method was based on Arnaoutova and Kleinman's publication 1 and Lonza Wakersville, Inc. (protocol2.) on capillary tube formation. In this study, three different groups were used: glass cover slip (control), SiON and SiONP PECVD coated scaffolds, with 3 samples per group. The scaffold dimensions were (1.2×1.2 cm) and the glass cover slip was 1.5 mm diameter. The scaffolds and glasses cover slip were sterilized using an incinerator 24 hours before cell seeding and placed in 4 degrees Celsius overnight. Previously to the cell seeding, the plate was placed on histology cooled plate inside the cell culture hood and exposed to UV light for 30 minutes. After that the 50 µl of Matrigel® was placed on top of each scaffold and glass cover slip in a way that the whole surface was coated, without bubbles and the plate was put 30 minutes inside an incubator on temperature of 37 degrees Celsius in a humidified atmosphere containing 5% CO2. Then, 65,000 cells/cm2 were seeded on Matrigel® in 100 µl of EGM. The well was maintained inside the incubator for 30 minutes and later filled up to 2 mL with EGM.

After 6 hours the wells were washed with PBS followed by DI water and fixed with Glutaraldehyde 2.5% and dehydrated by ethanol graduation using refined aspiration of solutions by 30 G needles to prevent Matrigel® and cells removal. The samples were removed from the well to prevent attachment to the bottom of the well and allowed to dry for 24 hours at room temperature and finally coated with gold for 30 seconds. Pictures were captured using Hitachi S-3000N variable pressure Scanning electron microscopy using high vacuum, working distance of 12.8 mm and beam acceleration voltage of 15.0 KV.

Data was collected using image J by measuring the total tubes length and thickness. It was taken 2 pictures per scaffold using SEM as mentioned above and Neuron J, (image J plug-in) was used for total tubes length and 10 measurements were collected from each picture to measure the thickness.

Data were presented as the mean±standard error. One-way analysis of variance (ANOVA) was used for parametric analyses and p<0.05 was used for statistical significance. Posthoc student T-test was used for between group comparisons and p<0.05 was used to establish statistical significance.

qRT-PCR Analysis for Osteogenic Gene Expression Studies. For gene expression studies, cells were seeded at a density of 100,000 cells $cm^{-2}$ in 6-well plates. The cells were lysed to collect mRNA (RNeasy Mini Kit, Qiagen, Valencia, Calif., USA), converted to cDNA using qRT-PCR method (Reverse Transcription System, Promega, Madison, Wis., USA) according to the manufacture's protocol. Absorbance measurements of mRNA and cDNA samples were performed using a microvolume Uv-Vis spectrophotometer (Nano Drop 2000c, Thermo Fisher Scientific Inc., Waltham, Mass., USA). Using glyseraldehyde-3-phosphate dehydrogenase (GAPDH) as internal reference gene, relative quantification of gene expression was evaluated by the comparative cycle threshold (CT) method and fold change calculated using $2^{-\Delta\Delta CT}$. Details regarding qRT-PCR were given in our previous work [16]. The gene expressions of GAPDH, SOD1, OCN, RUNX2, Smad1, Smad5, Osterix (Sp7), and COL(I)-α1 were studied for 6, 24, 48 and 72-hour time points.

In-vivo Testing of SiONP samples using Rat Cranial Defect Model: Surgical and Postoperative Protocol. All procedures involving animals were performed in accordance with a protocol approved by the Institutional Animal Care and Use Committee at Baylor College of Dentistry, Texas A&M University A critical size calvarial defect model was developed to assess the bone healing efficiency of Si(ON)x materials when placed in biological environment. Adult male rats (about 430 g each) were selected to study the osteoinductive properties of the proposed material in relatively slower bone-healing subjects. The rat was initially weighed and placed into an induction chamber for anesthesia. It was anesthetized at 5% isoflurane in oxygen for about 2-3 minutes, then shaved the calvaria and held its head onto a stereotaxic frame. The surgery started with an incision (about 1.5 cm) made by a scalpel blade. The periosteum layer was scratched down using the scalpel blade and the incision site was iteratively washed with sterile saline followed by the air blow to dry the exposed skull bone. The sterilized SiONP test sample (3 mm×5 mm) was placed at exact location where we wanted to implant it and marked the boundary with a marker on dry skull. The defect site was chosen to have maximum flat surface with minimum sutures involved. Then, the dental bur (#1 or #2) with about 0.5 mm diameter tip was used to precisely cut the bone along the drawn boundary to create the critical sized calvarial defect without nicking the dura. After creating the bone defect, the defect site was thoroughly washed with sterile saline followed by the air blow to get it dry. A small amount (~1-2 μl) of gel glue was put on the bottom surface of the implant and placed it upside down in the defect so that it is glued to the dura and doesn't move during healing. Finally, monofilament taper point suture needle was used to suture the incision site making square knots and ensuring adequate space to allow skin healing. The incision site was cleaned thoroughly and a small volume (80-100 μl) of painkiller/sedative medicine (nalbuphine) was injected intramuscularly using 1 ml syringe. The rat was observed for behavioral study to record any signs of pain/distress for the next few days and then allowed 5 weeks for healing before analyzing the effect of SiONP based material on bone regeneration.

Micro-level computerized tomography (μCT) Scan: The implants with the surrounding calvarial bone were extracted out after 5 weeks of recovery time and were analyzed using an X-ray microCT imaging system (μCT 35, Scanco Medical, Basserdorf, Switzerland). The unit consists of an x-ray source directed towards a specimen holder that hosts bone-implant samples. Serial tomographic imaging at an energy level of 55 kV and intensity of 145 μA for the samples was performed. 3D micrographs were generated to evaluate different sample surfaces for the fracture healing after the same recover time. The lower and upper threshold values used for this analysis were 280 and 1000 respectively.

X-ray Absorbance Near Edge Structure (XANES) Spectroscopy: XANES spectroscopy was performed at the Canadian Light Source at the University of Saskatchewan in Saskatoon, Saskatchewan, Canada. XANES is a very sensitive and advanced technique to characterize the local coordination of individual elements, by using the fine structural features at the absorption edge [22]. Since the bone mineral is mainly made of calcium phosphate apatite, therefore calcium (Ca) and phosphorous (P) edges are mostly investigated for bone analysis to determine the nature and local coordination of Ca and P in bone [23-25]. The Ca and the P K-edge spectra were obtained over the energy range of 2140-2190 eV and 4000-4130 eV, respectively using soft X-ray beam-line for the micro-characterization of materials (SXRMB) beam-line. The step size for Ca and P K-edge spectra were 0.3 and 0.25 eV respectively. Plane Grating Monochromator (PGM) beam-line was used to acquire the P L-edge spectra in the region of 130-155 eV. PGM operates at the low energy range between 5-250 eV and a step size of 0.1 eV.

Raman Spectroscopy: Raman spectroscopy is a very convenient and valuable technique to analyze biological samples without need for staining, fixation or sample preparation but needs a relatively high-power laser beam to overcome the inherent low Raman scattering efficacy of biological molecules [26, 27]. Microspot Raman spectroscopy (DXR, Thermo Scientific) with 780 nm laser source and 100 mW power was used to characterize the extracted bone sample. Different regions (A, B, C, D) on the extracted sample were analyzed to evaluate the newly grown bone chemistry in comparison to the old bone. The phosphates, amides and other significant peak intensities were used to gauge the mineralized content and the phosphorylation of the bone.

Raman spectroscopy data was analyzed to study the composition and the maturity (mineralization) of the newly formed bone after 5 weeks of recovery time. Intensity of $PO_4^{3-}$ peak at 950 $cm^1$ is proportional to mineralized content of the bone. Peaks at 955 $cm^1$ and 957 $cm^{-1}$ indicate transient bone mineral phase from the immature bone. Peak at 853 cm$^1$ and 872 cm$^-$ indicate presence of collagen proline and hydroxyproline respectively. Peaks at 1242 and 1272 cm$^{-1}$ represent Amide III protein β sheet and protein α helix respectively. Peak at 1446 cm$^{-1}$ corresponds to protein CH$_2$ deformation and 1660 cm$^1$ is the strongest Amide I peak with high polarisation sensitivity. Prominent shoulder at 1690 cm$^1$ are indicative of immature cross links, β sheets and disordered secondary structure. The results (FIGS. 48A-48D) demonstrated that the surrounding bone (A), non-defected original surrounding bone, showed all the peaks expected to be present in a mature rat bone. The newly formed bone (C), at the boundaries of the initially created defect (adjoining surrounding bone), showed the peaks much similar to the old bone and appeared fully mineralized indicated by the $v_1PO_4^{3-}$ peak intensity. The full width half maximum of $v_1PO_4^{3-}$ is proportional to c-axis length of crystal and hence proportional to maturity of the crystal. The content of mineralization decreased as we moved towards the center of the defect, indicated by drop in the intensity of $v_1PO_4^{3-}$ band indicating less phosphate present. At the far end of the newly formed bone towards SiONP surface (B), we observed distinct peaks for collagen presence as well Amide III and Amide I formation and CH$_2$ deformation. This indicates protein presence and some immature mineralized content. Whereas in the middle of the SiONP sample (D), peaks for Amide III, Amide I and CH$_2$ deformation were seen but there was no collagen or phosphate-carbonate presence indicating no mineralization occurred. Also a distinct peak showing Si—Si bond was recorded, which might have stemmed from the underlying silica substrate.

SEM of Extracted Bone Samples: The extracted bone samples were completely dried and a thin layer of gold (50 nm) was coated on the surface to make it conductive for electron microscopy. Samples were imaged using a scanning electron microscopy (SEM, JOEL USA Inc., Peabody, Mass., USA) with secondary electron mode at 5-15 kV energy to get the finest results.

Histology: The extracted bone samples were embedded in methyl methacrylate and sectioned using slow speed diamond saw. The sections were then stained using Stevenel's Blue stain and Van Gieson Picro-Fuchsin counterstain and imaged by using Leica TCS SP5-II upright microscope.

Statistical analysis: Data were presented as the mean standard error. One-way analysis of variance (ANOVA) was used for parametric analyses and p<0.05 was used for statistical significance.

The refractive indices and deposition rates for each set of gas flow conditions was determined using ellipsometry. Refractive index inhomogeneity was determined to be less than 0.007 and the thickness non-uniformity as measured at 15 points on each 4" wafer in the range of 1.6-2.8%. The refractive indices ranged from near that of silica nitride (Si3N4 n=2.0) to near than of silica dioxide (SiO2 n=1.46) [28]. Deposition rate decreased and refractive index increased as flow of nitrous oxide decreased which is expected as N$_2$O is the primary source of oxygen that is incorporated into the film Refractive index of the samples as a function of the ratio of the flow rates of the primary reactive gases, N$_2$O and SiH$_4$, has been plotted. The SiH4:PH3 ratio is a constant, so a similar general trend of index vs. N2O:PH3 flow rate also exists.

EDS mapping showed no major carbon or other contaminants and a uniform elemental distribution normal to the wafer surface. A ZAF quantification method was used to determine the atomic % of each element in the coating. The coating composition of the SiONPx coatings in terms of atomic % of Si, O, N, and P was examined. Increasing N$_2$O:SiH$_4$ flow ratio increased oxygen to nitrogen content as well as an unanticipated modest increase in the P content of the coatings. In the sample deposited with 0 sccm N$_2$O flow, some oxygen is still observed in the coating. This may be due to oxidation of the surface post-deposition, or contamination from the component gases or the deposition chamber itself. For the sample range studied, silica content was found to be relatively independent of the N$_2$O:SiH$_4$ flow. The silica content of the samples was found to be between 56.7-64.7 atomic % as shown in Table 11.

TABLE 10

Gas flow rates for the deposition of six different SiONP coating chemistries

Table 10 - Gas Flow Rates (sccm)

| Sample | 15% SiH$_4$/ 2% PH$_3$/ 83% Ar | N$_2$O | N$_2$ | NH$_3$ |
|---|---|---|---|---|
| 1 | 24 | 0 | 225 | 50 |
| 2 | 24 | 3 | 225 | 50 |
| 3 | 24 | 5 | 225 | 50 |
| 4 | 24 | 16 | 225 | 50 |
| 5 | 24 | 155 | 225 | 50 |
| 6 | 24 | 160 | 225 | 50 |

TABLE 11

EDS Compositional data (at %), Atomic SiONP coatings as determined by EDS Analysis

| Sample | Si | O | N | P |
|---|---|---|---|---|
| 1 | 64.0 | 2.1 | 33.7 | 0.24 |
| 2 | 64.8 | 4.2 | 30.8 | 0.25 |
| 3 | 61.8 | 7.3 | 30.5 | 0.28 |
| 4 | 58.7 | 14.2 | 26.8 | 0.27 |
| 5 | 57.1 | 38.6 | 4.0 | 0.38 |
| 6 | 56.74 | 39.6 | 3.26 | 0.45 |

ICP-OES analysis shows that initially, there was little silica in αMEM solution, however, all samples rapidly (<30 mins) begin to release silica into solution. Sample 6 appears to undergo the most rapid release and completely releases all silica after 8 hours in solution. Sample 5 appears to have completely released all silica after 96 hours in solution while samples 1 and 2 only appear to mostly release their silica after 192 hours in solution. The higher oxygen-content samples appear to have more rapid release rates than the low oxygen content samples. It should be noted that the higher oxygen content samples also contain more phosphorous, which is known in bioactive glass formulations to help control dissolution rate.

It is instructive to look at silica release in terms of the percentage of the thickness of the coating dissolved; however, in order to estimate this quantity some simplifying assumptions must be made. First of all, the coatings are assumed to be chemically and structurally uniform in the direction normal to the surface. Secondly, since the exact densities of the coatings are unknown, a reasonable approximation would be to use the density of similar low-temperature fabricated PECVD coatings. According MIT's material property database, low-temperature PECVD deposited silica has a density of about 2.3 g/cm$^3$ [30] while similarly fabricated nitride has a density of about 2.5 g/cm$^3$. Since these coatings have a known composition that is intermediate to these two extremes, these values can be used to calculate the total amount of silica that is able to go into solution and a % of coating thickness lost as a function of time can be determined. Table III lists coating thickness remaining for four of the sample chemistries as a function of time in dissolution calculated according to this method.

Negative values as shown indicate that more silica is found in solution than is found in the original SiONPx coating; this may be due to a limited amount of silica release from the exposed silica layer underneath the coating itself but is it likely due to the error in the sample measurement. This treatment of the data shows that the highest nitrogen content sample 1 is most likely the only coating that has not completely dissolved after 8 days in solution. Moreover, it was also desired to determine if there was an effect of the surface chemistry on osteogenic markers expression. Therefore, relative expression of several genes associated with osteoblast differentiation was studied using MC3T3 cells and the human periosteum cells. The results for MC3T3 cells showed that expression of SOD1 was significantly increased at 6 hours after induction of differentiation (4 to 6 times relative to control glass cover slip group), and settled down to same level at 24 hours. The transcription factors Runx2 and Sp7, were chosen for measurement due to their involvement in their osteoblastic differentiation and mineralization. The transcription factors Runx2 and Sp7 showed the same trend as SOD1 gene expression, but their reduction was moderate compared to SOD1. The gene expression of OCN on wafer sample was remarkably increased at 6 hours, and continued until 48 hours after induction of differentiation. The gene expression of Col(I)-α1 showed up-regulate and down-regulate alternately at these time points but maximal enhancement was observed at 6-hour time point. Similarly, smad1 and smad5 also showed much enhanced expression at 6-hour time point but settled down at later time points.

The angiogenic studies show that after 6 hours the HUVECS formed tubes on top of glass cover slip, and PECVD scaffolds SiON and SIONP. It was not verified statistical difference of total tubes length among the groups, however the thickness of the tubes was significantly higher at SiONP group as we can see on FIG. 6. Moreover, we can disadvantageously observe some incomplete tubes on glass cover slip and SiON scaffolds. The tubes on SiONP scaffolds have a well-defined circular structure without incomplete branches.

The implant was extracted out after allowing 5 weeks of recovery. The extracted bone-implant sample showed a strong fixation of the implant with the surrounding bone whereas micro-level computerized tomography (μCT) scan confirmed the presence of hard mineralized newly formed bone that filled most of the space around the SiONP coated implant. On the other hand, controls samples were found mobile and loosely connected to surrounding bone via soft tissue when extracted out after 5 weeks. The micro-CT data revealed that no significant regeneration of new bone occurred to fill the interfacial gaps for control samples during the same recovery time. Similarly, negative control (empty defect) showed no signs of sufficient healing and confirmed that the defect was critical size and would not heal at its own. This key aspect indicates the superiority of the SiONP survaces as compared to the SiON surfaces.

Raman spectroscopy data was analyzed to study the composition and the maturity (mineralization) of the newly formed bone after 5 weeks of recovery time. Intensity of $PO_4^{3-}$ peak at 950 cm$^{-1}$ is proportional to mineralized content of the bone. Peaks at 955 cm$^{-1}$ and 957 cm$^{-1}$ indicate transient bone mineral phase from the immature bone. Peak at 853 cm$^{-1}$ and 872 cm$^{-1}$ indicate presence of collagen proline and hydroxyproline respectively. Peaks at 1242 and 1272 cm$^{-1}$ represent Amide III protein β sheet and protein α helix respectively. Peak at 1446 cm$^{-1}$ corresponds to protein $CH_2$ deformation and 1660 cm$^{-1}$ is the strongest Amide I peak with high polarisation sensitivity. Prominent shoulder at 1690 cm$^{-1}$ are indicative of immature cross links, β sheets and disordered secondary structure. The results (FIGS. 48A-48D) demonstrated that the surrounding bone (A), non-defected original surrounding bone, showed all the peaks expected to be present in a mature rat bone. The newly formed bone (B), at the boundaries of the initially created defect (adjoining surrounding bone), showed the peaks much similar to the old bone and appeared fully mineralized indicated by the $v_1PO_4^{3-}$ peak intensity. The full width half maximum of $v_1PO_4^{3-}$ is proportional to c-axis length of crystal and hence proportional to maturity of the crystal. The content of mineralization decreased as we moved towards the center of the defect, indicated by drop in the intensity of $v_1PO_4^{3-}$ band indicating less phosphate present. At the far end of the newly formed bone towards Si(ON)x surface (C), we observed distinct peaks for collagen presence as well Amide III and Amide I formation and $CH_2$ deformation. This indicates protein presence and some immature mineralized content. Whereas in the middle of the Si(ON)x sample (D), peaks for Amide III, Amide I and $CH_2$ deformation were seen but there was no collagen or phosphate-carbonate presence indicating no mineralization occurred. Also a distinct peak showing Si—Si bond was recorded, which might have stemmed from the underlying silica substrate.

The results from the XANES data were analyzed to study the coordination chemistry of the newly grown bone as compared to the surrounding bone.

Example 19—Se$^+$ Enhances Tissue Angiogenesis

The present example demonstrates that the presence of Si enhances tissue healing and angiogenesis compared to that tissue healing and angiogenesis observed in the absence of Si. (See FIGS. 50A-B, 51A-D, 52A-I, 53A-D, 54A-D, and 55A-B).

The present example demonstrates that Si$^{4+}$ at specific concentration(s) can enhance viability, migration and capillary-like tube formation of HUVECs. Moreover, it can reduce death and enhances viability in HUVECs under harmful $H_2O_2$ concentrations. This experiment mimics the situation where the cells after injury are exposed to hypoxia and production of high concentration of reactive oxygen species (ROS). High levels of ROS can induce cells death and difficult tissue healing. The present example demonstrates the effect of Si ion on HUVECS under harmful oxidative stress and the role of this element on angiogenesis on early stages of tissue repair.

Trace elements are essential for bone health. Presence of ions such as, lithium, zinc, magnesium, silica, strontium and others have shown to enhance osteogenesis and angiogenesis. However the mechanism of many of them is still unclear.

Material and Methods: Silica ion and Hydrogen peroxide solutions preparation: Specific Si$^{4+}$ solution was prepared by dissolving sodium meta-silicate—$Na_2SiO_3$ (1 mol l-1) in sterile water, after preparation the solution was filtered using a nylon syringe filter, 33 mm, 0.2 um, 50/PK and followed by serial dilutions in endothelial cell culture media-2 (Lonza Walkersville, In) until it reached the desired Si$^{4+}$ concentrations: 0.1 mM, 0.5 mM and 1 mM. Hydrogen peroxide—$H_2O_2$ 30% (w/v) was used as source of ROS and was diluted with sterile water followed by filtration, as mentioned above, it was serially diluted in sterile water until desired $H_2O_2$ concentrations: 0.2 mM, 0.4 mM, 0.6 mM, 0.8 mM, 1 mM and 1.5 mM. The last dilution was made in the well plate with specific endothelial cell media.

Cell culture: Human umbilical veins endothelial cells (HUVECs)—(Lonza Walkersville, In) were thawed and sub cultured in 75 cm2 Corning® cell culture flasks with canted neck and vented caps following manufacturer's protocol [21]. It was used endothelial cell growth media 2 (EGM-2)—(Lonza Walkersville, In) for HUVECs expansion and the media was changed every 2 days until the cells reach 70% confluence, then the cells were subcultured. Cells from passage 3 were used on all designed experiments.

HUVECS viability exposed to different $H_2O_2$ concentrations. 10,000 cells were seeded in a 96 well plate using a total volume of 100 μl of specific cell culture media (n=12/group) according with the group to be studied: EGM was used as control and the other 6 groups were formed by $H_2O_2$ concentrations mentioned above diluted in sterile water placed on the bottom of the well before the reduced EGM. The latter was prepared by diluting EGM with EBM for a final concentration of 20% (v/v) and is labeled on this manuscript as EGM 20%. The experiment ended after 6 and 24 hours, and 6 samples were used per time point for Calcein-AM (BD, Biosciences, CA) fluorescent staining and other 6 for CellTiter 96® AQueous One Solution Cell Proliferation Assay (MTS). First, the cells were prepared for proliferation assay, and it was prepared solution using 1 ml of endothelial cells basal media (EBM) per each 100 μl of reagent. After specific time point, the cell culture media was removed from each well and 120 μl of prepared solution was placed inside the well. After 3 hours 60 μl were collected and placed in a new 96 well plate, which was read using a microplate reader at 490 nm wave length. Second, 50 μl of Calcein-AM 2 mM was added into other 6 wells/group, waited 30 minutes and fluorescent pictures were taken using Carl Zeiss Axio Vert A1 TL/RL LED Inverted Microscope and FITC light filter.

Silica ion effect on HUVECS under normal conditions: 5,000 cells were seeded per well, n=12 per group in 5 groups: EGM 20% (negative control), EGM (positive control), EGM 20%+Si 0.1 mM, Si 0.5 mM, and Si 1 mM. All groups with silics ion were prepared with EGM 20% with the aim to give more sensitivity to changes induced by the different $Si^{4+}$ concentrations on HUVECs. With the aim to verify what should be the best EGM dilution for this experiment the cells were cultivated in EGM diluted in three different concentrations and EGM 20% showed after 24 hours significant difference (p<0.01) in cell proliferation relative to control. The data was collected using the same methods mentioned on section 2.3, using MTS assay and Calcein-AM fluorescent staining pictures. Additionally, the fluorescent pictures were used for cell counting on ImageJ, v1.47 (National Institutes of Health, Bethesda, Md.).

Capillary-Like Tube Formation Assay Under Different $Si^{4+}$ Concentrations

HUVECs seeded on bed of Matrigel: The study groups were the same used as described above, n=6 per group. The experiment was conducted according to previous publications[21][22]. In summary, the study was conducted as follows: first, 50 μl of Matrigel® Matrix (Basement Membrane Phenol-red free) was placed on the bottom of well and placed in an incubator at 37° C., 95% relative humidity and 5% $CO_2$ for 30 minutes. Second, 15.000 cells were seeded per well using 100 μl of specific media and/or $Si^{4+}$, such as it was mentioned above. The well plate was maintained in the incubator for 6 hours and after that was stained with Calcein-AM following the same method mentioned on section 2.3. Lastly, after 30 minutes 3 different pictures were captured per well using a Zeiss fluorescent microscope FITC filter in 5× view and angiogenesis analyzer ImageJ plugin [23] was used for measurements. The collected data was based on number of nodes, number of meshes, number of segments, total tube length and number of junctions.

HUVECs seeded on well plates without Matrigel: 4 groups were used for capillary-like tube formation without Matrigel, EGM (control) and the three silica ion concentrations describe above. 15.000 cells were seeded per well (n=5 per group) in a 96 well plate using 100 of Growth media and after 24 h the media from 3 groups was changed to media with three different silica ion concentrations and growth media for the control. Three hours after media change the cells were stained with Calcein AM following protocol described above. Three different 5× views were captured per well using fluorescent microscope and ImageJ was used for calculations and the results were presented on number of connected networks formed, which means conformational cells change such as capillary precursor structure.

Scratch wound healing assay: This study used 3 groups (n=3/group): EGM-2 (positive control), EBM-2 (negative control) and $Si^{4+}$ 0.5 mM+EBM-2 (treatment). Initially, wells were seeded 50,000 cells/well and waited until wells reached around 90% cell confluence. After, a 200 μl pipette tip was used for make a scratch in a cross shape, the media was removed and each well was carefully washed twice with phosphate buffer solution (PBS) and the new media was added according to the group. A 5× bright field picture was taken just after add new media (t0). At the end, after 12 hours (t12), the cells were washed with PBS, fixed with 4% paraformaldehyde solution and stained with toluidine blue. Pictures were captured from the same area such as was made on t0 and the percentage of occupied area at t12 was calculated using Wound Healing ImageJ software plugin.

Transwell migration assay: The migration by transwell membrane was tested in triplicate samples per groups: EGM (positive control), EBM+2% FBS (negative control) and EBM+2% FBS+$Si^{4+}$ 0.5 mM (treatment). 30,000 cells were seeded in the upper chamber of 8 micron Transwell (Castor Inc) on 100 μl EBM. After, 600 μl of studied media was placed on the bottom of the well and cells were allowed to migrate for 12 hours through the micropores, then fixed with 4% paraformaldehyde solution. After fixation the cells from the upper part of the well were removed by a cotton swab and the remained cells (bottom/migrated cells) stained with DAPI (P369, Invitrogen) for nuclei Finally, it was captured 3 pictures per well in a 5×, 10×, 20× and 40× view using Zeiss fluorescent inverted microscope and ImageJ software was used for cell counting.

Effect of Si on HUVECS Under Harmful Hydrogen Peroxide Level.

Cell viability: The solutions and cells suspensions preparation followed the method mentioned on section 2.3 and 2.4. The experiment was formed by three groups: 1—EGM, 2—EGM+11202 0.6 mM and 3—EGM 11202 0.6 mM+Si 0.5 mM (treatment). $H_2O_2$ 0.6 mM and $Si^{4+}$ 0.5 mM were used based on the results observed on previous sections. It was used 7,500 cells/well and seeded in a 96 well plate, twelve samples per group. The data was collected after 6 and 24 hours, 6 samples/group were used for MTS assay and 6 for live and dead fluorescent staining with Calcein-AM and propidium iodite. Three samples were used for Calcein AM and 3 for propidium iodite. Staining was done separately with the aim to minimize the false negative and artifacts for dead floating cells cell. The Calcein-AM followed the method mentioned above and the propidium iodite.

Quantitative real-time polymerase chain reaction (qRT-PCR): 500.000 cells were seeded in a 6 well plate (n=4/group) and culture for 24 hours. The groups were the same used for viability (section 2.8.1). First, the cells were lysed using buffer RLT (guanidinum thiocyanate) 10 µl β-Mercaptoethanol per 1 mL of buffer. Second, the cells were sheared with rubber scrapper under mild pressure to lyse the cells and collect mRNA (RNeasy Mini Kit, Qiagen, Valencia, Calif., USA), converted to cDNA using qRT-PCR method (Reverse Transcription System, Promega, Madison, Wis., USA) according to manufacture's protocol. mRNA and cDNA were quantified during the process using micro-volume UV-VIS spectrophotometer (Nano Drop 2000c, Thermo Fisher Scientific Inc., Watham, Mass., USA). 18S was used as housekeeping for reference gene to be consider more specific to HUVEC cells[24] and GAPDH was also used as housekeeping for better comparison with other studies. Lastly, relative quantification of gene expression was evaluated by comparing cycle threshold (CT) method and fold change calculated using $2^{-\Delta\Delta CT}$. The studied genes included VEGFA, KDR and HIF1-α. (Table 12).

recoverable levels when exposed to a harmful $H_2O_2$ concentration. Moreover, the Calcein-AM fluorescent pictures (FIG. 50 B1) corroborate with MTS assay results showing the reduction of viable cells in both time points.

Silica Ion Effect on HUVECs Under Normal Conditions

Cell viability: All groups presented an increment on the cells number compare with initial cell seeding. After 6 hours the $Si^{4+}$ 1 mM was the only group who presented a significant difference and relative cells number was lower than the others (1.19±0.11 folds) (p<0.05). At 24 hours $Si^{4+}$ 0.5 mM presented a significant higher level (3.21±0.05 folds) (p<0.05) compare with others silica concentrations and negative control (EBM), and significant lower than positive control (EGM) (3.95±0.07 folds) (p<0.05). Lastly, $Si^{4+}$ 1 mM presented a significant lowest relative cells number (1.89±0.11 folds) (p<0.05). (FIG. 50A).

Cell Proliferation

After 6 hours the groups with silica ion presented similarly 1 fold more relative cell number than controls groups (p<0.05). At 24 hour time point, positive control (EGM) group presented the best result (4.6±0.22 folds) (p<0.05) and $Si^{4+}$ 1 mM the worst (3.04±0.11 folds). 48 hours after initial cell seeding positive control had the highest relative cell increment (8.04±0.42 folds) (p<0.01). Nevertheless, among the silica ion groups the $Si^{4+}$ 0.5 mM (4.39±0.28 folds)

TABLE 12

Primer sequences of genes, related with endothelial cell functions, including VEGF, VEGFR2, HIF-1α as studied genes, and 18S and GAPDH as a housekeeping, which were used for the quantitative RT-PCR.

| Primer | Forward | Reverse |
| --- | --- | --- |
| VEGFA | F: 5'-TGCGGATCAAACCTCACCA-3' (SEQ ID NO. 1) | R: 5'-CAGGGATTTTTCTTGTCTTGCT-3' (SEQ ID NO. 2) |
| VEGFR2 | 5'-GTGATCGGAAATGACACTGGAG-3' (SEQ ID NO. 3) | R: 5'-CATGTTGGTCACTAACAGAAGCA-3' (SEQ ID NO. 4) |
| HIF1-α | 5'-CCATGTGACCATGAGGAAAT-3' (SEQ ID NO. 5) | R: 5'-CGGCTAGTTAGGGTACACTT-3' (SEQ ID NO. 6) |
| 18S | F: 5'-CAGCCACCCGAGATTGAGCA-3' (SEQ ID NO. 7) | R: 5'-TAGTAGCGACGGGCGGTGTG-3' (SEQ ID NO. 8) |
| GAPDH | F: 5'-GATTTGGTCGTATTGGGCG-3' (SEQ ID NO. 9) | R: 5'-CTGGAAGATGGTGATGG-3' (SEQ ID NO. 10) |

Statistical analysis: Data are expressed as means and standard deviation. Statistical analysis was performed using one-way ANOVA with pos-hoc Tukey's pairwise for comparison among more than 2 groups and student t-test when the assessment was between two groups. The significant level was considered when p<0.05. Sample size was calculated based on number of groups and standard deviation from other studies. Past3 statistical software was used foe ANOVA and t-test and G-power statistical software for sample size.

HUVECs Viability Exposed to Different $H_2O_2$ Concentrations

In order to verify which H2O2 concentration was the ideal for our experiment, it was verified cell viability at 6 and 24 hours. FIG. 50A shows the MTS assay and fluorescent pictures. $H_2O_2$ 0.6 mM was the best concentration to be used in the present study, once presented a significant reduction on cell number compare with control (no $H_2O_2$ exposition), 0.45 (±0.21) and 0.63 (±0.34) folds after 6 and 24 hours respectively. Despite the significant reduction $H_2O_2$ 0.6 mM was considered suitable for these studies to maintain cells at presented at least 1 fold more cells than 0.1 mM (3.44±0.25 folds) and 1 mM (3.12±0.34) folds) groups. (FIG. 51B).

After 48 hours the viable cell counting relative to positive control (EGM) showed that media with $Si^{4+}$ 0.5 mM had the best result (0.48±0.16 folds) with 2 folds more cells than the other silica groups (p<0.05) and 5 more than negative control (EGM 20%) (p<0.005). (FIGS. 51C and D).

Capillary Tube Formation

HUVECs Seeded on Bed of Matrigel $Si^{4+}$ 0.5 mM showed the best parameters among all groups on capillary tube formation, especially on number of meshes, which it is closely related with pre-capillary structure maturity. (FIGS. 52A and B)

HUVECS Seeded without Matrigel

Figure 52D:
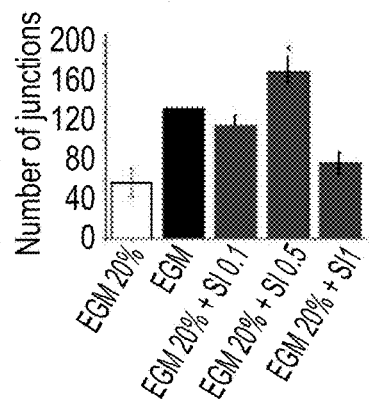
Figure 52E:
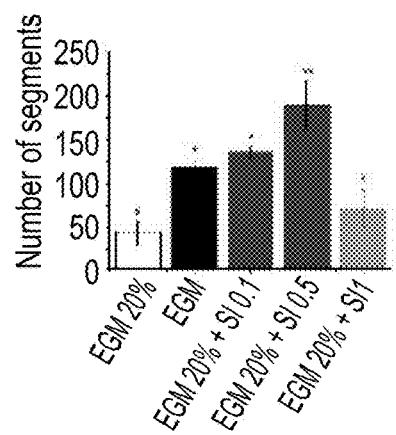
Figure 52F:
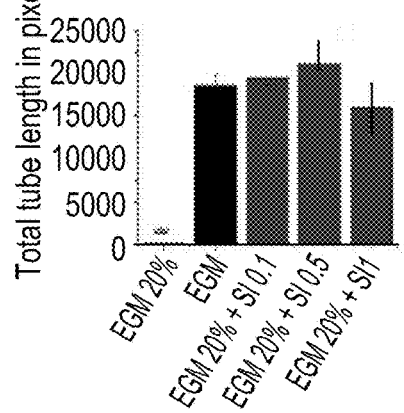

All silica groups presented a conformational cell shape change with the cells tending to from connected networks like a capillary precursor structure (FIG. 52D). All silica groups framed a significantly higher number of connected networks at least 10 fold more than control (EGM). $Si^{4+}$ 0.5 mM was the best group forming 10 fold more connected networks than 0.1 mM (p<0.05) and 20 folds more than 1 mM (p<0.01) groups. (FIG. 52D).

Scratch Wound Healing Assay

After fixation and staining with Toluidine blue the bright field pictures (5× view) show a higher number of cells on scratched area of EGM, followed by EBM+$Si^{4+}$ 0.5 mM. (FIG. 53A). After measurements using Wound healing (ImageJ plug-in) the data analysis shows that addition of $Si^{4+}$ 0.5 mM to EBM improved more than 100% cell migration on scratched area after 12 hours. (FIG. 53 B).

Transwell migration assay: After fix, DAPI staining and capture pictures in 10×, 20× and 40× (FIG. 53C), the number of migrated cells were calculated and data shows that the silica treatment group presented around twice more cells than negative control (EBM+2% FBS) ($p<0.05$). (FIGS. 53C and D).

Quantitative Real-Time Polymerase Chain Reaction (qRT-PCR)

24 hours after cell seeding the cells the cell lysate was collected and analyzed. All groups were compared with control (endothelial cell media) and expressed relative to housekeeping gene18S and GAPDH. The cells exposed to H2O2 0.6 mM presented no difference among the studied genes when compare to control. Cells exposed to silica ion presented significant high expression of all studied genes, the increment was more evident on 18S housekeeping, VEGF (7.13±0.54 folds) ($p<0.01$), KDR (4.92±1.18 folds) ($p<0.01$) and HIF-1α (5.97±2 folds) ($p<0.01$) (FIG. 55A). Similarly but with less intensity, all genes were significant overexpressed relative to GAPDH, VEGF (5.3±1 folds) ($p<0.05$), KDR (4±0.73 folds) ($p<0.05$) and HIF-1α (3±0.86 folds) ($p<0.05$) (FIG. 55B).

The results shows that cells exposed to H2O2 0.6 mM and treated with $Si^{4+}$ 0.5 mM showed a significant over expression compared to control relative to 18S housekeeping gene: VEGFA (3.4±1.35 folds)($p<0.05$), KDR (2.38±0.58 folds), HIF-1α (2.77±1.64 folds) (FIG. 6A). When GAPDH was considered as housekeeping there was significant over expression of VEGFA (4.5±0.99 folds) ($p<0.01$) (FIG. 55B).

HIF-1α activation is a master event in a down-stream signaling of angiogenesis[25] that is necessary for blood vessel invasion and progenitor cells survival in an initially hypoxic damaged environment, where blood vessels do not reach an injured area. Moreover, HIF-1α downstream acts to reduce oxygen consumption and thereby avoids harmful ROS accumulation.

Recent publication showed relation between silica ion released from mesopores microcarries and HIF1-α upregulation by HUVECs under regular cell culture media condition. These results corroborated with these findings and showed additional information of HIF-1α increment on HUVECs exposed to harmful levels hydrogen peroxide.

Vascular endothelial growth factor-A (VEGF) is a crucial growth factor in angiogenesis regulation. Moreover, plays a role on different stages of endocohondral and intraembranous ossification, having a paracrine, autocrine and intracrine effect on osteoblast function during the bone repair [27]. Our results showed that VEGFA gene expression were incremented on HUVECs exposed to silica ion 0.5 mM even when they were under harmful oxidative stress.

Example 20—Characterization of In Vivo Studies Involving SiONP Samples in Rat Cranial Defect Model A rat cranial defect model was conducted as described in example 18, paragraph 00262. This example is an extension from example 17, illustrating the effectiveness of SiONP for healing bone in craniofacial models.

The rats were examined after 5 weeks for signs of inflammation or infection. None was found.

Rats were then euthanized and SiONP samples were recovered from the rat cranium as described in example 18, paragraph 00262.

The samples were prepared for analysis using x-ray absorbance near edge fine structure analysis to determine the mineral phase of bone that was newly grown on the SiONP surface.

To examine the mineral phase formed on these surfaces, the Calcium (Ca) K edge and Phosphorus (P) edge were examined.

FIGS. 55A and 55B show the Ca K edge spectra for various samples studied in the SiONP experiments. It can be seen that SiONP samples after in vivo implantation and recovery from the rat cranium show the presence of Ca—P phases consistent with new bone formation. Here, HA is used as a model compound for comparison of the mineral phase of HA in bone. The Ca K edge peak of HA is different from other model compounds with a pre edge peak at 4039.1 ev. It has a pre edge shoulder at 4044.4 and main peak b at 4048.27 ev. The post edge shoulder corresponds to transition to unoccupied states, mainly 5s states. The main edge peak "b" is assigned to 1 s to 4p transition. The shift in energy towards higher energy levels for peak "b" could represent differences in the type of mineral formed in vitro as compared to the been formed in vivo. The mineral formed in vitro could be amorphous Ca—P (precursor to the formation of HA).

FIG. 56 shows the phosphorus L edge spectra for SiONP samples studied in this experiment. Similar to Ca K edge spectra, the P L edge spectra indicate the newly formed bone on SiONP samples has a similar P structure as that in HA model compounds. The main Peak c is at 137.8 eV, pre edge peak "a" at 135.7 and pre edge peak "b" around 136.5. There is also shoulder after peak "c" around 141 eV and secondary peak d at 146.7 eV. Peak "a" and "b" at the lower energy side are separated by 1 ev and arise from the spin orbit split into 2p electron into $2p_{3/2}$ and $2p_{1/2}$ levels. The main peak "c" is attributed to transitions to 3p orbital made possible due to presence of other elements such as oxygen and cationic species like Si and Ca. The shoulder after peak "c" is characteristic of Ca phosphates and arises from transitions from P 2p to empty Ca 3d orbitals. Peak "d" seen in all phosphates is due to transitions from 2p to 3d orbital in phosphorous.

BIBLIOGRAPHY

The following references are specifically incorporated herein by reference:
1. V. Michel, et al., (2012), Pure and Applied Chemistry 84, pp. 377.
2. L. L. Hench and J. Wilson, (1993), An Introduction to Bioceramics. Singapore: World Scientific Publishing Co.
3. K. H. Kim and N. Ramaswamy. (2009), Dent. Mater. J. 28(1), pp. 20-36.
4. E. Nasatzky, J. et al. (2003), Refuat Hapeh Vehashinayim 20(3), pp. 8-19, 98.
5. Y. Sul, et al. (2009), Journal of Biomedical Materials Research Part A 89A(4), pp. 942-950.
6. H. S. Alghamdi, et al. (2013), Clin. Oral Implants Res. 24(5), pp. 475-483.
7. B. Kang, et al. (2012), Clin. Oral Implants Res. 23(6), pp. 690-697.
8. P. I. Branemark. (1983), J. Prosthet. Dent. 50(3), pp. 399-410.

9. J. Zupnik, S., et al. (2011), J. Periodontol. 82(10), pp. 1390-1395.
10. J. Rho, L. et al. (1998), Med. Eng. Phys. 20(2), pp. 92-102.
11. K. Athanasiou, C. et al. (2000), Tissue Eng. 6(4), pp. 361-381.
12. R. O. Ritchie (2011), Nat Mater 10(11), pp. 817-822.
13. S. Weiner and W. Traub (1992), FASEB J. 6(3), pp. 879-885.
14. R. Legros, et al. (1987), Calcif. Tissue Int. 41(3), pp. 137-144.
15. K. D. Cashman (2006), Int. Dairy J. 16(11), pp. 1389-1398.
16. D. J. HADJIDAKIS and I. I. ANDROULAKIS (2006), Ann. N. Y. Acad. Sci. 1092(1), pp. 385-396. 2006.
17. L. J. Raggatt, N. C. Partridge (2010), J. Biological Chemistry 285(33), pp. 25103-25108.
18. T. R. Arnett (2008), The Journal of Nutrition 138(2), pp. 415S-418S.
19. C. Deal (2009), Nat Clin Pract Rheum 5(1), pp. 20-27.
20. L. W. Fisher and N. S. Fedarko., Connect. Tissue Res. 44 Suppl 1 pp. 33-40. 2003.
21. A. George, et al. (1993), J. Biol. Chem. 268(17), pp. 12624-12630.
22. K. L. Hirst, K., et al. (1997), J. Dent. Res. 76(3), pp. 754-760.
23. R. N. D'Souza, et al. (1997), J. Bone Miner. Res. 12(12), pp. 2040-2049.
24. J. Q. Fen, et al. (2002), J. Bone Miner. Res. 17(10), pp. 1822-1831.
25. M. MacDougall, et al. (1998), J. Chen., J. Bone Miner. Res. 13(3), pp. 422-431.
26. L. Ye, M. et al. (2004), J. Biol. Chem. 279(18), pp. 19141-19148.
27. B. Lorenz-Depiereux, et al. (2006), Nat. Genet. 38(11), pp. 1248-1250.
28. C. Qin, et al., (2007), Journal of Dental Research 86(12), pp. 1134-1141.
29. G. He, et al. (2003), Nat. Mater. 2(8), pp. 552-558.
30. S. Gajjeraman, K., et al. (2007), Journal of Biological Chemistry 282(2), pp. 1193-1204.
31. P. H. Tartaix, M. et al. (2004), J. Biol. Chem. 279(18), pp. 18115-18120.
32. J. Q. Feng, et al. (2003), J. Dent. Res. 82(10), pp. 776-780.
33. L. Ye, Y., et al. (2005), J. Biol. Chem. 280(7), pp. 6197-6203.
34. Y. Ling, et al. (2005), Journal of Bone and Mineral Research 20(12), pp. 2169-2177.
35. B. D. Ratner, et al. (2004), Biomaterials Science: An Introduction to Materials in Medicine
36. J. Le Huec, T. et al. (1995), Biomaterials 16(2), pp. 113-118.
37. M. Akao, et al. (1982), J. Mater. Sci. 17(2), pp. 343-346.
38. J. Osborn and H. Newesely. (1980), Biomaterials 1(2), pp. 108-111.
39. J. Takeda, M. Niinomi and T. Akahori. (2004), Int. J. Fatigue 26(9), pp. 1003-1015.
40. M. N. Bureau, J. Denault and J. Legoux (2006), Implantable Biomimetic Prosthetic Bone
41. C. FRANCOIS (2008), Composite metallic materials, uses thereof and process for making same.
42. S. Teoh (2000), Int. J. Fatigue 22(10), pp. 825-837.
43. L. L. Hench (1998), Bioactive glasses and glass-ceramics. Presented at Materials Science Forum.
44. J. D. Bronzino (1992), Biomedical Engineering Handbook.
45. L. L. Hench (2006), J. Mater. Sci. Mater. Med. 17(11), pp. 967-978.
46. A. C. M. Renno, et al. (2013), BioMed Research International.
47. R. G. Flemming, et al. (1999), Biomaterials 20(6), pp. 573-588.
48. J. Q. Feng, et al., Nat. Genet. 38(11), pp. 1310-1315. 2006.
49. B. Lorenz-Depiereux, et al., (2006), Nat. Genet. 38(11), pp. 1248-1250.
50. L. D. Quarles. (2010), Exp. Cell Res. 318(9), pp. 1040-1048. 2012.
51. P. K. Spiegel. (1995), AJR Am. J. Roentgenol. 164(1), pp. 241-243.
52. M. L. Bouxsein, et al. (2010), J. Bone Miner. Res. 25(7), pp. 1468-1486.
53. B. Wopenka, et al. (2012), A. Kent, J. D. Pasteris, Y. Yoon and S. Thomopoulos. Appl. Spectrosc. 62(12), pp. 1285-1294.2008-12-01T00:00:00.
54. K. L. Stone, et al. (1947) Journal of Bone and Mineral Research 18(11), pp. 1947-1954. 2003.
55. D. H. Kohn, et al. (2009) Cells Tissues Organs 189(1-4), pp. 33-37. 2009.
56. A. Awonusi, et al. (2007), Carbonate assignment and calibration in the raman spectrum of apatite. 81(1), pp. 46-52. 2007.
57. O. Akkus, F. Adar and M. B. Schaffler (2004) Bone 34(3), pp. 443-453.
58. P. Roschger, et al., (1998), Bone 23(4), pp. 319-326.
59. S. Fujita, M. Ohshima and H. Iwata. (2009) J. R. Soc. Interface 6 Suppl 3 pp. S269-77.
60. K. Anselme, A. Ponche and M. Bigerelle (2010), Proc. Inst. Mech. Eng. H. 224(12), pp. 1487-1507.
61. A. K. Gaind and E. W. Hearn (1978) Journal of the Electrochemical Society 125(1), pp. 139-145.
62. C. J. Bettinger, R. Langer and J. T. Borenstein (2009), Angew. Chem. Int. Ed Engl. 48(30), pp. 5406-5415.
63. P. Clark, P. Connolly, A. S. Curtis, J. A. Dow and C. D. Wilkinson (1990), Topographical control of cell behaviour: II. multiple grooved substrata. Development 108(4), pp. 635-644.
64. M. Hartney, D. Hess and D. Soane (1989), Journal of Vacuum Science & Technology B 7(1), pp. 1-13.
65. S. Sivaram (1995), Chemical Vapor Deposition: Thermal and Plasma Deposition of Electronic Materials
66. V. A. Gritsenko, R. W. M. Kwok, H. Wong and J. B. Xu. (2002) J. Non Cryst. Solids 297(1), pp. 96-101.
67. N. Jehanathan, Y. Liu, B. Walmsley, J. Dell and M. Saunders, (2006), J. Appl. Phys. 100(12).
68. J. Campmany (1993), Optical, Appl. Surf. Sci. 70-71 pp. 695; 695-700; 700.
69. M. C. Poon, C. W. Kok, H. Wong and P. J. Chan. (2004) Thin Solid Films 462-463(0), pp. 42-45.
70. J. Chan, H. Wong, M. C. Poon and C. W. Kok (2003) Microelectronics Reliability 43(4), pp. 611-616.
71. K. -. Behrens, E. -. Klinkenberg, J. Finster and K. -. Meiwes-Broer (1998), Surf. Sci. 402-404(0), pp. 729-733.
72. F. Ay and A. Aydinli (2004), Optical Materials 26(1), pp. 33-46.
73. W. H. Zachariasen (1932), J. Am. Chem. Soc. 54(10), pp. 3841-3851.
74. H. R. Philipp (1971), Journal of Physics and Chemistry of Solids 32(8), pp. 1935-1945.
75. R. Tarey, et al., (1987), The Rigaku Journal 4(1), pp. 11-15.
76. G. Bona, et al., (2003), IBM Journal of Research and Development 47(2.3), pp. 239-249.

77. M. Hussein, et al. (2001), Characterization of thermally treated PECVD SiON layers.
78. A. G. Thorsness and A. J. Muscat (2003), J. Electrochem. Soc. 150(12), pp. F219-F228.
79. W. Lanford and M. Rand (1978), J. Appl. Phys. 49(4), pp. 2473-2477.
80. W. Cao and L. L. Hench (1996), Bioactive materials. Ceram. Int. 22(6), pp. 493-507.
81. S. Padilla, et al., (2006), Acta Biomaterialia 2(3), pp. 331-342.
82. H. Kim, et al. (2005), Biomaterials 26(21), pp. 4366-4373.
83. E. Dos Santos, et al., (2009), Journal of Biomedical Materials Research Part A 89(2), pp. 510-520.
84. I. D. Xynos, et al. (2001), J. Biomed. Mater. Res. 55(2), pp. 151-157.
85. P. N. Kumta, et al., (2005), Acta Biomaterialia 1(1), pp. 65-83.
86. C. Ning, et al., (2005), J. Mater. Sci. Mater. Med. 16(4), pp. 355-360.
87. L. L. Hench, et al., (1971), J. Biomed. Mater. Res. 5(6), pp. 117-141.
88. T. Kokubo, H. Kushitani, S. Sakka, T. Kitsugi and T. Yamamuro (1990), J. Biomed. Mater. Res. 24(6), pp. 721-734.
89. Y. K. Lee, et al., (2004), J. Biomed. Mater. Res. A. 69(1), pp. 188-195.
90. T. Kokubo and H. Takadama (2006) How useful is SBF in predicting in vivo bone bioactivity? Biomaterials 27(15), pp. 2907-2915.
91. T. Kokubo, et al., (1992), J. Mater. Sci. Mater. Med. 3(2), pp. 79-83.
92. S. A. Redey, et al., (1999), J. Biomed. Mater. Res. 45(2), pp. 140-147.
93. D. W. Murray, T. Rae and N. Rushton (1989), J. Bone Joint Surg. Br. 71(4), pp. 632-637.
94. K. Webb, V. Hlady and P. A. Tresco. (1998), J. Biomed. Mater. Res. 41(3), pp. 422-430.
95. B. Feng, J. Y. Chen, S. K. Qi, L. He, J. Z. Zhao and X. D. Zhang (2002), J. Mater. Sci. Mater. Med. 13(5), pp. 457-464.
96. N. Jaiswal, et al., (1997), J. Cell. Biochem. 64(2), pp. 295-312.
97. S. R. Bare (2005), XANES measurements and interpretation. Presented on EXAFS Data Collection and Analysis Course, APS.
98. C. Bergwitz and H. Jüppner (2010), Annu. Rev. Med. 61(1), pp. 91-104.
99. A. Rangiani, et al., (2012) PLoS One 7(8), pp. e42329.
100. J. D. Termine and D. R. Lundy (1973), Hydroxide and carbonate in rat bone mineral and its synthetic analogues. 13(1), pp. 73-82. 1973.
101. E. Donnelly, A. L. Boskey, S. P. Baker and M. C. van der Meulen (2010), J. Biomed. Mater. Res. A. 92(3), pp. 1048-1056.
102. O. O. Aruwajoye, et al., (2013), Bone 52(2), pp. 632-639. 2013.
103. H. Demirkiran, et al., (2011), Materials Science and Engineering: C 31(2), pp. 134-143.
104. J. Kruse, et al., (2009), Journal of Synchrotron Radiation 16(2), pp. 247-259.
105. J. Rajendran, S. Gialanella and P. B. Aswath (2013), Materials Science and Engineering: C 33(7), pp. 3968-3979.
106. S. Toyosawa, S. Shintani, T. Fujiwara, T. Ooshima, A. Sato, N. Ijuhin and T. Komori (2001), J. Bone Miner. Res. 16(11), pp. 2017-2026.
107. A. Bigi, et al., (1997), J. Inorg. Biochem. 68(1), pp. 45-51.
108. J. M. Burnell, E. J. Teubner and A. G. Miller (1980), Calcif. Tissue Int. 31(1), pp. 13-19.
109. C. Rey, B. Collins, T. Goehl, I. R. Dickson and M. J. Glimcher (1989), Calcif. Tissue Int. 45(3), pp. 157-164.
110. A. E. T. Kuiper, et al., (1983), Journal of Vacuum Science & Technology B 1(1), pp. 62-66.
111. V. G. Varanasi, et al., (2012), J. Oral Implantol. 38(4), pp. 325-336.
112. D. Bruggeman (1935), Annalen Der Physik 24(7), pp. 636-664.
113. M. Amaral, M. A. Lopes, J. D. Santos and R. F. Silva (2002), Biomaterials 23(20), pp. 4123-4129.
114. N. T. Correia, et al., (1997), J. Colloid Interface Sci. 189(2), pp. 361-369.
115. D. H. Kaelble (1970), The Journal of Adhesion 2(2), pp. 66-81.
116. D. K. Owens and R. C. Wendt (1969), J Appl Polym Sci 13(8), pp. 1741-1747.
117. R. van Weeren, E. A. Leone, S. Curran, L. C. Klein and S. C. Danforth (1994), J Am Ceram Soc 77(10), pp. 2699-2702.
118. S. A. Redey, et al., (1999), J. Biomed. Mater. Res. 45(2), pp. 140-147.
119. M. Flrrr and R. Sncco et al. (1994), Am. Mineral. 79 pp. 622-632.
120. M. Kasrai, et al. (1996), Appl. Surf. Sci. 99(4), pp. 303-312.
121. D. Li, G. Bancroft, M. Kasrai, M. Fleet, X. Feng, K. Tan and B. Yang (1993), Solid State Commun. 87(7), pp. 613-617.
122. H. Demirkiran, et al. (2011), Materials Science and Engineering: C 31(2), pp. 134-143.
123. D. Li, G. Bancroft and M. Fleet (1996), Am. Mineral. 81(1-2), pp. 111-118.
124. P. Wilson (2011), Nanoscale Research Letters 6(1), pp. 168.
125. D. Criado, et al., (2004), Materials Science and Engineering: B 112(2-3), pp. 123-127.
126. F. Pinakidou, M. Katsikini and E. C. Paloura. (2003), XAFS characterization of buried SixNyOz samples. Nuclear Instruments and Methods in Physics Research Section B: Beam Interactions with Materials and Atoms 200(0), pp. 66-72.
127. S. A. Redey, et al. (1999), J. Biomed. Mater. Res. 45(2), pp. 140-147.
128. L. J. Skipper, et al. (2005), J. Mater. Chem. 15(24), pp. 2369-2374
129. R. A. Martin, et al. (2009), J. Mater. Sci. Mater. Med. 20(4), pp. 883-888.
130. V. FitzGerald, D. et al. (2009), Physics and Chemistry of Glasses-European Journal of Glass Science and Technology Part B 50(3), pp. 137-143.
131. V. FitzGerald, et al. (2009), Journal of Biomedical Materials Research Part A 91(1), pp. 76-83.
132. T. D. Schmittgen and K. J. Livak (2008), Nature Protocols 3(6), pp. 1101-1108.
133. I. Idris and O. Sugiura (1998), Japanese Journal of Applied Physics 37(12R), pp. 6562.
134. Ö Andersson and I. Kangasniemi (1991), J. Biomed. Mater. Res. 25(8), pp. 1019-1030.
135. G. Harp, et al. (1990), Phys. Scripta 1990 (T31), pp. 23.
136. R. Bnvoso (1994), Am. Mineral. 79 pp. 411-425.
137. H. Nojiri, et al. (2011), Journal of Bone and Mineral Research 26(11), pp. 2682-2694.

138. M. A. K. Liebschner and M. A. Wettergreen (2003), Topics in Tissue Engineering, N. Ashammakhi and Ferretti P., Eds.
139. V. G. Varanasi, et al. (2011), Journal of Biomedical Materials Research Part A 98(2), pp. 177-184.
140. H. J. Busscher, et al. (1984), Colloids and Surfaces 9(4), pp. 319-331.
141. R. Franke and J. Hormes (1995), Physica B: Condensed Matter 216(1), pp. 85-95.
142. A. Tilocca and A. N. Cormack (2007) J Phys Chem B 111(51), pp. 14256-14264.
143. J. R. Jones et al. (2001), J. Biomed. Mater. Res. 58(6), pp. 720-726.
144. J. Isaac, J. et al. (2011), Eur Cell Mater 21 pp. 130-143.
145. M. Milona, et al. (2003), BMC Genomics 4(1), pp. 1-11.
146. V. G. Varanasi, et al. (2009), Acta Biomater. 5(9), pp. 3536-3547.
147. M. Bosetti, et al. (2003), J. Biomed. Mater. Res. A. 64(1), pp. 189-195.
148. D. T. Grider, S. Hattangady and R. Kraft (2000), Method of Forming Thin Silicon Nitride Or Silicon Oxynitride Gate Dielectrics
149. A. N. Cormack (2002), "The structure of bioactive glasses and their surfaces," in Bio-Glasses Anonymous
150. I. Elgayar, A. Aliev, A. Boccaccini and R. Hill (2005), J. Non Cryst. Solids 351(2), pp. 173-183.
151. A. Pedone, et al. (2010), Chemistry of Materials 22(19), pp. 5644-5652.
152. V. FitzGerald, et al. (2007), Advanced Functional Materials 17(18), pp. 3746-3753.
153. M. Cerruti, et al. (2005), The Journal of Physical Chemistry B 109(30), pp. 14496-14505.
154. A. Tilocca, A. N. et al. (2007), Chemistry of Materials 19(1), pp. 95-103.
155. P. Galliano et al. (1994), Mater. Res. Bull. 29(12), pp. 1297-1306.
156. A. Li, et al. (2011), J. Non Cryst. Solids 357(19), pp. 3548-3555.
157. W. Lai, et al. (2005), Journal of Biomedical Materials Research Part A 75(2), pp. 398-407.
158. T. H. Tranah, et al. (2013), Metab. Brain Dis. 28(1), pp. 1-5.
159. J. L. Arias, et al. (2003), Biomaterials 24(20), pp. 3403-3408.
160. J. Gomez-et al. (2000), Biomaterials 21(2), pp. 105-111.

What is claimed is:

1. A medical implantable device comprising at least one treated surface comprising an amorphous silicon oxynitrophosphide (Si—O—N—P) layer, wherein the at least one treated surface provides for release of Si-ion such that calcium phosphate mineral forms on the at least one treated surface after in vivo implantation of the device.

2. The device of claim 1, wherein the at least one treated surface is a metal, ceramic, polymer, glass, or composite hybrid material of metal, ceramic, polymer or glass surface.

3. The device of claim 1, wherein the amorphous silicon oxynitrophosphide layer is deposited onto the at least one treated surface via plasma-etched chemical vapor deposition (PECVD) using a silicon based reagent and $PH_3$.

4. The device of claim 1, wherein the at least one treated surface is a ceramic surface.

5. The device of claim 1, wherein the amorphous silicon oxynitrophosphide layer has a thickness of about 1 nanometer to about 999 nanometers.

6. The device of claim 1, wherein the amorphous silicon oxynitrophosphide layer has a thickness of about 0.001 millimeters to about 0.999 millimeters.

7. The device of claim 1, wherein the amorphous silicon oxynitrophosphide is $Si_{2.27}O_{1.58}N_{0.13}P_{0.018}$.

8. The device of claim 1, wherein the amorphous silicon oxynitrophosphide layer comprises a composition selected from the group consisting of:
   (a) 3.2% $SiO_2$-37.7% amorphous silicon (a-Si)-58.9% $Si_2N_4$-0.24% $P_2O_5$;
   (b) 6.3% $SiO_2$-39.6% a-Si-53.8% $Si_2N_4$-0.25% $P_2O_5$;
   (c) 11.0% $SiO_2$-35.4% a-Si-53.4% $Si_2N_4$-0.28% $P_2O_5$;
   (d) 21.27% $SiO_2$-31.5% a-Si-46.9% $Si_2N_4$-0.27% $P_2O_5$;
   (e) 2.28% $SiO_2$-1.54% a-Si-0.16% $Si_2N_4$-0.015% $P_2O_5$; and
   (f) 2.27% $SiO_2$-1.58% a-Si-0.13% $Si_2N_4$-0.018% $P2O_5$.

9. The device of claim 1, wherein the at least one treated surface further comprises one or more silicon-based layers.

10. The device of claim 1, wherein the amorphous silicon oxynitrophosphide layer comprises:
    about 0.2 atomic % to about 1.5 atomic % of P;
    about 55 atomic % to about 65 atomic % of Si;
    about 2.0 atomic % to about 34.0 atomic % of N; and
    about 1.0 atomic % to about 40 atomic % of O.

11. The device of claim 1, wherein the amorphous silicon oxynitrophosphide layer comprises:
    about 55 atomic % to about 65 atomic % of Si;
    about 0.2 atomic % to about 0.5 atomic % of P; and
    about 1 atomic % to about 45 atomic % of O.

* * * * *